United States Patent [19]

Peter et al.

[11] 3,932,465

[45] Jan. 13, 1976

[54] 3-R-METHYL-7-AMINO-CEPH-EM-4-CARBOXYLIC ACID COMPOUNDS

[75] Inventors: Heinrich Peter, Riehen, Switzerland; Herman Robert Rodriguez, New York, N.Y.; Hans Bickel, Binningen, Switzerland

[73] Assignee: Ciba-Geigy Corporation, Ardsley, N.Y.

[22] Filed: July 2, 1971

[21] Appl. No.: 159,527

[30] Foreign Application Priority Data
July 8, 1970   Switzerland....................... 10305/70

[52] U.S. Cl................................. 260/243 C; 424/246
[51] Int. Cl.$^2$....................................... C07D 501/20
[58] Field of Search ............................. 260/243 C

[56] References Cited
UNITED STATES PATENTS

| | | | |
|---|---|---|---|
| 3,539,562 | 11/1970 | Diassi et al...................... | 260/243 C |
| 3,641,021 | 2/1972 | Ryan............................... | 260/243 C |

*Primary Examiner*—Nicholas S. Rizzo
*Attorney, Agent, or Firm*—Joseph G. Kolodny; John J. Maitner; Theodore O. Groeger

[57] ABSTRACT

3-R-Methyl-7-amino-ceph-2-em-4ξ-carboxylic acid compounds, in which R is the C-residue of a C-nucleophilic compound are valuable intermediates, for example, in the manufacture of the corresponding 3-R-methyl-7-amino-ceph-3-em-4-carboxylic acid compounds with antibiotic properties.

10 Claims, No Drawings

3-R-METHYL-7-AMINO-CEPH-EM-4-CARBOXYLIC ACID COMPOUNDS

The subject of the present invention are 7-N-$R_1^a$-N-$R_1^b$-amino-3-R-methyl-ceph-2-em-4$\xi$-carboxylic acid compounds of formula

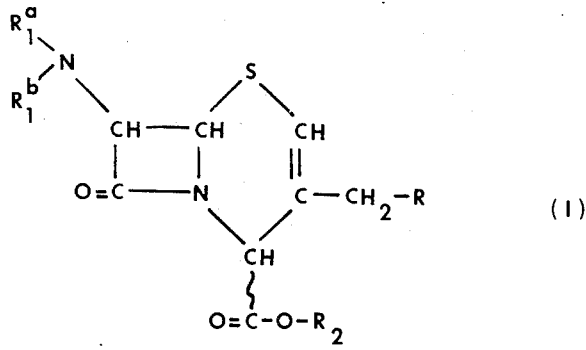

wherein R represents a radical, possessing a hydrogen and being bonded via a carbon atom, of an organic C-nucleophilic compound, $R_1^a$ represents hydrogen or an amino protective group $R_1^A$, and $R_1^b$ represents hydrogen or an acyl group Ac, or $R_1^A$ and $R_1^b$ together denote a bivalent amino protective group, and $R_2$ represents hydrogen or a radical $R_2^A$ which together with the —C(=O)—O— grouping forms a protective carboxyl group, or salts of such compounds which have salt-forming groups, furthermore, the manufacture of such compounds.

Hydrogen-containing radicals, bonded via a carbon atom, of C-nucleophilic organic compounds (represented by the group R in the above formula I) are corresponding C-residues (i.e. g bonded via a carbon atom with the methyl group) of organic, preferably unsaturated or enolisible, compounds which possess at least one carbon atom capable of electron enrichment, through which the radical R is bound to the methylene group. These are above all compounds which contain at least one double bond activated by one or more oxygen, sulphur and/or nitrogen atoms, or compounds which can be converted into these by tautomerism.

Such radicals are especially carbocyclic aryl radicals containing O-, S- or N-substituents, and also O-, S- or N-heterocyclic radicals of aromatic character, bonded via carbon atoms and having an uneven number of ring members in the hetero-ring, or ethenyl radicals containing O-, S- or N-substituents and optionally bonded with the methyl radical via one or more conjugated double bonds, or corresponding tautomeric radicals, furthermore methyl groups substituted by acyl or functionally modified carboxyl groups, preferably two such radicals.

An amino protective group $R_1^A$ is, for example, one of the generally known groups of this nature, such as a triarylmethyl group, for example trityl group, or an organic silyl group, for example trimethylsilyl group, as well as a stannyl group, or above all an acyl group Ac. The latter, which can also stand for $R_1^b$, above all represents the acyl radical of an optionally substituted aliphatic, cycloaliphatic, cycloaliphatic-aliphatic, aromatic, araliphatic, heterocyclic or heterocyclic-aliphatic carboxylic acid (including formic acid), or the acyl radical of an appropriate organic sulphonic acid, as well as the acyl radical of a carbonic acid half-derivative.

A bivalent amino protective group formed by the radicals $R_1^A$ and $R_1^b$ together is, in particular, the bivalent acyl radical of an organic dicarboxylic acid, above all the diacyl radical of an aliphatic or aromatic dicarboxylic acid, and also the acyl radical of an α-aminoacetic acid which is preferably substituted in the α-position, for example, containing an aromatic or heterocyclic radical, wherein the amino group is bonded to the nitrogen atom via a methylene radical which is preferably substituted, for example by two lower alkyl groups, such as methyl groups. The radicals $R_1^a$ and $R_1^b$ can together also represent an organic ylidene radical, such as an aliphatic, cycloaliphatic, cycloaliphatic-aliphatic or araliphatic ylidene radical.

A protected carboxyl group of the formula —C(=O)—O—$R_2^A$ is above all an esterified carboxyl group, but can also be an anhydride group, which is usually a mixed anhydride group.

The group $R_2^A$ can represent an organic radical, which together with the —C(=O)—O— grouping forms an esterified carboxyl group which can preferably be split easily; such radicals are, for example, aliphatic, cycloaliphatic, cycloaliphatic-aliphatic, aromatic or araliphatic radicals, especially optionally substituted hydrocarbon radicals of this nature, as well as heterocyclic or heterocyclic-aliphatic radicals.

The group $R_2^A$ can also represent an organic silyl radical, as well as an organic-metallic radical, such as an appropriate organic stannyl radical, especially a silyl or stannyl radical substituted by 1 to 3, optionally substituted, hydrocarbon radicals, such as aliphatic hydrocarbon radicals.

A radical $R_2^A$ which forms a - preferably mixed - anhydride group with the —C(=O)—O— grouping is preferably the acyl radical of an organic carboxylic acid, such as an aliphatic, cycloaliphatic, cycloaliphatic-aliphatic, aromatic or araliphatic carboxylic acid, or of a carbonic acid half-derivative, such as of a carbonic acid half-ester.

The general terms used in the preceding and following description for example have the following meanings:

An aliphatic radical, including the aliphatic radical of a corresponding organic carboxylic acid or sulphonic acid, as well as a corresponding ylidene radical, is an optionally substituted, monovalent or divalent, aliphatic hydrocarbon radical, especially lower alkyl, as well as lower alkenyl or lower alkinyl, and also lower alkylidene, which can, for example, contain up to 7, preferably up to 4, carbon atoms. Such radicals can optionally be monosubstituted, disubstituted or polysubstituted by functional groups, for example, by free, etherified or esterified hydroxyl or mercapto groups, such as lower alkoxy, lower alkenyloxy, lower alkylenedioxy, optionally substituted phenyloxy or phenyl-lower alkoxy, lower alkylthio or optionally substituted phenylthio or phenyl-lower alkylthio, lower alkoxycarbonyloxy or lower alkanoyloxy, or halogen, and also by oxo, nitro, optionally substituted amino, for example di-lower alkylamino, lower alkyleneamino, oxa-lower alkyleneamino or aza-lower alkyleneamino, as well as acylamino, such as lower alkanoylamino, optionally substituted carbamoylamino, ureidocarbonylamino or guanidinocarbonylamino, azido, acyl, such as lower alkanoyl or benzoyl, optionally functionally modified carboxyl, such as carboxyl present in the salt form, esterified carboxyl, such as lower alkoxycarbonyl, optionally substituted carbamoyl, such as N-lower alkylcarbamoyl or N,N-di-lower alkylcarbamoyl, and also optionally substituted ureidocarbonyl or guanidinocarbonyl, or nitrile, optionally functionally modified sulpho, such as sulphamoyl, or sulpho present in the salt form.

The divalent aliphatic radical of an aliphatic carboxylic acid is, for example, lower alkylene or lower alkenylene, which can optionally be monosubstituted, disubstituted or polysubstituted, for example like an aliphatic radical indicated above.

A cycloaliphatic or cycloaliphatic-aliphatic radical, including the cycloaliphatic or cycloaliphatic-aliphatic radical in a corresponding organic carboxylic acid or sulphonic acid, or a corresponding cycloaliphatic or cycloaliphatic-aliphatic ylidene radical, is an optionally substituted, monovalent or divalent, cycloaliphatic or cycloaliphatic-aliphatic, hydrocarbon radical, for example, monocyclic, bicyclic or polycyclic cycloalkyl or cycloalkenyl, also cycloalkylidene, or cycloalkyl or cycloalkenyl-lower alkyl or cycloalkenyl-lower alkenyl, as well as cycloalkyl-lower alkylidene or cycloalkenyl-lower alkylidene, wherein cycloalkyl and cycloalkylidene for example contains up to 12, such as 3–8, preferably 3–6, ring carbon atoms, whilst cycloalkenyl for example possesses up to 12, such as 3–8, for example 5–8, preferably 5 or 6, ring carbon atoms, as well as 1 to 2 double bonds, and the aliphatic part of a cycloaliphatic-aliphatic radical can, for example, contain up to 7, preferably up to 4, carbon atoms. The above cycloaliphatic or cycloaliphatic-aliphatic radicals can, if desired, be monosubstituted, disubstituted or polysubstituted, for example by optionally substituted aliphatic hydrocarbon radicals, such as by the abovementioned, optionally substituted lower alkyl groups, or, for example like the abovementioned aliphatic hydrocarbon radicals, by functional groups.

The aromatic radical, including the aromatic radical of a corresponding carboxylic acid or sulphonic acid, is an optionally substituted aromatic hydrocarbon radical, for example a monocyclic, bicyclic or polycyclic aromatic hydrocarbon radical, in particular phenyl, as well as biphenylyl or naphthyl, which can optionally be monosubstituted, disubstituted or polysubstituted, for example like the abovementioned aliphatic and cycloaliphatic hydrocarbon radicals.

The divalent aromatic radical of an aromatic carboxylic acid is above all a 1,2-arylene, especially 1,2-phenylene, which can optionally be monosubstituted, disubstituted or polysubstituted, for example like the abovementioned aliphatic and cycloaliphatic hydrocarbon radicals.

The araliphatic radical, including the araliphatic radical in a corresponding carboxylic acid or sulphonic acid, and also an araliphatic ylidene radical, is, for example, an optionally substituted araliphatic hydrocarbon radical, such as an optionally substituted aliphatic hydrocarbon radical which, for example, possess up to three, optionally substituted, monocyclic, bicyclic or polycyclic aromatic hydrocarbon radicals, and above all represent phenyl-lower alkyl or phenyl-lower alkenyl, as well as phenyl-lower alkinyl and also phenyl-lower alkylidene, and such radicals, for example, contain 1–3 groups and can optionally be monosubstituted, disubstituted or polysubstituted in the aromatic and/or aliphatic part, for example like the abovementioned aliphatic and cycloaliphatic radicals.

Heterocyclic groups, including those in heterocyclic-aliphatic radicals, including heterocyclic or heterocyclic-aliphatic groups in corresponding carboxylic acids or sulphonic acids, are especially monocyclic, as well as bicyclic or polycyclic, azacyclic, thiacyclic, oxacyclic, thiazacyclic, thiadiazacyclic, oxazacyclic, diazacyclic, triazacyclic or tetrazacyclic radicals of aromatic character, and also corresponding partially or wholly saturated radicals, and these heterocyclic radicals can optionally be monosubstituted, disubstituted or polysubstituted, for example like the abovementioned cycloaliphatic radicals. The aliphatic part in heterocyclic-aliphatic radicals for example has the meaning given for the corresponding cycloaliphatic-aliphatic or araliphatic radicals.

The acyl radical of a carbonic acid half-derivative is preferably the acyl radical or a corresponding half-ester, wherein the organic radical of the ester group represents an optionally substituted aliphatic, cycloaliphatic, aromatic or araliphatic hydrocarbon radical or a heterocyclic-aliphatic radical, above all the acyl radical of a lower alkyl half-ester, which is optionally substituted, for example in the α-position or β-position, of carbonic acid, and of a lower alkenyl, cycloalkyl, phenyl or phenyl-lower alkyl half-ester of carbonic acid which is optionally substituted in the organic radical. Acyl radicals of a carbonic acid half-ester are, further, corresponding radicals of lower alkyl half-esters of carbonic acid, in which the lower alkyl part contains a heterocyclic group, for example one of the abovementioned heterocyclic groups of aromatic character, and both the lower alkyl radical and the heterocyclic group can optionally be substituted. The acyl radical of a carbonic acid half-derivative can also represent an optionally N-substituted carbamoyl group, such as an optionally halogenated carbamoyl group.

Lower alkyl is, for example, methyl, ethyl, n-propyl, isopropyl, n-butyl, isobutyl, sec.-butyl or tert.-butyl, as well as n-pentyl, isopentyl, n-hexyl, isohexyl or n-heptyl, whilst lower alkenyl can, for example, be vinyl, allyl, isopropenyl, 2- or 3-methallyl or 3-butenyl, lower alkinyl can, for example, be propargyl or 2-butinyl, and lower alkylidene can, for example, be isopropylidene or isobutylidene.

Lower alkylene is, for example, 1,2-ethylene, 1,2- or 1,3-propylene or 1,4-butylene, whilst lower alkenylene is, for example, 1,2-ethenylene.

Cycloalkyl is, for example, cyclopropyl, cyclobutyl, cyclopentyl, cyclohexyl or cycloheptyl, as well as adamantyl, cycloalkenyl is, for example, 2-cyclopentyl, 2- or 3-cyclopentenyl, 1-, 2- or 3-cyclohexenyl, 3-cycloheptenyl or 1,4-cyclohexadienyl, and cycloalkylidene is, for example, cyclopentylidene or cyclohexylidene. -Cycloalkyl-lower alkyl or cycloalkyl-lower alkenyl is, for example, cyclopropyl-, cyclopentyl-, cyclohexyl- or cycloheptyl-methyl, -1,1- or -1,2-ethyl, -1,1-, -1,2- or -1,3-propyl, -vinyl or -allyl, whilst cycloalkenyl-lower alkyl or cycloalkenyl-lower alkenyl for example represents 1-, 2- or 3-cyclopentenyl-, 1-, 2- or 3-cyclohexenyl- or 1-, 2- or 3-cycloheptenyl-methyl, -1,1- or -1,2-ethyl, -1,1-, -1,2- or -1,3-propyl, -vinyl or -allyl. Cycloalkyl-lower alkylidene is, for example, cyclohexylmethylene, and cycloalkenyl-lower alkylidene is, for example, 3-cyclohexenylmethylene.

Naphthyl is 1- or 2-naphthyl, whilst biphenylyl for example represents 4-biphenylyl.

Phenyl-lower alkyl or phenyl-lower alkenyl is, for example, benzyl, 1- or 2-phenylethyl, 1-, 2- or 3-phenylpropyl, diphenylmethyl, trityl, 1- or 2-naphthylmethyl, styryl or cinnamyl, and phenyl-lower alkylidene is, for example, benzylidene.

Heterocyclic radicals are above all optionally substituted heterocyclic radicals of aromatic character, for example appropriate monocyclic, monoazacyclic, monothiacyclic or monooxacyclic radicals, such as pyrryl, for example 2-pyrryl or 3-pyrryl, pyridyl, for example 2-, 3- or 4-pyridyl, and also pyridinium, thienyl, for example 2-thienyl, or furyl, for example 2-furyl, bicyclic monoazacyclic, monooxacyclic or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl, monocyclic diazacyclic, triazacyclic, tetrazacyclic, thiazacyclic, thiadiazacyclic or oxazacyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3-isoxazolyl, thiazolyl, for example 2-thiazolyl, isothiazolyl, for example 3-isothiazolyl or 1,2,4- or 1,3,4-thiadiazolyl, for example 1,2,4-thiadiazol-3-yl or 1,3,4-thiadiazol-2-yl, or bicyclic diazacyclic, thiazacyclic or oxazacyclic radicals, such as benzimidazolyl, for example 2-bemzimidazolyl, benzoxazolyl, for example 2-benzoxazolyl, or benzthiazolyl, for example 2-benzthiazolyl. Corresponding partially or wholly saturated radicals are, for example, tetrahydrothienyl, such as 2-tetrahydrothienyl, tetrahydrofuryl, such as 2-tetrahydrofuryl, or piperidyl, for example 2- or 4-piperidyl. Heterocyclic-aliphatic radicals are heterocyclic groups, especially those mentioned above, which contain lower alkyl or lower alkenyl. The abovementioned heterocyclyl radicals can be substituted, for example by optionally substituted aliphatic hydrocarbon radicals, especially lower alkyl, such as methyl, or, for example like the aliphatic hydrocarbon radicals, by functional groups.

Lower alkoxy is, for example, methoxy, ethoxy, n-propoxy, isopropoxy, n-butoxy, isobutoxy, sec.-butoxy, tert.-butoxy, n-pentoxy or tert.-pentoxy. These groups can be substituted, for example as in halogeno-lower alkoxy, especially 2-halogeno-lower alkoxy, for example 2,2,2-trichloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylidenedioxy, cycloalkoxy is, for example, cyclopentoxy, cyclohexoxy or adamantyloxy, phenyl-lower alkoxy, for example benzyloxy or 1- or 2-phenylethoxy, or heterocyclyloxy or heterocyclyl-lower alkoxy, for example pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example methylthio, ethylthio or n-butylthio, lower alkenylthio is, for example allylthio, and phenyl-lower alkylthio is, for example benzylthio, whilst mercapto groups etherified by heterocyclyl radicals or heterocyclyl-aliphatic radicals are, especially, imidazolylthio, for example 2-imidazolylthio, thiazolylthio for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are, above all, halogen, for example fluorine, chlorine, bromine or iodine, as well as lower alkanoyloxy, for example acetoxy or propionyloxy.

Lower alkoxy-carbonyl is, for example, methoxycarbonyl, ethoxycarbonyl, n-propoxycarbonyl, isopropoxycarbonyl, tert.-butoxycarbonyl or tert.-pentoxycarbonyl.

N-lower alkyl-carbamoyl or N,N-di-lower alkyl-carbamoyl is, for example N-methylcarbamoyl, N-ethylcarbamoyl, N,N-dimethylcarbamoyl or N,N-diethylcarbamoyl, whilst N-lower alkylsulphamoyl for example represents N-methylsulphamoyl or N,N-dimethylsulphamoyl.

A carboxyl or sulpho group present in the alkali metal salt form is, for example, a carboxyl or sulpho group present in the sodium salt or potassium salt form.

Lower alkylamino or di-lower alkylamino is, for example, methylamino, ethylamino, dimethylamino or diethylamino, lower alkyleneamino is, for example, pyrrolidino or piperidino, oxa-lower alkyleneamino is, for example, morpholino, and aza-lower alkyleneamino is, for example, piperazino or 4-methylpiperazino. Acylamino especially represents carbamoylamino, lower alkylcarbamoylamino, such as methylcarbamoylamino, ureidocarbonylamino, guanidinocarbonylamino, lower alkanoylamino, such as acetylamino or propionylamino, and also phthalimido, or sulphoamino which is optionally present in the salt form, such as the alkali metal, for example sodium, salt form or ammonium salt form.

Lower alkanoyl is, for example, acetyl or propionyl.

Lower alkenyloxycarbonyl is, for example, vinyloxycarbonyl, whilst cycloalkoxycarbonyl and phenyl-lower alkoxycarbonyl for example represents adamantyloxycarbonyl, benzyloxycarbonyl, diphenylmethoxycarbonyl or α-4-biphenylyl-α-methylethoxycarbonyl. Lower alkoxycarbonyl, wherein lower alkyl for example contains a monocyclic, monoazacyclic, monooxacyclic, or monothiacyclic group, is, for example, furyl-lower alkoxycarbonyl, such as furfuryloxycarbonyl, or thienyl-lower alkoxycarbonyl, for example thenyloxycarbonyl.

Aryl radicals R which contain O-, S- or N-substituents are especially monocyclic or bicyclic, and also polycyclic, aryl radicals, above all phenyl radicals, as well as naphthyl or biphenylyl radicals, and also anthryl, phenanthryl or fluorenyl radicals, and such radicals can optionally contain further substituents in addition to the O-, S- and N-substituents.

O- and S-substituents of carbocyclic aryl radicals R are free or etherified hydroxyl groups, as well as corresponding mercapto groups. Etherified hydroxyl groups in particular contain optionally substituted hydrocarbon radicals, such as optionally substituted aliphatic, cycloaliphatic, cycloaliphatic-aliphatic, aromatic or araliphatic hydrocarbon radicals, as well as heterocyclic or heterocyclic-aliphatic residues as etherifying groups. Etherified hydroxyl groups are above all optionally substituted lower alkoxy groups, as well as lower alkenyloxy, lower alkylenedioxy, cycloalkoxy, aryloxy, such as optionally substituted phenyloxy, or aryl-lower alkoxy, such as optionally substituted phenyl-lower alkoxy, groups. Etherified mercapto groups are, for example, corresponding mercapto groups etherified by optionally substituted hydrocarbon radicals, for example lower alkylthio groups.

N-substituents of carbocyclic aryl radicals R are free or monosubstituted or disubstituted amino groups of basic character, wherein substituents represent optionally substituted hydrocarbon radicals, such as for example optionally substituted aliphatic, cycloaliphatic, cycloaliphatic-aliphatic, aromatic or aralyphatic hydrocarbon radicals, possible radicals being not only monovalent radicals but also divalent radicals, especially optionally substituted divalent aliphatic hydrocarbon radicals, which can additionally be interrupted by hetero-atoms, such as oxygen, sulphur or optionally substituted nitrogen atoms. Such amino groups are, for example, amino, lower alkylamino, dilower alkylamino, lower alkyleneamino, lower oxaalkyleneamino, e.g. morpholino, lower thiaalkyleneamino, e.g. thiomorpholino, lower azaalkyleneamino, such as N-lower alkyl-lower azaalkylene-amino, e.g. 4-lower alkylpiperazino, arylamino, such as phenylamino or N-lower alkyl-N-phenyl-amino, and aryl-lower alkyl-amino, such as phenyl-lower alkylamino or N-lower alkyl-N-phenyl-lower alkylamino groups.

Additional substituents of the abovementioned aromatic hydrocarbon radicals are, for example, optionally substituted hydrocarbon radicals, such as for example aliphatic, cycloaliphatic, aromatic or araliphatic hydrocarbon radicals which are optionally substituted, for example by free or functionally modified hydroxyl, or free or substituted amino groups, such as lower alkyl, cycloalkyl, cycloalkenyl, phenyl or phenyl-lower alkyl groups, and also functional groups, for example esterified hydroxyl groups, such as halogen atoms or acyloxy groups, acylamino groups, nitro groups or optionally functionally modified carboxyl groups, such as lower alkoxycarbonyl or cyano groups.

O-, S- or N-heterocyclic C-radicals of aromatic character, wherein the hetero-ring possesses an uneven number of ring members, are optionally substituted monocyclic or bicyclic, and also polycyclic oxacyclic, thiacyclic or azacyclic C-radicals of aromatic character, which preferably contain one, but also several, hetero-atoms as ring members. Preferred O-, S- and N-heterocyclic groups of aromatic character of this nature are above all at most bicyclic, oxacyclic, thiacyclic and azacyclic C-radicals of aromatic character, such as C-furyl, for example 2-furyl, C-benzofuryl, e.g. 2-benzofuryl, C-thienyl, for example 2- or 3-thienyl, C-benzothienyl, e.g. 3-benzothienyl, C-pyrryl, for example 2- or 3-pyrryl, or C-indolyl, for example 3-indolyl, or C-pyrazolyl, e.g. 3-pyrazolyl, or C-imidazolyl, e.g. 2-imidazolyl, radicals, whereby such radicals can be substituted, for example by optionally substituted hydrocarbon radicals, such as lower alkyl groups, or suitable functional groups, such as free or functionally modified, for example etherified or esterified, hydroxyl or mercapto groups, free or substituted, including acylated, amino groups, nitro groups or optionally functionally modified carboxyl groups, such as for example the abovementioned groups.

Ethenyl radicals R which contain O-, S- or N-substituents are, above all, vinyl radicals substituted by etherified hydroxyl or etherified mercapto groups, and also by free or substituted amino groups of basic character, for example by the abovementioned groups of this nature, and which can optionally be substituted in the vinyl radical, for example by optionally substituted hydrocarbon radicals, such as those mentioned above. In such radicals, the O-, S- or N- substituent or the ethenyl grouping or both together can be incorporated in a cycloaliphatic C-radical; groups wherein both groupings form parts of such a radical are, for example, pyranyl or 2,3-dihydropyranyl groups.

Acyl radicals in acyl-substituted methyl groups are especially those of organic carboxylic acids, such as aliphatic, cycloaliphatic, cycloaliphatic-aliphatic, aromatic, araliphatic, heterocyclic or heterocyclic-aliphatic carboxylic acids, including formic acid, whilst functionally modified carboxyl groups for example represent acyl radicals of carbonic acid half-derivatives or cyano groups. Such groups are above all formyl, lower alkanoyl, optionally substituted benzoyl, lower alkoxycarbonyl or cyano groups. Correspondingly substituted methyl groups R are especially methyl radicals which are disubstituted by identical or different formyl, aliphatically, cycloaliphatically, aromatically or araliphatically substituted carbonyl or preferably functionally modified, such as esterified carboxyl or cyano groups, whereby two substituted carbonyl groups together with the methyl radical can also form parts of a cycloaliphatic grouping.

An acyl group Ac in particular represents an acyl radical of an organic carboxylic acid or of a carbonic acid half-derivative, the acyl radical being contained in a naturally occurring or biosynthetically, semi-synthetically or totally-synthetically preparable, preferably pharmacologically active, N-acyl derivative of 6-amino-penicillanic acid or 7-amino-cephalosporanic acid compounds, or represents an easily removable acyl radical, especially of a carbonic acid half-derivative.

An acyl radical Ac contained in pharmacologically active N-acyl derivatives of 6-amino-penicillanic acid or 7-aminocephalosporanic acid is, above all, a group of the formula

wherein $n$ represents O and $R^I$ denotes hydrogen or an optionally substituted cycloaliphatic or aromatic hydrocarbon radical, or an optionally substituted heterocyclic radical, preferably of aromatic character, a functionally modified, preferably etherified hydroxyl or mercapto group or an optionally substituted amino group, or wherein n represents 1, and $R^I$ represents hydrogen or an optionally substituted, aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character and/or a quaternary nitrogen atom, or represents an optionally functionally modified, preferably etherified or esterified, hydroxyl or mercapto group, an optionally functionally modified carboxyl group, an acyl group, an optionally substituted amino group or an azido group, and each of the radicals $R^{II}$ and $R^{III}$ is hydrogen, or wherein $n$ represents 1, $R^I$ represents an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably displays aromatic character, $R^{II}$ denotes an optionally functionally modified, preferably etherified, hydroxyl or mercapto group, an optionally substituted amino group, an optionally functionally modified carboxyl or sulfo group, an azido group or a halogen atom, and $R^{III}$ represents hydrogen, or wherein n represents 1, each of the radicals $R^I$ and $R^{II}$ denote a functionally modified, preferably etherified or esterified, hydroxyl group, or an optionally functionally modified carboxyl group, and $R^{III}$ represents hydrogen, or wherein n represents 1, $R^I$ denotes hydrogen or an optionally substituted aliphatic, cycloaliphatic, cycloaliphatic-aliphatic, aromatic or araliphatic hydrocarbon radical, and $R^{II}$ and $R^{III}$ together represent an optionally substituted aliphatic, cycloaliphatic, cycloaliphatic-aliphatic or araliphatic hydrocarbon radical bonded to the carbon atom by a double bond, or wherein n represents 1 and $R^I$ denotes an optionally substituted aliphatic, cycloaliphatic, cycloaliphatic-aliphatic, aromatic or araliphatic hyrocarbon radical or an optionally substituted heterocyclic or heterocyclic-aliphatic radical, wherein heterocyclic radicals preferably possess aromatic character, $R^{II}$ denotes an optionally substituted aliphatic, cycloaliphatic, cycloaliphatic-aliphatic, aromatic or araliphatic hydrocarbon radical and $R^{III}$ denotes hydrogen or an optionally substituted aliphatic, cycloaliphatic, cycloaliphatic-aliphatic, aromatic or araliphatic hydrocarbon radical.

In the abovementioned acyl groups of the formula Ia, for example, n represents O and $R^I$ represents hydrogen or a cycloalkyl group with 5–7 ring carbon atoms which is optionally substituted, for example in the 1-position by amino or by a sulphoamino group which is optionally in the salt form, for example alkali metal salt form, a phenyl, naphthyl or tetrahydronaphthyl group which is optionally substituted, preferably by hydroxyl, lower alkoxy, for example methoxy, and/or halogen, for example chlorine, a heterocyclic group which is optionally substituted, for example by lower alkyl and-/or phenyl groups, which can in turn carry substituents, such as halogen, for example chlorine, or an amino group which is preferably N-substituted, for example by an optionally substituted lower alkyl radical, such as a lower alkyl radical containing halogen, for example chlorine, or n represents 1 and $R^I$ represents a lower alkyl group which is optionally substituted, preferably by phenyloxy optionally substituted by halogen, such as chlorine, such as phenyloxy containing hydroxyl and/or halogen, for example chlorine, amino and/or carboxyl, a lower alkenyl group, a phenyl group which is optionally substituted, such as a phenyl group containing hydroxyl, halogen, for example chlorine and/or optionally substituted phenyloxy, a pyridyl, pyridinium, thienyl, 1-imidazolyl or 1-tetrazolyl group which is optionally substituted, for example by amino or aminomethyl, an optionally substituted lower alkoxy group, a phenyloxy group which is optionally substituted, for example by hydroxyl and/or halogen, such as chlorine, a lower alkylthio or lower alkenylthio group, an optionally substituted, for example lower alkyl-substituted, such as methyl-substituted, phenylthio, 2-imidazolylthio, 1,2,4-triazol-3-ylthio, 1,3,4-triazol-2-ylthio, 1,2,4-thiadiazol-3-ylthio, such as 5-methyl-1,2,4-thiadiazol3-ylthio, 1,3,4-thiadiazol-2-ylthio, such as 5-methyl-1,3,4-thiadiazol-2-ylthio, or 5-tetrazolylthio, such as 1-methyl-5-tetrazolylthio group, a halogen atom, especially chlorine or bromine atom, an optionally functionally modified carboxyl group, such as a lower alkoxycarbonyl group, a nitrile group, or a carbamoyl group which is optionally N-substituted, for example by phenyl, an optionally substituted lower alkanoyl or benzoyl group, or an azido group, and $R^{II}$ and $R^{III}$ represent hydrogen, or n represents 1, $R^I$ represents a phenyl or thienyl group which is optionally substituted, for example by hydroxyl and/or halogen, for example chlorine, and also represent a 1,4-cyclohexadienyl group, $R^{II}$ represents an optionally substituted amino group, for example optionally substituted carbamoylamino group or a sulphoamino group present in the salt form, for example alkali metal salt form, an azido group, a carboxyl group optionally present in the salt form, for example alkali metal salt form, or in the esterified form, a nitrile group, a sulfo group, an optionally substituted lower alkoxy or phenyloxy group, or a halogen atom, and $R^{III}$ represents hydrogen, or n represents 1, $R^I$ and $R^{II}$ each represent halogen, for example bromine, or lower alkoxycarbonyl, for example methoxycarbonyl, and $R^{III}$ represents hydrogen, or n represents 1, and each of the groups $R^I$, $R^{II}$ and $R^{III}$ represent lower alkyl, for example methyl.

Such acyl radicals Ac are, for example, formyl, cyclopentylcarbonyl, α-aminocyclopentylcarbonyl or α-aminocyclohexylcarbonyl (with an optionally substituted amino group, for example a sulphoamino group optionally present in the salt form, or an amino group substituted by an acyl radical which can preferably be split off easily, for example on treatment with an acid agent, such as trifluoroacetic acid, or with a chemical reducing agent, such as zinc in the presence of aqueous acetic acid, or by an acyl radical which can be converted into such a radical, preferably a suitable acyl radical of a carbonic acid half-ester, such as 2,2,2-trichloroethyloxycarbonyl, 2-bromoethoxycarbonyl, 2-iodoethoxycarbonyl, tert.-butoxycarbonyl or phenacyloxycarbonyl, or of a carbonic acid half-amide, such as carbamoyl or N-methylcarbamoyl), 2,6-dimethoxybenzoyl, tetrahydronaphthoyl, 2-methoxy-naphthoyl, 2-ethoxy-naphthoyl, benzyloxycarbonyl, hexahydrobenzyloxycarbonyl, 5-methyl-3-phenyl-4-isoxazolylcarbonyl, 3-(2-chlorophenyl)-5-methyl-4-isoxazolylcarbonyl, 3-(2,6-dichlorophenyl)-5-methyl-4-isoxazolylcarbonyl, 2-chloroethylaminocarbonyl, acetyl, propionyl, butyryl, hexanoyl, octanoyl, acrylyl, crotonoyl, 3-butenoyl, 2-pentenoyl, methoxyacetyl, methylthioacetyl, butylthioacetyl, allylthioacetyl, chloroacetyl, bromoacetyl, dibromoacetyl, 3-chloropropionyl, 3-bromopropionyl, aminoacetyl or 5-amino-5-carboxylvaleryl (with an amino group which is optionally substituted, for example as indicated, and/or a carboxyl group which is optionally functionally modified, and is, for example, in the salt form, such as the sodium salt form, or in the ester form, such as a lower alkyl ester form, for example methyl or ethyl ester form), azidoacetyl, carboxyacetyl, methoxycarbonylacetyl, ethoxycarbonylacetyl, bis-methoxycarbonylacetyl, N-phenylcarbamoylacetyl, cyanoacetyl, α-cyanopropionyl, 2-cyano-3,3-dimethylacrylyl, phenylacetyl, α-bromophenylacetyl, α-azidophenylacetyl, 3-chlorophenylacetyl, 4-aminomethylphenylacetyl, (with an amino group which is optionally substituted, for example as indicated), phenacylcarbonyl, phenyloxyacetyl, 4-trifluoromethylphenyloxyacetyl, benzyloxyacetyl, phenylthioacetyl, bromophenylthioacetyl, 2-phenyloxypropionyl, α-phenyloxyphenylacetyl, α-methoxyphenylacetyl, α-ethoxyphenylacetyl, α-methoxy-3,4-dichlorophenylacetyl, α-cyanophenylacetyl, phenylglycyl, 4-hydroxyphenylglycyl, 3-chloro-4-hydroxyphenylglycyl or 3,5-dichloro-4-hydroxyphenylglycyl (with an amino group which is optionally substituted, for example as indicated above), benzylthioacetyl, benzylthiopropionyl, α-carboxyphenylacetyl (with a carboxyl group which is optionally functionally modified, for example as indicated above), 3-phenylpropionyl, 3-(3-cyanophenyl)-propionyl, 4-(3-methoxyphenyl)-butyryl, 2-pyridylacetyl, 4-aminopyridiniumacetyl (optionally with an amino group which is substituted, for example as indicated above), 2-thienylacetyl, 2-tetrahydrothienylacetyl, α-carboxy-2-thienylacetyl or α-carboxy-3-thienylacetyl (optionally with a carboxyl group which is functionally modified, for example as indicated above), α-cyano-2-thienylacetyl, α-amino-2-thienylacetyl or α-amino-3-thienylacetyl (optionally with an amino group which is substituted, for example as indicated above), α-sulfo-phenylacetyl (in which the sulfo group may be functionally modified, e.g. as the carboxyl group), 3-thienylacetyl, 2-furylacetyl, 1-imidazolylacetyl, 1-tetrazolylacetyl, 3-methyl-2-imidazolylthioacetyl, 1,2,4-triazol-3-ylthioacetyl, 1,3,4-triazol-2-ylthioacetyl, 5-methyl-1,2,4-thiadiazol-3-ylthioacetyl, 5-methyl-1,3,4-thiadiazol-2-ylthioacetyl or 1-methyl-5-tetrazolylthioacetyl.

An easily removable acyl radical Ac, especially of a carbonic acid half-ester, is above all an acyl radical of a half-ester of carbonic acid which can be split off by reduction, for example by treatment with a chemical reducing agent, or by treatment with acid, for example with trifluoroacetic acid, such as a lower alkoxycarbonyl radical which preferably shows multiple branching in the α-position or is substituted by acylcarbonyl, especially benzoyl radicals, or substituted by halogen atoms in the β-position, for example tert.-butoxycarbonyl, tert.-pentoxycarbonyl, phenacyloxycarbonyl, 2,2,2-trichloroethoxycarbonyl or 2-iodoethoxycarbonyl or a radical which can be converted into the latter, such as 2-chloroethoxycarbonyl or 2-bromoethoxycarbonyl, and also preferably polycyclic cycloalkoxycarbonyl, for example adamantyloxycarbonyl, optionally substituted phenyl-lower alkoxycarbonyl, above all α-phenyl-lower alkoxycarbonyl, wherein the α-position preferably has several substituents, for example diphenylmethoxycarbonyl or α-4-biphenylyl-α-methylethoxycarbonyl, or furyl-lower alkoxycarbonyl, above all α-furyl-lower alkoxycarbonyl, for example furfuryloxycarbonyl.

A divalent acyl group formed by the two radicals $R_1^a$ and $R_1^b$ is, for example, the acyl radical of a lower alkanedicarboxylic acid or lower alkenedicarboxylic acid, such as succinyl, or of an o-aryldicarboxylic acid, such as phthaloyl.

A further divalent radical formed by the groups $R_1^a$ and $R_1^b$ is, for example, a 1,1-di-lower alkyl-4-oxo-2-aza-1,4-butylene radical which, especially in the 3-position, contains, for example, an optionally substituted phenyl or thienyl, for example 1,1-dimethyl-3-phenyl-4-oxo-2-aza-1,4-butylene radical.

An organic radical $R_2^A$ which together with the —C(=O)—O— grouping forms an esterified carboxyl group which can preferably be split easily, for example represents a 2-halogeno-lower alkyl radical $R_2^a$, wherein halogen has an atomic weight of above 19. Such a radical together with the —C(=O)—O— grouping forms an esterified carboxyl group which can easily be split on treatment with chemical reducing agents under neutral or weakly acid conditions, for example with zinc in the presence of aqueous acetic acid, or forms an esterified carboxyl group which can easily be converted into such a carboxyl group, and is, for example, 2,2,2-trichloroethyl, 2-chloroethyl, 2-bromoethyl or 2-iodoethyl.

A further group $R_2^A$, which together with the —C(=O)—O— grouping forms an esterified carboxyl group which can also be split easily on treatment with chemical reducing agents under neutral or weakly acid conditions, for example on treatment with zinc in the presence of aqueous acetic acid, is an arylcarbonylmethyl group $R_2^b$, wherein aryl especially represents an optionally substituted phenyl group, and preferably phenacyl.

The group $R_2^A$ can also represent the radical $R_2^c$, which denotes an arylmethyl group, wherein aryl especially represents a monocyclic, preferably substituted, aromatic hydrocarbon radical. Such a radical together with the —C(=O)—O— grouping forms an esterified carboxyl group which can easily be split on irradiation, preferably with ultraviolet light, under neutral or acid conditions. Such an aryl radical contains, as substituents, especially lower alkoxy, for example methoxy (which in the case of the preferred phenyl radical are above all in the 3-, 4- and/or 5-position), and/or above all nitro (in the case of the preferred phenyl radical, preferably in the 2-position). Such radicals $R_2^c$ are, above all, 3- or 4-methoxybenzyl, 3,5-dimethoxybenzyl, 2-nitrobenzyl or 4,5-dimethoxy-2-nitrobenzyl.

A group $R_2^A$ can also represent the radical $R_2^d$, which together with the —C(=O)—O— grouping forms an esterified carboxyl group which can easily be split under acid conditions, for example on treatment with trifluoroacetic acid or formic acid. Such a radical $R_2^d$ is above all a methyl group, which is polysubstituted by optionally substituted hydrocarbon radicals, such as lower alkyl, lower alkenyl and/or lower alkinyl, or is monosubstituted by a carbocyclic aryl group possessing electron-donating substituents or by a heterocyclic group of aromatic character possessing oxygen or sulphur atoms as a ring member, or $R_2^d$ denotes a ring member in a polycycloaliphatic hydrocarbon radical, or denotes the ring member which is in the α-position to the oxygen atom or sulphur atom in an oxacycloaliphatic or thiacycloaliphatic radical.

Preferred polysubstituted methyl groups $R_2^d$ are, for example, tert.-butyl, tert.-pentyl, 1,1-dimethyl-2-pro1,1-dimethyl-2-butinyl, benzhydryl, 4,4'-dimethoxybenzhydryl or 2-(4-biphenylyl)-2-propyl, whilst a methyl group $R_2^d$ containing the abovementioned substituted aryl or heterocyclic group is, for example, 3,4-dimethoxy-benzyl, or 2-furyl. A polycycloaliphatic hydrocarbon radical in which the methyl group $R_2^d$ represents a preferably triply branched ring member is, for example, adamantyl, such as 1-adamantyl, and an above-mentioned oxacycloaliphatic or thiacycloaliphatic radical $R_2^d$ is a 2-tetrahydrofuryl, 2-tetrahydropyranyl or 2,3-dihydro-2-pyranyl or corresponding sulphur analogues.

The radical $R_2^A$ can also represent a radical $R_2^e$, which together with the —C(=O)—O— grouping forms an esterified carboxyl group which can be split hydrolytically, for example under weakly basic or weakly acid conditions. Such a radical $R_2^e$ is preferably a radical which together with the —C(=O)—O— grouping forms an activated ester, such as nitrophenyl, for example 4-nitrophenyl or 2,4-dinitrophenyl, nitrophenyl-lower alkyl, for example 4-nitrobenzyl, polyhalogenophenyl, for example 2,4,6-trichlorophenyl or 2,3,4,5,6-pentachlorophenyl, and also cyanomethyl, as well as acylaminomethyl, for example phthaliminomethyl or succinyliminomethyl.

The group $R_2^A$ can also represent a radical $R_2^f$ which together with the carboxyl grouping —C(=O)—O— forms an esterified carboxyl group which can be split under hydrogenolytic conditions, and is, for example, an optionally stituted α-aryl-lower alkyl radical, such as benzyl, 4-methoxy-benzyl, 4-nitrobenzyl, benzhydryl or 4,4-dimethoxybenzhydryl.

The group $R_2^A$ can also represent a radical $R_2^g$ which together with the carboxyl grouping —C(=O)—O— forms an esterified carboxyl group which can be split under physiological conditions, above all lower alkanoyloxymethyl, for example acetoxymethyl.

A silyl radical or stannyl radical $R_2^A$ preferably contains optionally substituted aliphatic, cycloaliphatic, aromatic or araliphatic hydrocarbon radicals, such as lower alkyl, cycloalkyl, phenyl or phenyl-lower alkyl groups, and above all represents tri-lower alkylsilyl, for example trimethylsilyl, or tri-lower alkylstannyl, for example tri-n-butylstannyl.

An acyl radical which together with the —C(=O)—O— grouping forms a mixed anhydride group which can be split, preferably hydrolytically, is, for example, the acyl radical of one of the abovementioned organic carboxylic acids or carbonic acid half-derivatives, such as lower alkanoyl, for example ethyl, or lower alkoxycarbonyl, for example ethoxycarbonyl.

Salts are, in particular, those of the compounds of the formula I, in which $R_2$ represents hydrogen, or in which $R_1^a$, $R_1^b$ and/or R contain a free carboxyl group as substituent are above all metal salts or ammonium salts, such as alkali metal salts and alkaline earth metal salts, for example sodium, potassium, magnesium or calcium salts, as well as ammonium salts with ammonia or suitable organic amines, for which, above all, aliphatic, cycloaliphatic, cycloaliphaticaliphatic and araliphatic primary, secondary or tertiary monoamines, diamines or polyamines, as well as heterocyclic bases can be used to form salts, such amines being lower alkylamines, for example triethylamine, hydroxy-lower alkylamines, for example 2-hydroxyethylamine, bis-(2-hydroxyethyl)amine or tri-(2-hydroxyethyl)-amine, basic aliphatic esters of carboxylic acids, for example 4-aminobenzoic acid-2-diethylamino-ethyl ester, lower alkyleneamines, for example 1-ethylpiperidine, cycloalkylamines, for example bicyclohexylamine, or benzylamines, for example N,N'-dibenzylethylenediamine, and also bases of the pyridine type, for example pyridine, collidine or quinoline. Compounds of the formula I, in which, for example, $R_1^a$ and $R_1^b$ represent hydrogen or which possess a basic group in a radical $R_1^a$, $R_1^b$ and/or R, can also form acid addition salts, for example with inorganic acids, such as hydrochloric acid, sulphuric acid or phosphoric acid, or with suitable organic carboxylic acids or sulphonic acids, for example trifluoroacetic acid. Compounds of the formula I, wherein $R_2$ represents hydrogen or in which $R_1^a$, $R_1^b$ and/or R contain an acid grouping as substituent and in which $R_1^a$ and R $_1^b$ denote hydrogen, or which contain a basic group in a radical $R_1^a$, $R_1^b$ and/or R, can also be present in the form of an internal salt, that is to say in the form of the zwitter ion.

The compounds of the formula I, particularly those, in which $R_1^a$ represents an acyl radical occurring in pharmacologically active N-acyl derivatives of 6-amino-penam-3-carboxylic acid compounds or 7-amino-ceph-3-em-4-carboxylic acid compounds, and $R_1^b$ represents hydrogen, $R_2$ denotes hydrogen or an organic radical which can easily be split off under physiological conditions, and R has the above given meaning, demonstrate useful pharmacological properties, especially against micro-organisms, such as Gram-positive bacteria, for example *Staphylococcus aureus*, including penicillin-resistant bacteria of this type, and are useful, for example, in dilutions of about 10 γ/ml. against such microorganisms in the form of antibiotically active preparations.

The compounds of formula I represent primarily valuable intermediate products for the manufacture of new compounds having pharmacological properties; their conversion into such compounds will be described in more detail below.

Particularly valuable as intermediate products are compounds of formula I, wherein R represents (a) an at most bicyclic aromatic hydrocarbon radical, that is to say a phenyl or naphthyl radical, which possesses in at least one of the ortho- or para-positions or in positions which are equivalents to these hydroxyl, lower alkoxy, e.g. methoxy, and/or lower alkyl-thio, e.g. methylthio, furthermore amino and/or di-lower alkyl-amino, e.g. dimethylamino, as well as lower alkanoyloxy, e.g. acetyloxy, and which is optionally substituted further, with optionally present substituents denoting lower alkyl, e.g. methyl, hydroxy, lower alkoxy, e.g. methoxy, lower alkanoyloxy, e.g. acetyloxy, lower alkyl-thio, e.g. methylthio, trifluoromethyl, amino, di-lower alkyl-amino, e.g. dimethylamino, lower alkanoylamino, e.g. acetylamino, lower alkanoyl, e.g. acetyl, carboxyl, lower alkoxycarbonyl, e.g. methoxycarbonyl or ethoxycarbonyl, 2-halogeno-lower alkoxycarbonyl, e.g. 2,2,2-trichloroethoxycarbonyl, 2-bromoethoxycarbonyl or 2-iodoethoxycarbonyl, carbamoyl, cyano, sulpho or sulphamoyl and/or halogeno, e.g. fluoro, chloro or bromo, (b) an optionally substituted, at most bicyclic monooxacyclic, monothiacyclic or monoazacyclic radical of aromatic character, being bonded via a carbon atom and having an uneven number of ring members in the hetero-ring, such as an optionally substituted furyl, for example 2-furyl, benzofuryl, e.g. 2- or 3-benzofuryl, thienyl, for example 2- or 3-thienyl, benzothienyl, e.g. 3-benzothienyl, pyrryl, for example, 2- or 3-pyrryl, or indolyl, for example, 3-indolyl, wherein optionally present substituents denote lower alkyl, e.g. methyl, carboxymethyl, lower alkoxy-carbonylmethyl, e.g. methoxycarbonylmethyl or ethoxycarbonylmethyl, 2-halogeno-lower alkoxycarbonyl-methyl, e.g. 2,2,2-trichloroethoxycarbonylmethyl or 2-bromoethoxycarbonylmethyl, trifluoromethyl, hydroxyl, lower alkoxy, e.g. methoxy, lower alkanoyloxy, e.g. acetyloxy, lower alkylthio, e.g. methylthio, amino, di-lower alkylamino, e.g. dimethylamino, lower alkanoylamino, e.g. acetylamino, lower alkanoyl, e.g. acetyl, carboxyl, lower alkoxy-carbonyl, e.g. methoxycarbonyl or ethoxycarbonyl, 2-halogeno-lower alkoxycarbonyl, e.g. 2,2,2-trichloroethoxycarbonyl, 2-bromoethoxycarbonyl or 2-iodoethoxycarbonyl, carbamoyl, cyano, sulpho or sulphamoyl and/or halogeno, e.g. fluoro, chloro or bromo, or (c) a radical of formula $R_a(R_b)$CH—, wherein each of the groups $R_a$ and $R_b$ represents a formyl, lower alkanoyl, e.g. acetyl, lower alkoxycarbonyl e.g. methoxycarbonyl or ethoxycarbonoyl, or cyano, $R_1^a$ denotes hydrogen or an acyl radical contained in a naturally occurring or biosynthetically, semi-synthetically or totalsynthetically preparable, in particular pharmacologically active, such as highly active, N-acyl derivative of a 6-amino-penam-3-carboxylic acid compound or 7-amino-ceph-3-em-4-carboxylic acid compound, or an easily removable acyl radical of a carbonic acid half-derivative, especially of a carbonic acid half-ester, $R_1^b$ stands for hydrogen, and $R^2$ represents hydrogen or an organic radical $R_2^A$, which together with the —C(=O)—O— grouping forms an esterified carboxyl group which can easily be split on treatment with water, with an acid agent, with a chemical reducing agent under neutral or weakly acid conditions, or hydrolytically or hydrogenolytically, or an esterified carboxyl group which can easily be split under physiological conditions, or an esterified carboxyl group which can be converted into such group, for example tri-lower alkyl-silyl, e.g. trimethylsilyl, tert.-lower alkyl or tert.-lower alkenyl, e.g. tert.-butyl, 2-halogeno-lower alkyl, e.g. 2,2,2-trichloroethyl, 2-chloroethyl, 2-bromoethyl or 2-iodoethyl, optionally substituted diphenylmethyl, e.g. benzhydryl or 4,4'-dimethoxy-diphenylmethyl, phenacyl, 4-methoxybenzyl, 4-nitrobenzyl, or lower alkanoyloxymethyl, e.g. acetyloxymethyl, and also salts of such compounds having salt-forming groups.

In a compound of formula I, R above all represents a phenyl or naphthyl radical substituted in at least one of the ortho- or para-positions or in positions, which are equivalent thereto by hydroxyl, lower alkoxy, for example methoxy, lower alkyl-thio, e.g. methylthio, or lower alkanoyloxy, e.g. acetyloxy, whereby such residue may be further substituted, preferably in other positions, by hydroxy or lower alkoxy, e.g. methoxy, or furyl, e.g. 2-furyl, thienyl, e.g. 2-thienyl, pyrryl, e.g. 2-pyrryl, or indolyl, e.g. 3-indolyl, which radicals may be substituted by carboxy or lower alkoxy-carbonyl, e.g. methoxycarbonyl or ethoxy carbonyl, $R_1^a$ represents hydrogen or an acyl radical contained in naturally occurring or biosynthetically preparable N-acyl derivatives of 6-amino penam-3-carboxylic acid compounds or 7-amino-ceph-3-em-4-carboxylic acid compounds, such as an optionally substituted phenylacetyl or phenyloxyacetyl radical, and also an optionally substituted lower alkanoyl or lower alkenoyl radical, for example, 4-hydroxy-phenylacetyl, hexanoyl, octanoyl, 3-hexenoyl, 5-amino-5-carboxyvaleryl (optionally with protected carboxyl and/or amino group), n-butylmercaptoacetyl or allylmercaptoacetyl, and especially phenylacetyl or phenyloxyacetyl, an acyl radical occurring in highly active N-acyl derivatives of 6-amino-penam-3-carboxylic acid compounds or 7-amino-ceph-3-em-4-carboxylic acid compounds, such as formyl, 2-chloroethylcarbamoyl, cyanoacetyl or 2-thienylacetyl, especially phenylglycyl, wherein phenyl represents optionally hydroxyl-substituted and/or halogen substituted, for example chlorine substituted phenyl, for example phenyl, or 3- or 4-hydroxy- or 3,5-dichloro-4-hydroxyphenyl, and wherein the amino group is optionally substituted and, for example, represents a sulphoamino group, optionally present in the salt form, or an amino group which is substituted by an optionally substituted carbamoyl group, such as an optionally substituted ureidocarbonyl group, for example ureidocarbonyl or $N^3$-trichloromethylureidocarbonyl, or by an optionally substituted guanidinocarbonyl group, for example guanidinocarbonyl, or by an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such an acyl radical, preferably a suitable acyl radical of a carbonic acid half-ester, such as 2,2,2-trichloroethyloxycarbonyl, 2-chloroethoxycarbonyl, 2-bromoethoxycarbonyl, 2-iodoethoxycarbonyl, tert.-butoxycarbonyl or phenacyloxycarbonyl, or of a carbonic acid half-amide, such as carbamoyl or N-methylcarbamoyl, also thienylglycyl, such as 2-thienylglycyl, (optionally with an amino group which is substituted, for example as indicated above), or 1-amino-cyclohexylcarbonyl (optionally with an amino group which is substituted, for example as indicated above), and also α-carboxyphenylacetyl or α-carboxy-2-thienylacetyl (optionally with a functionally modified carboxyl group, for example a carboxyl group present in the salt form, such as sodium salt form, or in the ester form, such as lower alkyl ester form), or α-sulfophenylacetyl or α-sulfo-2-thienylacetyl, (in which sulfo may be functionally modified, e.g. in salt, for example, sodium salt form), or an acyl radical of a carbonic acid half-ester which can be split off easily, especially under acid conditions, for example on treatment with trifluoroacetic acid, or reductively with zinc in the presence of aqueous acetic acid, such as tert.-butoxycarbonyl, phenacylcarbonyl 2,2,2-trichloroethoxycarbonyl or 2-iodoethoxycarbonyl, or 2-chloroethoxycarbonyl- or 2-bromoethoxycarbonyl, which can be easily converted into the latter, and $R_1^b$ represents hydrogen and $R_2$ represents hydrogen or a radical $R_2^A$, which together with the —C(=O)—O— grouping forms an esterified carboxyl group which can be split easily hydrogenolytically, on treatment with a chemical reducing agent under neutral or weakly acid conditions, with an acid agent or hydrolytically, preferably under weakly basic conditions or under physiological conditions, and above all represents a methyl which is polysubstituted by optionally substituted hydrocarbon radicals, such as lower alkyl radicals, especially tert.-butyl or diphenylmethyl, and 2,2,2-trichloroethyl, 2-iodoethyl, and 2-chloroethyl or 2-bromoethyl which can easily be converted into 2-iodoethyl, or phenacyl, as well as 4-methoxybenzyl or 4-nitrobenzyl, furthermore lower alkanoyloxymethyl, e.g. acetyloxymethyl.

The invention above all relates to compounds of the formula

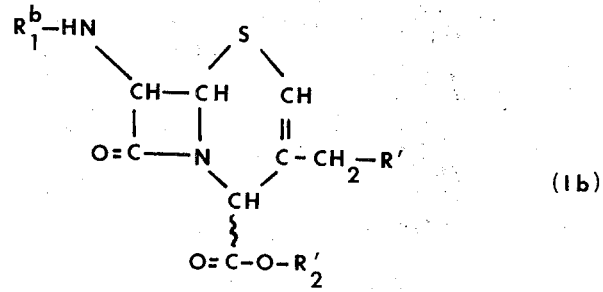

(Ib)

in which R' is 2- or 4-hydroxy-phenyl, 2,4-, 2,5- or 3,4-dihydroxy-phenyl, 2- or 4-lower alkoxy-phenyl, e.g. 2- or 4-methoxy-phenyl, 2,4-, 2,5- or 3,4-lower alkoxy phenyl, e.g. 2,4-, 2,5- or 3,4-dimethoxy-phenyl, 2- or 4-lower alkanoyloxy-phenyl, e.g. 2- or 4-acetyloxyphenyl, 4-lower alkyl-thio-phenyl, e.g. 4-methylthio-phenyl, 2-furyl, 5-carboxy-2-furyl, 5-lower alkoxycarbonyl-2-furyl, e.g. 5-methoxycarbonyl-2-furyl, 2-thienyl, 2-pyrryl, 5-carboxy-2-pyrryl or 5-loweralkoxy-carbonyl-2-pyrryl, e.g. 5-methoxycarbonyl-2-pyrryl, and in which R₁ is hydrogen or an acyl residue of the formula

in which Ar is phenyl, 3- or 4-hydroxy-phenyl, 3-chloro-4-hydroxy-phenyl, 3,5-dichloro-4-hydroxy-phenyl or 2-thienyl and $R_3$ represents hydrogen or amino, as well as acylated amino, in which acyl is preferably the acyl residue of a carbonic acid semiderivative, such as semi-ester or semi-amide, particularly an acyl residue of this type easily replaceable by hydrogen or convertible into such acyl residue, inter alia, tert.-lower alkoxy-carbonylamino, e.g. tert.-butyloxycarbonylamino, 2-halogeno-lower alkoxycarbonylamino, e.g. 2,2,2-tri-chloroethoxycarbonylamino, 2-chloroethoxycarbonylamino, 2-bromoethoxycarbonylamino or 2-iodoethoxycarbonylamino, furthermore guanylureido, as well as sulfoamino, or represents carboxyl or sulfo, and R$_2$ is hydrogen or an organic residue which together with the carboxyl grouping —C(=O)—O— forms an esterified carboxyl group easily splittable under mild or physiological conditions, or capable of being converted into such group, such as tert.-lower alkyl, e.g. tert.-butyl, 2-halogeno-lower alkyl, e.g. 2,2,2-trichloroethyl, 2-chloroethyl, 2-bromoethyl or 2-iodoethyl, phenacyl, benzhydryl, 4,4'-dimethoxy-diphenylmethyl, or lower alkanoyloxymethyl, e.g. acetyloxymethyl, or salts of such compounds having salt-forming properties.

The new compounds of the present invention are obtained in excellent yields if in a 7-N-$R_1^A$-N-$R_1^b$-amino)-3-X-methyl-ceph-2-em-4-carboxylic acid compound of formula

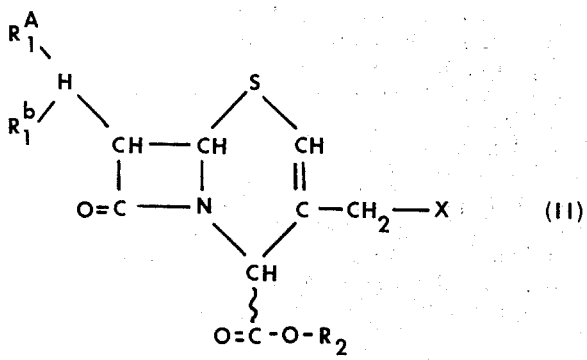

wherein $R_1^A$, $R_1^b$ and $R_2$ have the abovementioned meanings, whereby $R_1^A$ and $R_1^b$ together may also represent a bivalent amino protecting group, and X represents a free or esterified hydroxyl group, the methylene group —CH$_2$— in the 3-position of the ceph-2-em ring is C-nucleophilically substituted, with removal of the group X, by means of an organic C-nucleophilic compound of formula H-R (III), wherein R has the abovementioned significance, and, if desired, an amino protective groups $R_1^A$ and/or $R_1^b$ in a compound obtainable according to the process is removed and replaced by hydrogen or converted into another amino protective group, and/or, if desired, a resulting compound is converted into another compound of the formula I, and/or if desired, a compound obtainable according to the process, having a salt-forming group, is converted into a salt, or a resulting salt is converted into the free compound or into another salt, and/or, if desired, an isomer mixture obtainable according to the process is separated into the individual isomers.

In a starting material of formula II, an esterified hydroxyl group X can be esterified by an inorganic or organic acid, and the latter can, for example, be a strong mineral acid, above all a hydrohalic acid, for example hydrochloric, hydrobromic or hydriodic acid, and the group X in particular represents a halogen atom, preferably having an atomic weight of above 19, that is to say a chlorine, bromine or iodine atom.

An organic acid which esterifies the hydroxyl group is an appropriate carboxylic acid or sulphonic acid and is an aliphatic (including formic acid), cycloaliphatic, cycloaliphatic-aliphatic, aromatic, araliphatic, heterocyclic or heterocyclic-aliphatic carboxylic or sulphonic acid, or a carbonic acid half-derivative.

Thus, an esterified hydroxyl group X can represent an optionally substituted lower alkanoyloxy radical, especially the acetoxy radical, and above all a halogeno-lower alkanoyloxy radical, especially a halogenoacetoxy radical, such as the trifluoroacetoxy, as well as the dichloroacetoxy, furthermore the formyloxy radical, but can also represent an optionally substituted lower alkylsulphonyloxy, for example, methylsulphonyloxy, radical or an optionally substituted phenylsulphonyloxy, for example p-toluenesulphonyloxy, radical.

The starting material of formula II can be used in the form of the free carboxylic acids, that is to say $R_2$ usually represents hydrogen; it is however also possible to use compounds of formula II, in which $R_2$ is different from hydrogen and for example represents a radical $R_a^A$, which under the reaction conditions, for example in the presence of a Lewis acid which is optionally to be used, forms a stable or splittable protected, especially esterified carboxyl group with the —C(=O)—O— grouping.

Free functional groups which do not participate in the reaction, for example free hydroxyl, mercapto and/or amino groups, can be protected in the starting substances, where necessary, in a manner which is in itself known, for example only temporarily for example by acylation, furthermore by silylation, and can, if desired, be liberated again, in a manner which is in itself known, during the reaction or after it has taken place.

The compounds of formula III are C-nucleophilic compounds which in the radical R possess at least one hydrogen atom and in which at least one carbon atom is capable of electron enrichment and possesses an electron excess in the transition state (that is to say under the reaction conditions); this electron excess can for example be stabilised by one or more groupings which favour an electrophilic substitution. These are especially compounds with one or more double bonds which contain O-, S- or N-groupings, these being capable of stabilising the electron excess present on at least one carbon atom, or compounds with a methylene group activated by at least one carbonyl or one functionally modified carboxyl grouping.

Such C-nucleophilic compounds are carbocyclic aromatic compounds containing suitable O-, S- or N- substituents, as well as O-, S- or N-heterocyclic compounds of aromatic character with an uneven number of ring members in the heteroring, or ethene compounds containing suitable O-, S- or N-substituents, which may be connected to the ethene grouping via one or more double bonds and also methane compounds possessing acyl groups of functionally modified carboxyl groups, preferably two such radicals.

Above all, compounds of formula III represent preferably monocyclic or bicyclic, as well as polycyclic, aromatic hydrocarbons, substituted by O-, S- or N-substituents with the properties described above, especially by free or functionally modified, above all etherified, as well as esterified hydroxyl as well as mercapto groups, furthermore by free or substituted amino groups of basic or non-basic character, for example, by the abovementioned groups of this nature, above all by hydroxyl or lower alkoxy groups, as well as by lower alkanoyloxy groups, furthermore by lower alkyl-thio groups, and also be free amino or di-lower alkylamino groups, especially correspondingly substituted benzene, as well as naphthalene or biphenyl compounds, and also anthracene, phenathrene or fluorene compounds, it being possible for such compounds to be substituted further, for example as indicated.

O-, S- or N-heterocyclic compounds of formula III are above all monocyclic or bicyclic, as well as polycyclic, oxacyclic, thiacyclic or azacyclic compounds of aromatic character, wherein the hetero-ring possesses an uneven number of ring members, and which can optionally be substituted, for example as indicated. Such compounds are, for example, optionally substituted furane, thiophene, pyrrole, benzofurane, benzothiophene or indole compounds.

Ethene compounds containing O-, S- or N- groups are above all O- or S-enol compounds or enamine compounds in which the vinyl grouping preferably contains free or etherified or esterified hydroxyl groups or mercapto groups, or free or substituted amino groups of basic character, as substituents, and can optionally be substituted, for example as indicated above. In such compounds, the O-, S- and N- groupings or the ethene grouping connected thereto or both together can represent part of a cycloaliphatic ring; compounds wherein both groupings represent parts of a cycloaliphatic ring are, for example, pyrane or 2,3-dihydropyrane. Further, the vinyl grouping can also be part of a system of conjugated double bonds.

In methane compounds of formula III possessing acyl groups or functionally modified carboxyl groups, the acyl radicals and functionally modified carboxyl groups for example have the abovementioned meanings; such compounds are malondialdehyde, acylacetic acid ester, cyanoacetic acid ester, 1,3-diketone, malonic acid ester or malodinitrile compounds, whereby among the 1,3-diketones those of cycloaliphatic nature are also to be understood.

Depending on the nature of the radical X in the starting material of formula II and the C-nucleophilic compound of formula III, and their method of use, the process according to the invention can be carried out in the presence or absence of additional reagents which influence the reaction.

If, for example, the group X represents a reactive hydroxyl group esterified by a strong organic acid, above all an acyloxy group, wherein the acyl radical denotes the corresponding radical of a strong organic carboxylic acid, having no or at most weak nucleophilic properties, such as of formic acid, or preferably of a strong lower alkanecarboxylic acid, such as a halogenoacetic acid, above all trifluoroacetic acid, or the acyl radical of a strong organic sulphonic acid, such as of a lower alkanesulphonic acid, for example of methanesulphonic acid, or of an arylsulphonic acid, for example of p-toluenesulphonic acid, the reaction can be carried out in the absence of additional reagents.

If starting substances of formula II are used, wherein X generally denotes a free hydroxyl group or a hydroxyl group esterified by any type of organic carboxylic or sulphonic acid, that is to say also a hydroxyl group esterified by a relatively weak acid, such as a weak lower alkanecarboxylic acid, for example acetic, propionic or pivalic acid, or an arylcarboxylic acid, for example benzoic acid, that is to say wherein X, apart from a free hydroxyl group, also denotes a lower alkanoyloxy, especially acetoxy, as well as propionyloxy or pivaloyloxy, group, or an aroyloxy, for example benzoyloxy, group, the reaction of such a starting material with the organic C-nucleophilic compound of formula III is preferably carried out in the presence of an optionally protonic Lewis acid. Such reagents are above all, for example, strong, non-nucleophilic or only weakly nucleophilic, inorganic acids, such as phosphoric acid, preferably in the form of polyphosphoric acid, fluoboric acid or perchloric acid, the latter, for example, together with an organic carboxylic acid, such as an optionally substituted lower alkanecarboxylic acid, preferably acetic acid, and also sulphuric acid. Preferred protonic Lewis acids are strong, non-nucleophilic or only weakly nucleophilic, organic carboxylic acids, such as lower alkanecarboxylic acids which are optionally suitably substituted, for example by halogen atoms or cyano groups, such as formic acid, halogenated lower alkanecarboxylic acids, which preferably possess 2 or more halogen atoms in the α- position, for example dichloroacetic acid and above all trifluoroacetic acid, cyanoacetic acid, and also strong non-nucleophilic or only weakly nucleophilic organic sulphonic acids, such as lower alkanesulphonic acid, for example methanesulphonic acid, or benzenesulphonic acid which is optionally substituted, for example by lower alkyl groups, for example p-toluenesulphonic acid.

Non-protonic Lewis acids which at most display only slight nucleophilic properties, are above all non-nucleophilic or only weakly nucleophilic halides of Lewis acid character, such as boron halides, for example boron trifluoride, boron trichloride or boron tribromide, it also being possible, for example, for boron trifluoride, to be used as the etherate, for example with diethyl ether, aluminium halides, for example aluminium chloride, or tin-IV halides, for example tin-IV chloride.

Instead of non-protonic Lewis acids, iodine can also be used in the abovementioned reaction.

In the above process variant, according to which the reaction is carried out in the presence of a protonic Lewis acid, easily protonisable groups in the starting substances of formulae II and III are preferably present in a non-protonisable or only difficult-to-protonise form. Easily protonisable groups are, for example, basic amino groups; these can for example be in the form of acylamino groups, amongst others also those which can subsequently be split easily, for example by reduction or on treatment with suitable acids, for example in the form of an appropriate 2-halogeno-lower alkoxycarbonylamino group, such as 2,2,2-trichloroethoxycarbonyl-amino or 2-iodoethoxycarbonyl-amino group or of a group easily convertible into the latter, such as 2-chloroethoxycarbonyl-amino or 2-bromoethoxycarbonyl-amino, or of a tert.-lower alkoxycarbonylamino or tert.-lower alkenyloxycarbonylamino group, e.g. tert.-butyloxycarbonylamino, of a tritylamino group, or of an organic silylamino group, e.g. trimethylsilyl group.

If starting substances of formula III, apart from containing an easily protonisable substituent, such as for example a basic amino group, also contain a further substituent which assists the nucleophilic character of the compound of formula III, for example an etherified hydroxyl group, the reaction can also be carried out without the temporary protection of the easily protonisable group in the form of a group which can only be protonised with difficulty.

If the group X represents a hydroxyl group esterified by a strong inorganic acid, expecially a hydrohalic acid, and if X above all denotes a halogen atom with an atom weight of above 19, that is to say a chlorine or iodine atom and especially a bromine atom, the reaction is carried in the presence of agents which absorb halogen ions, such as silver ions, for example in the form of silver acetate.

Surprisingly, the reaction takes place under very mild conditions, even if only weak C-nucleophilic compounds of formula III are employed. It can be carried out in the absence or presence of a solvent or diluent, and suitable reagents, such as for example trifluoroacetic acid, can also be used as solvents or diluents. Furthermore, for example, optionally substituted hydrocarbons, such as halogen- or cyano-containing lower aliphatic, cycloaliphatic or aromatic hydrocarbons, for example, hexane, methylene chloride, chloroform, acetonitrile, cyclohexane, benzene or toluene, can be employed as optional additional inert solvents or diluents. The process is carried out with cooling, at room temperature or with warming, preferably in a temperature interval of about −30°C to about +100°C, if necessary, in a closed vessel and/or in an inert gas atmosphere, for example nitrogen atmosphere.

In the process of this invention free functional groups, which do not participate in the reaction, may, if desired or necessary, be protected temporarily in known manner, free hydroxy, mercapto and/or amino groups, for example, by acylation, tritylation or silylation and free carboxyl groups, for example, by esterification (silylation included), and may be liberated, if desired, during or after the reaction in a manner known per se.

Advantageously, in the process of this invention starting materials of the formula II are used, in which X is hydroxy or acetyloxy, and reacted with the compound of the formula III in the presence of an optionally protonic Lewis acid, especially a strong organic carboxylic acid having no or at most weak-nucleophilic properties and above all trifluoroacetic acid, or starting materials of the formula II are employed, in which X is an acyloxy group, wherein acyl represents the acyl residue of a strong, non- or at most weakly nucleophilic organic carboxylic acid and above all of trifluoroacetic acid, and is reacted with the compound of the formula III, and, if desired, the optional steps are carried out.

In a resulting compound amino-protective groups $R_1^A$ and/or $R_1^b$ may be removed according to per se known methods.

Thus, a triarylmethyl protecting group $R_1^A$ of the amino group may be split off under acidic conditions, for example, in the presence of an inorganic acid, such as hydrochloric acid, and replaced by hydrogen.

In a resulting compound, an acyl group Ac which represents the amino protective group $R_1^A$ and/or $R_1^b$ can be removed in a manner which is in itself known.

Thus, an easily removable acyl group of a carbonic acid half-ester may be removed under mild conditions, which do not attack the remainder of the molecule, a tert.-butyloxycarbonyl group, for example by treatment with trifluoroacetic acid (optionally under the reaction conditions), and a 2,2,2-trichloroethoxycarbonyl, 2-iodoethoxycarbonyl or phenacyloxycarbonyl group, for example, by treatment with a suitable reducing metal or a reducing metal compound, for example zinc or a chromium-II salt, such as chromium-II chloride or acetate, advantageously in the presence of a hydrogen-releasing agent which together with the metal or the metal compound generates nascent hydrogen, preferably in the presence of aqueous acetic acid.

An acyl group $R_1^A$ and/or $R_1^b$ may, for example, be replaced by treatment with an acid reagent, particularly a strong organic sulfonic acid, such as an aromatic sulfonic acid, e.g. p-toluene sulfonic acid, in the presence of an alcohol, particularly a lower alkanol, e.g. methanol or ethanol.

It is furthermore possible, in a resulting compound of the formula I, wherein a carboxyl group $-C(=O)-O-R_2$ preferably represents a carboxyl group which is protected, for example by esterification, including by silylation or stannylation, for example by reaction with a suitable organic halogenosilicon or halogeno-tin-IV compound, such as trimethylchlorosilane or tri-n-butyl-tin chloride, to remove a suitable acyl group $R_1^A$ or $R_1^b$, wherein free functional groups which may be present are optionally protected, by treatment with an imide-halide-forming agent, reaction of the resulting imide-halide with an alcohol and splitting of the imino-ether formed, and a carboxyl group protected, for example, by an organic silyl radical can already be liberated in the course of the reaction, for example during the treatment with an alcohol.

Imide-halide-forming agents, in which halogen is bonded to an electrophilic central atom, are above all acid halides, such as acid bromides and especially acid chlorides. These are, above all, acid halides of inorganic acids, above all of phosphorus-containing acids, such as phosphorus oxyhalides, phosphorus trihalides and especially phosphorus pentahalides, for example phosphorus oxychloride, phosphorus trichloride and above all phosphorus pentachloride, as well as pyrocatechyl-phosphorus trichloride, as well as acid halides, especially chlorides, of sulphur-containing acids or of carboxylic acids, such as thionyl chloride, phosgene or oxalyl chloride.

The reaction with one of the imide-halide-forming agents mentioned is preferably carried out in the presence of a suitable base, especially an organic base, above all a tertiary amine, for example a tertiary aliphatic monoamine or diamine, such as a tri-lower alkylamine, for example trimethylamine, triethylamine or ethyldiisopropylamine, or of an N,N,N',N'-tetra-lower alkyl-lower alkylenediamine, for example N,N,N',N'-tetramethyl-1,5-pentylene-diamine or N,N,N',N'-tetramethyl-1,6-hexylenediamine, a monocyclic or bicyclic monoamine or diamine, such as a N-substituted, for example N-lower alkylated, alkyleneamine, azaalkyleneamine, or oxaalkyleneamine, for example N-methyl-piperidine or N-methyl-morpholine, or 2,3,4,6,7,8-hexahydro-pyrrolo[1,2-α] pyrimidine (diazabicyclononene; DBN), or a tertiary aromatic amine, such as a di-lower alkylaniline, for example N,N-dimethylaniline, or above all a tertiary heterocyclic, monocyclic or bicyclic, base, such as quinoline or isoquinoline, especially pyridine. In this reaction, approximately equimolar amounts of the imide-halide-forming agent and of the base can be used; the latter can, however, also be present in excess or in less than equivalent amounts, for example in about 0.2-fold to about 1-fold amount, or in up to about 10-fold excess, especially about 3-5-fold excess.

The reaction with the imide-halide forming agent is preferably carried out with cooling, for example at temperatures of about −50°C to about +10°C, but the process can also be carried out at higher temperatures, that is to say, for example, up to about 75°C, if the stability of the starting substances and the stability of the products permit a higher temperature.

The imide-halide product, which is usually further processed without isolation, is reacted, in accordance with the process, with an alcohol, preferably in the presence of one of the abovementioned bases, to give the iminoether. Suitable alcohols are, for example, aliphatic as well as araliphatic alcohols, above all optionally substituted, such as halogenated, for example chlorinated lower alkanols, or lower alkanols possessing additional hydroxyl groups, for example ethanol, n-propanol, isopropanol or n-butanol, especially methanol, as well as 2,2,2-trichloroethanol, and also optionally substituted phenyl-lower alkanols, such as benzyl alcohol. Usually an excess, for example an up to 100-fold excess, of the alcohol is employed, and the process is preferably carried out with cooling, for example at temperatures of about −50°C to about 10°C.

The iminoether product can advantageously be split without isolation. The splitting of the iminoether can be achieved by treatment with a suitable hydroxy compound. For this, water, or an aqueous mixture of an organic solvent, such as an alcohol, especially a lower alkanol, for example methanol, is preferably used. The process is usually carried out in an acid medium, for example at a pH-value of about 1 to about 5, and this value can be adjusted, if necessary, by adding a basic agent, such as an aqueous alkali metal hydroxide, for example sodium hydroxide or potassium hydroxide, or an acid, for example a mineral acid or organic acid, such as hydrochloric acid, sulphuric acid, phosphoric acid, fluoboric acid, trifluoroacetic acid or p-toluenesulphonic acid.

The three-stage process, described above, for splitting off an acyl group is advantageously carried out without isolation of the imide-halide and iminoether intermediate products, usually in the presence of an organic solvent which is inert towards the reactants, such as an optionally halogenated hydrocarbon, for example methylene chloride, and/or in an inert gas atmosphere, such as a nitrogen atmosphere.

If the imide-halide intermediate product obtainable according to the above process, instead of being reacted with an alcohol, is reacted with a salt, such as an alkali metal salt, of a carboxylic acid, especially of a sterically hindered carboxylic acid, a N,N-diacylamino compound of the formula I is obtained, wherein $R_1^a$ and $R_1^b$ represent acyl groups.

In a compound of the formula I wherein both radicals $R_1^a$ and $R_1^b$ represent acyl groups, one of these groups, preferably the group which is less sterically hindered, can be removed selectively, for example by hydrolysis or aminolysis.

In a compound of the formula I, wherein $R_1^A$ and $R_b^1$ together with the nitrogen atom represent a phthalimido group, this group can be converted into the free amino group, for example by hydrazinolysis, that is to say on treating such a compound with hydrazine.

Certain acyl radicals of an acylamino grouping in compounds obtainable according to the invention, especially the 5-amino-5-carboxyvaleryl radical, can also be split off by treatment with a nitrosylating agent, such as nitrosyl chloride, with a carbocyclic arene-diazonium salt, such as benzenediazonium chloride, or with an agent which releases positive halogen, such as a N-halogeno-amide or N-halogenoimide, for example N-bromosuccinimide, preferably in a suitable solvent or solvent mixture, such as formic acid together with a nitro-lower alkane or cyano-lower alkane, mixing the reaction product with a hydroxyl-containing agent, such as water or a lower alkanol, for example methanol, and, where necessary, working up the free amino compound according to methods which are in themselves known.

A formyl group $R_1^A$ can also be removed by treatment with an acid agent, for example p-toluenesulphonic acid or hydrochloric acid, the latter in the presence of water and optionally of an organic solvent, e.g. dioxane, a weakly basic agent, for example dilute ammonia, or a decarbonylating agent, for example tris-(triphenylphosphine)-rhodium chloride.

A resulting compound of the formula I may be converted into another compound of such formula.

In a compound of the formula I, wherein $R_1^a$ and $R_1^b$ represent hydrogen, the free amino group can be acylated according to acylation methods which are in themselves known, for example by treatment with carboxylic acids or reactive acid derivatives thereof, such as halides, for example fluorides or chlorides, or anhydrides (by which there are also to be understood the internal anhydrides of carboxylic acids, that is to say ketenes, or of carbamic acids or thiocarbamic acids, that is to say isocyanates or isothiocyanates, or mixed anhydrides, such as those which can, for example, be formed with chloroformic acid lower alkyl esters, such as chloroformic acid ethyl esters, or trichloroacetic acid chloride), or activated esters, or with substituted formimino derivatives, such as substituted N,N-dimethylchloroformimino derivatives, or a N-substituted N,N-diacylamine, such as a N,N-diacylated aniline, the reaction being carried out in the presence of suitable condensation agents if necessary, for example in the presence of carbodiimides, such as dicyclohexylcarbodiimide, when using acids, or in the presence of, for example, basic agents, such as triethylamine or pyridine, when using reactive acid derivatives. One may use in the acylation procedures salts, such as ammonium salts, e.g. tri-lower alkyl-ammonium salts, of the compounds of the formula I, in which $R_2$ is hydrogen.

An acyl group can also be introduced by reacting a compound of the formula I, wherein $R_1^a$ and $R_1^b$ represent hydrogen, with an aldehyde, such as an aliphatic, aromatic or araliphatic aldehyde, acylating the resulting Schiff's base, for example according to the abovementioned methods, and hydrolysing the acylated product, preferably in a neutral or weakly acid medium.

It is also possible to introduce an acyl group in stages. Thus it is, for example, possible to introduce a halogeno-lower alkanoyl group, for example bromoacetyl group, or, for example by treatment with a carbonic acid dihalide, such as phosgene, to introduce a halogenocarbonyl group, for example a chlorocarbonyl group, into a compound of the formula I having a free amino group, and to react a N-(halogeno-lower alkanoyl)-amino compound or N-(halogenocarbonyl)-amino compound, thus obtainable, with suitable exchange reagents, such as basic compounds, for example tetrazole, thio compounds, for example 2-mercapto-1-methyl imidazole, or metal salts, for example sodium azide, or alcohols, such as lower alkanols, for example tert.-butanol, and thus to obtain substituted N-lower alkanoylamino or with N-hydroxycarbonylamino compounds. In both reaction participants, free functional groups may be temporarily protected in a known manner during the acylation reaction and may be liberated after the acylation in a known manner.

The acylation can also be effected by replacing an already existing acyl group by a different, preferably sterically hindered, acyl group, for example according to the process described above, by preparing the imidehalide compound, treating this with a salt of an acid, and hydrolytically splitting off one of the acyl groups present in the product thus obtainable, usually the less sterically hindered acyl group.

In a compound of the formula I, wherein $R_1^a$ and $R_1^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a maner which is in itself known, for example by treatment with a suitable silylating agent, such as a tri-lower alkylsilyl halide, for example trimethyl-silyl chloride, or an optionally N-mono-lower alkylated, N,N-di-lower alkylated, N-tri-lower alkylsilylated or N-lower alkyl-N-tri-lower alkylsilylated N-(tri-lower alkyl-silyl)-amine (see, for example, British Pat. No. 1,073,530) or with a suitable stannylating agent, such as a bis-(tri-lower alkyl-tin)- oxide, for example bis-(tri-n-butyl-tin)-oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound, or a tri-lower alkyl-tin halide, for example tri-n-butyl-tin chloride (see, for example, Netherlands published Specification No. 67/17107.)

In amino protective groups $R_1^A$ and/or $R_1^b$, substituents may be introduced, split off and/or converted into each other according to known methods. Thus, in a resulting compound of the formula I, in which $R_1^b$ is hydrogen and $R_1^a$ is an optionally α-substituted N-unsubstituted glycyl, such as α-phenylglycyl group, the free amino group may be converted according to per se known methods into a substituted amino group, for example, by treatment with sulfur trioxide, e.g. as sulfur trioxide-triethylamine-complex, into a sulfoamino group, or with 4-guanylsemicarbazide or an acid addition salt thereof in the presence of a nitrosating agent, such as nitrous acid or sodium nitrate, into a guanylureido group. In a resulting compound of the above type, the free amino group may be protected, for example, by acylation, e.g. by introduction of the acyl residue of a carbonic acid half-derivative, such as half-ester, or a suitably protected, e.g. acylated amino group, such as tert.-butyloxycarbonylamino, 2,2,2-trichloroethoxycarbonylamino or 2-iodoethoxycarbonylamino, may be liberated; the above acylation and liberation reactions may be carried out according to known methods, such as those described above. Furthermore, it is possible to react a compound of the formula I, wherein $R_1^a$ represents a glycyl group which is optionally substituted in the α-position, such as phenylglycyl, and $R_1^b$ represents hydrogen, with a lower alkanone, for example acetone, and thus to obtain compounds of the formula I, wherein $R_1^A$ and $R_1^b$ together represent a 1,1-di-lower alkyl-4-oxo-2-aza-1,4-butylene which is optionally substituted in the 3-position.

In a compound of the formula I, obtainable according to the process, which possesses a group of the formula $-C(=O)-O-R_2$, wherein $R_2$ represents hydrogen, the free carboxyl group can be esterified, in a manner which is in itself known, to give a protective carboxyl group, for example by treatment with a diazo compound, such as a diazo-lower alkane, for example diazomethane or diazoethane, or a phenyldiazo-lower alkane, for example phenyldiazomethane or diphenyldiazomethane, or by reaction with an alcohol which is suitable for esterification, in the presence of an esterifying agent, such as a carbodiimide, for example dicyclohexylcarbodiimide, as well as carbonyldiimidazole, or according to any other known and suitable esterification process, such as reaction of a salt of the acid with a reactive ester of an alcohol and a strong inorganic acid, as well as a strong organic sulphonic acid. Furthermore, it is possible to convert acid halides, such as acid chloride (manufactured, for example, by treatment with oxalyl chloride), activated esters (formed, for example, with N-hydroxy-nitrogen compounds) or mixed anhydrides (formed, for example, with halogenoformic acid lower alkyl esters, such as chloroformic acid ethyl ester, or with halogenoacetic acid halides, such as trichloroacetic acid chloride) into an esterified carboxyl group by reaction with alcohols, optionally in the presence of a base, such as pyridine.

Mixed anhydrides can be manufactured by reacting a compound of the formula I, wherein $R_2$ represents hydrogen, and preferably a salt thereof, especially an alkali metal salt or ammonium salt thereof, with a reactive derivative, such as a halide, for example the chloride, of an acid, for example a halogenoformic acid lower alkyl ester or a lower alkanecarboxylic acid chloride.

In a resulting compound, a grouping of the formula $-C(=O)-O-R_2^A$ can be converted into another group of this formula, for example 2-chloroethoxycarbonyl or 2-bromoethoxycarbonyl of the formula $-C(=O)-O-R_2^a$ can be converted into 2-iodoethoxycarbonyl by treatment with an iodine salt, such as sodium iodide, in the presence of a suitable solvent, such as acetone.

Carboxyl groups protected by organic silyl groups or stannyl groups can be formed in a manner which is in itself known, for example by treating compounds of the formula I, wherein $R_2$ represents hydrogen, or salts, such as alkali metal salts, for example sodium salts, thereof, with a suitable silylating agent or stannylating agent, such as one of the abovementioned silylating agents or stannylating agents; see, for example, British Pat. No. 1,073,530 or Netherlands Published Specification No. 67/17107.

In a compound of the formula I, obtainable according to the invention, which has an esterified carboxyl group, with the latter representing, for example, an esterified carboxyl group of the formula $-C(=O)-O-R_2^A$ which can easily be converted into the free carboxyl group, the former group can be converted into the free carboxyl group in a manner which is in itself known, for example depending on the nature of the esterifying radical $R_2^A$; a grouping of the formula $-C(=O)-OR_2^a$ or $-C(=O)-OR_2^b$ can, for example, be converted, optionally after conversion of a group $R_o^a$, e.g. 2-chloroethyl or 2-bromoethyl, into another group $R_o^a$, particularly 2-iodoethyl, according to per se known methods, e.g. as described above, by treatment with a chemical reducing agent, such as a metal, for example zinc, or a reducing metal salt, such as a chromium-II salt, for example chromium-II chloride, usually in the presence of a hydrogen-donating agent, which together with the metal can generate nascent hydrogen, such as an acid, above all acetic acid, or formic acid, or in the presence of an alcohol, to which water is preferably added; a grouping of the formula $-C(=O)-OR_2^c$ can, for example, be converted by irradiation, preferably with ultraviolet light, using shorter-wave ultraviolet light, for example below 290 m$\mu$, if $R_2^c$ for example represents a benzyl radical which is optionally substituted in the 3-, 4- and/or 5-position, for example by lower alkoxy groups and/or nitro groups, or using longer-wave ultraviolet light, for example above 290 m$\mu$, if $R_2^c$ denotes, for example a benzyl radical substituted in the 2-position by a nitro group; a grouping $-C(=O)-OR_2^d$ can, for example, be converted by treatment with a suitable acid agent, such as formic acid or trifluoroacetic acid, optionally with the addition of a nucleophilic compound, such as phenol or anisole; a grouping $-C(=O)-OR_2^e$ can be converted by hydrolysis, for example by treatment with a weakly acid, or especially with a weakly basic, aqueous agent, such as aqueous sodium bicarbonate or an aqueous potassium phosphate buffer of pH about 7 to about 9; and a grouping $-C(=O)-OR_2^f$ can be converted by hydrogenolysis, for example by treatment with hydrogen in the presence of a noble metal catalyst, for example a palladium catalyst.

An anhydride grouping formed by the group $-C(=O)-O-$ and an acyl group $R_2^A$ may be split hydrolytically, for example, under weakly acidic conditions.

A carboxyl group which is protected, for example by silylation or stannylation, can be liberated in the usual manner, for example by treatment with water or with an alcohol.

In a resulting compound of the formula I the group R can be converted into another group R. Thus, free hydroxyl or mercapto groups, preferably of phenolic nature, in a residue R may be etherified, for example, by treatment with a diazo compound, such as a diazolower alkane, e.g. diazomethane, or with a suitable organic silyl compound, such as one of the above silylation compounds, e.g. trimethylsilyl chloride, or be esterified, for example, by treatment with an acid or a reactive derivative thereof, such as one of those mentioned above, e.g. an acid chloride. Furthermore, enol or enamine groupings may be converted into the corresponding saturated carbonyl grouping, for example by treatment with an acid, such as an aqueous mineral acid. Furthermore, in a group R a free carboxyl group may be protected, for example, esterified, for example according to the above procedure, or amidated, for example, by conversion of the free carboxylic acid into an acid halide, such as chloride (e.g. by treatment with a thionyl halide, such as thionyl chloride) and treatment thereof with ammonia or an amine, and/or an esterified carboxyl group may be converted according to per se known methods into a free carboxyl group (e.g. by hydrolysis) or another esterified carboxyl group (e.g. by transesterification); these reactions are carried out according to known methods, for example, those mentioned above.

Salts of compounds of the formula I can be manufactured in a manner which is in itself known. Thus it is possible to form salts of compounds of the formula I, wherein $R_2$ represents hydrogen, for example by treatment with metal compounds, such as alkali metal salts of suitable carboxylic acids, for example the sodium salt of $\alpha$-ethyl-caproic acid, or with ammonia or a suitable organic amine, for which purpose stoichiometric amounts, or only a slight excess of the salt-forming agent, are preferably used. Acid addition salts of compounds of the formula I having basic groupings are obtained in the usual manner, for example by treatment with an acid or with a suitable anion exchange reagent. Internal salts of compounds of the formula I, which contain a salt-forming amino group and a free carboxyl group, can, for example, be formed by neutralisation of salts, such as acid addition salts, to the isoelectric point, for example with weak bases, or by treatment with liquid ion exchangers.

Salts can be converted into the free compounds in the usual manner; metal salts and ammonium salts can, for example, be converted by treatment with suitable acids, and acid addiiton salts can, for example, be converted by treatment with a suitable basic agent.

Resulting mixtures of isomers can be separated into the individual isomers according to methods which are in themselves known, for example by fractional crystallization, adsorption chromatography (column or thin layer chromatography) or other suitable separation processes. Resulting racemates can be separated into the antipodes in the customary manner, optionally after introduction of suitable salt-forming groupings, for example by forming a mixture of diastereoisomeric salts with optically active salt-forming agents, separating the mixture into the diastereoisomeric salts and converting the salts which have been separated off into the free compounds, or by fractional crystallisation from optically active solvents.

The process also comprises those embodiments according to which compounds arising as intermediate products are used as starting substances and the remaining process stages are carried out with these or the process is stopped at any stage; furthermore, starting substances can be used in the form of derivatives or formed during the reaction.

Preferably, such starting substances are used and the reaction conditions are so chosen that the compounds initially quoted as being particularly preferred are obtained.

The starting substances of formula II used according to the process are known and can be manufactured according to processes which are in themselves known. Thus, they are for example obtained, if 7-N-$R_1^a$-N-$R_1^b$-amino-cephalosporanic acid compounds, wherein at least one of the groups $R_1^a$ and $R_1^b$ preferably represents an amino protective group having the abovementioned significance and above all represents an acyl radical Ac, are treated with a suitable weakly basic agent, such as pyridine. Herein, the free amino cephalosporanic acids are preferably used, which for example in the presence of pyridine and acetic anhydride are isomerised and form the pyridinium salts of the 7-N-$R_1^a$-N-$R_1^b$-aminoisocephalosporanic acids, which on acidification, for example with phosphoric acid, can be converted into the free compounds. The 7-N-$R_1^a$-N-$R_1^b$-amino-isocephalosporanic acid compounds thus obtainable can, if desired, be converted into other compounds of formula II. Thus, for example, the free carboxyl group can be converted into a protected carboxyl group and a protected amino group can be converted into a free amino group and the latter again into a protected, preferably acylated, amino group; these reactions can be carried out according to the methods described above. The acetoxymethyl group present in the 3-position of 7-N-$R_1^a$-N-$R_1^b$-amino-isocephalosporanic acid compounds can be converted into the hydroxymethyl group, for example by treatment with an esterase, such as an appropriate enzyme from *Rhizobium trifolii*, *Rhizobium lupinii*, *Rhizobium japonicum* or *Bacterium subtilis*, or by allowing a weakly basic, aqueous solution thereof, usually in an appropriate aqueous sodium hydroxide solution, to stand at pH 9–10. The compounds of the formula II may also be obtained by total synthesis, for example, according to the process of the British patent No. 1,155,024. 3-Hydroxymethyl- or 3-acetoxymethyl-7-N-$R_1^a$-N-$R_1^b$-amino-ceph-2-em-4ξ-carboxylic acid compounds can be converted into other 7-N-$R_1^a$-N-$R_1^b$-amino-ceph-2-em-4ξ-carboxylic acid compounds of formula II, having esterified hydroxymethyl groups in the 3-position, by esterification or trans-esterification, for example by treatment with a strong organic carboxylic acid, such as trifluoroacetic acid. Compounds of formula II, in which the group X represents a halogen atom can, for example, be obtained by halogenation of 3-methyl-7-N-$R_1^a$-N-$R_1^b$-amino-ceph-2-em-4ξ-carboxylic acid compounds, in which the amino and/or carboxyl groups are optionally protected, for example by treatment with a N-halogenoamide or N-halogenoimide compound, such as N-bromosuccinimide, and the halogen atom introduced can, by appropriate trans-halogenation, be converted into another halogen atom.

At any suitable stage in the manufacture of the starting substances, additional reactions can be carried out on intermediate products, by means of which these can be converted into other intermediate products of the same type; additional procedures of this nature are, for example, the processes described above used in the conversion of final substances.

In the manufacture of the starting substances it is possible, if necessary, for free functional groups in the reagents which do not participate in the reaction, to be temporarily protected in a manner which is in itself known, for example, free hydroxyl, mercapto and amino groups by, for example, tritylation, acylation or silylation, and free carboxyl groups by, for example, esterification, including silylation, and to be liberated in each case after the reaction has taken place, if desired, in a manner which is in itself known.

The ceph-2-em compounds of formula I can, as has already been explained above, be used as intermediate products. Thus, they can be converted into the corresponding 7-N-$R_1^a$-N-$R_1^b$-amino-3-R-methyl-ceph-3-em-4-carboxylic acid compounds of formula especially into the ceph-3-em compounds of formula IV which correspond to the ceph-2-em compounds of formula I which have been described as particularly valuable.

The compounds of formula IV are obtained, if a ceph-2-em compound of formula I is isomerised to give the corresponding ceph-3-em compound and, if desired, a resulting compound of the formula IV is converted into another compound of the formula IV, and-/or, if desired a compound obtainable according to the process, having a salt-forming group, is converted into a salt, or a resulting salt is converted into the free compound or into another salt, and/or, if desired, an isomer mixture obtainable according to the process is resolved into the individual isomers.

The isomerisation of the ceph-2-em compounds of formula I to give the corresponding ceph-3-em compounds of formula IV can be carried out in a manner which is in itself known, preferably employing compounds of formula I, in which the grouping of formula —C(=O)—O—$R_2$ represents a protected, especially an esterified carboxyl group or a carboxyl group in the form of a mixed anhydride grouping, or wherein such a protected carboxyl group is formed during the reaction.

Thus, it is possible to isomerise compounds of formula I by treating them with a weakly basic agent and isolating the corresponding ceph-3-em compound of formula IV. Suitable isomerising agents are, for example, organic nitrogen-containing bases, especially tertiary heterocyclic bases of aromatic character, above all bases of the pyridine type, such as pyridine itself, as well as collidines or lutidines, and also quinoline, tertiary aromatic bases, for example those of the aniline type, such as N,N-di-lower alkylanilines, for example N,N-dimethyl-aniline or N,N-diethylaniline, or tertiary aliphatic, azacycloaliphatic or araliphatic bases, such as N,N,N-tri-lower alkylamines, for example N,N,N-trimethylamine, N,N-dimethyl-N-ethylamine, N,N,N-triethylamine or N,N-diisopropyl-N-ethylamine, N-lower alkyl-azacycloalkanes, for example N-methyl-piperidine, or N-phenyl-lower alkyl-N,N-di-lower alkylamines, for example N-benzyl-N,N-dimethylamine, as well as mixtures of a base of the pyridine type and of an N,N,N-tri-lower alkylamine, e.g. pyridine or triethylamine. Furthermore, it is also possible to use inorganic or organic salts of bases, especially of medium-strength to strong bases with weak acids, such as alkali metal salts or ammonium salts of lower alkanecarboxylic acids, for example sodium acetate, triethylammonium acetate or N-methyl-piperidine acetate, as well as other analogous bases or mixtures of such basic agents.

The above isomerisation with basic agents can, for example, be carried out in the presence of a drivative of a carboxylic acid, which is suitable for the formation of a mixed anhydride, such as a carboxylic acid anhydride

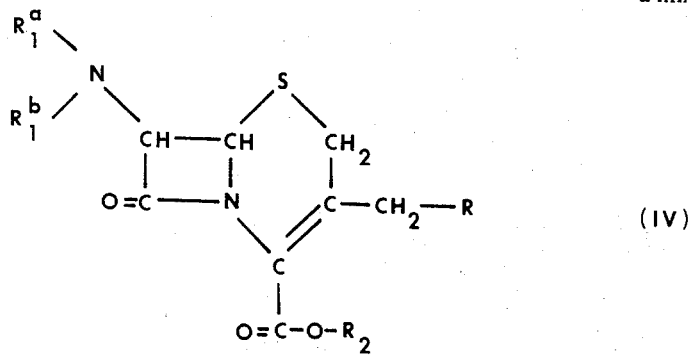

(IV)

or chloride, e.g. by treatment with pyridine in the presence of acetic acid anhydride. The above isomerisation is preferably carried out in an anhydrous medium, in the presence or absence of a solvent, such as an optionally halogenated, e.g. chlorinated, aliphatic, cycloaliphatic or aromatic hydrocarbon, or of a solvent mixture, it also being possible for bases used as reagents and which are liquid under the reaction conditions to serve as solvents, with cooling, at room temperature or with heating, preferably in a temperature interval of about −30°C to about +100°C, in an inert gas, e.g. nitrogen, atmosphere, and/or in a closed vessel.

The ceph-3-em compounds obtainable according to the process can be separated from any ceph-2-em starting material which may be present in a manner which is in itself known, for example by adsorption and/or crystallisation.

The isomerisation of ceph-2-em compounds of formula I can also be carried out if compounds of formula I are oxidised in the 1-position, if desired, a resulting mixture of isomers of the 1-oxide compounds is separated, and the resulting 1-oxides of the corresponding ceph-3-em compounds of formula IV are reduced.

Suitable oxidising agents for the oxidation, in the 1-position, of compounds of formula I are inorganic per-acids which have a reduction potential of at least 1.5 volts and consist of non-metallic elements, organic per-acids and mixtures of hydrogen peroxide and acids, particularly organic carboxylic acids, having a dissociation constant of at least $10^{-5}$. Suitable inorganic per-acids are periodic acid and persulphuric acid. Organic per-acids are corresponding percarboxylic acids and persulphonic acids, which can be added as such or can be formed in situ by using at least one equivalent of hydrogen peroxide and a carboxylic acid. Here it is advisable to use a large excess of the carboxylic acid, if, for example, acetic acid is used as the solvent. Suitable per-acids are, for example, performic acid, peracetic acid, trifluoroperacetic acid, permaleic acid, perbenzoic acid, 3-chloroperbenzoic acid, monoperphthalic acid or p-toluenepersulphonic acid.

The oxidation can also be carried out using hydrogen peroxide with catalytic amounts of an acid having a dissociation constant of at least $10^{-5}$, it being possible to to use low concentrations, for example 1–2% or less, but also larger amounts of the acid. Here the activity of the mixture above all depends on the strength of the acid. Suitable mixtures are for example those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid with a dissociation constant of at least $10^{-5}$, its activity depending on its strength. Acids suitable for use as catalysts are, for example, acetic acid, perchloric acid, and trifluoroacetic acid. Usually, at least equimolar amounts of the oxidising agent, and preferably a slight excess of about 10 to about 20%, are used, it being also possible to use larger excesses, that is to say up to the 10-fold amount of the oxidising agent, or above. The oxidisation is carried out under mild conditions, for example at temperatures of about −50° to about +100°C, preferably of about −10° to about +40°C.

In the ceph-3-em-1-oxide compounds thus obtainable, of formula

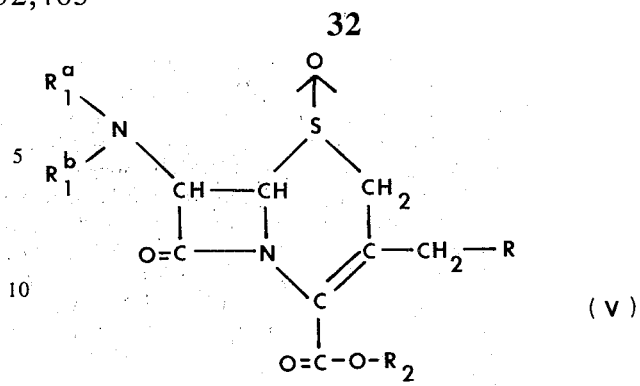

especially in those compounds of formula V in which R, $R_1^a$, $R_1^b$ and $R_2$ have the preferred meanings indicated above for the compounds of formula I, substituents such as, for example, the groups $R_1^a$, $R_1^b$ or $R_2$ can be converted into one each other or be split off or introduced within the given definition. A resulting mixture of isomeric α- and β-1-oxides may be separated, for example, chromatographically.

The reduction of the ceph-3-em-1-oxide compounds of formula V can be carried out in a manner which is in itself known, by treatment with a reducing agent, if necessary in the presence of an activating agent. Possible reducing agents are:

Catalytically activated hydrogen, using noble metal catalysts which contain palladium, platinum or rhodium and which are optionally employed together with a suitable carrier, such as charcoal or barium sulphate.

Reducing tin, iron, copper or manganese cations, which are used in the form of corresponding compounds or complexes of inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediaminetetraacetic acid or nitrolotriacetic acid. Reducing dithionite, iodide or iron-II-cyanide anions, which are used in the form of corresponding inorganic or organic salts, such as alkali metal salts, for example sodium dithionite or potassium dithionite, sodium iodide or potassium iodide or sodium iron-II-cyanide or potassium iron-II-cyanide, or in the form of the corresponding acids, such as hydriodic acid. Reducing trivalent inorganic or organic phosphorus compounds, such as phosphines, and also esters, amides and halides of phosphinous, phosphonous and phosphorus acid, as well as phosphorus-sulphur compounds corresponding to these phosphorus-oxygen compounds, wherein organic radicals above all represent aliphatic, aromatic or araliphatic radicals, for example optionally substituted lower alkyl, phenyl or phenyl-lower alkyl groups. Suitable reducing agents of this nature are, for example, triphenylphosphine, tri-n-butylphosphine, diphenylphosphinous acid methyl ester, diphenyl chlorophosphine, phenyldichlorophosphine, benzenephosphonous acid dimethyl ester, butanephosphonous acid methyl ester, phosphorus acid triphenyl ester, phosphorous acid trimethyl ester phosphorous trichloride, phosphorus tribromide and the like. Reducing halogenosilane compounds which possess at least one hydrogen atom bonded to the silicium atom and which apart from halogeno such as chloro, bromo or iodo, can also possess organic radicals, such as aliphatic or aromatic groups, for example optionally substituted lower alkyl groups or phenyl groups, such as chlorosilane, bromosilane, dichlorosilane or trichlorosilane, dibromosilane or tribromosilane, diphenylchlorosilane, dimethylchlorosilane and the like.

Reducing quaternary chloromethylene-iminium salts, especially chlorides or bromides, wherein the iminium group is substituted by a bivalent organic radical or two monovalent organic radicals, such as optionally substituted lower alkylene or lower alkyl groups, such as N-chloromethylene-N,N-diethyliminium chloride or N-chloromethylene-pyrrolidiniminium chloride. Complex metal hydrides, such as sodium borohydride in the presence of suitable activating substances, e.g. cobalt-III-chloride.

As activating agents which are used together with those of the abovementioned reducing agents which do not themselves display Lewis acid properties, that is to say which above all are employed together with the dithionite, iodide or iron-II-cyanide reducing agents and the non-halogen-containing trivalent phosphorus reducing agents, or are employed in the catalytic reduction, there should especially be mentioned organic carboxylic acid halides and sulphonic acid halides, also sulphur halides, phosphorus halides or silicium halides with a second-order hydrolysis constant equal to, or greater than, that of benzoyl chloride, for example phosgene, oxalyl chloride, acetyl chloride or acetyl bromide, chloroacetic acid chloride, pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonic acid dichloride, dimethylchlorosilane or trichlorosilane, and also suitable acid anhydrides, such as trifluoroacetic anhydride, or cyclic sultones, such as ethane sulfone, 1,3-propanesultone, 1,4-butanesultone or ethanesultone.

The reduction is preferably carried out in the presence of solvents or mixtures thereof, the choice of which is above all determined by the solubility of the starting substances and the choice of the reducing agents, such as for example lower alkane carboxylic acids or esters thereof, e.g. acetic acid and acetic acid ethyl ester, in the catalytic reduction, and, for example, optionally substituted, such as halogenated or nitrated aliphatic, cycloaliphatic, aromatic or araliphatic hydrocarbons, such as benzene, methylene chloride, chloroform or nitromethane, suitable acid derivatives, such as lower alkane carboxylic acid esters or nitriles, e.g. acetic acid ethyl ester or acetonitrile, or amides of inorganic or organic acids, e.g. dimethylformamide or hexamethylphosphor-amide, ethers, e.g. diethyl ether, tetrahydrofurane, or dioxane, ketones, e.g. acetone, or sulfones, particularly aliphatic sulfones, e.g. dimethylsulfphone or tetramethylenesulphone, and the like, together with the chemical reducing agents, whereby these solvents preferably do not contain any water. The process is usually carried out at temperatures of about −20°C to about 100°C, and, when using very reactive activating agents, the reaction can be carried out at lower temperatures.

The resulting ceph-3-em compounds of formula IV can, within the defined framework, be converted into other ceph-3-em compounds in a manner which is in itself known, for example as described above for the corresponding ceph-2-em compounds. Thus, in particular, an amino group provided with an amino protective group, optionally together with an acyl group, can be converted into a free amino group and an acylamino group, respectively, with for example in compounds of formula IV, wherein $R_1^a$ represents a suitable acyl group Ac and $R_1^b$ is hydrogen, the amino group being liberated, for example by conversion of the acyl-amino compound into a corresponding imide-halide and conversion of this into a corresponding imino-ether and saponification of the latter, for example according to the process described above, or a free amino group can be converted into a protected amino group by tritylation, acylation or silylation, for example according to the methods described above, or a protected, particularly esterified carboxyl group, including a silylated or stannylated carboxyl group, or a carboxyl group in the form of an anhydride grouping can be converted into a free carboxyl group, for example according to the methods described above, and a free carboxyl group can be converted into a protected, primarily an esterified carboxyl group by suitable conversion, such as esterification, including silylation and stannylation, for example according to the methods described above, and/or a group R may be converted, e.g. as described above, into another group R.

The present invention also comprises the ceph-3-em-1-sulphoxide compounds of formula V, wherein R, $R_1^a$, $R_1^b$ and $R_2$ have the abovementioned meanings, especially the preferred meanings indicated for the corresponding groups in compounds of formula I, and above all the compounds of the formula

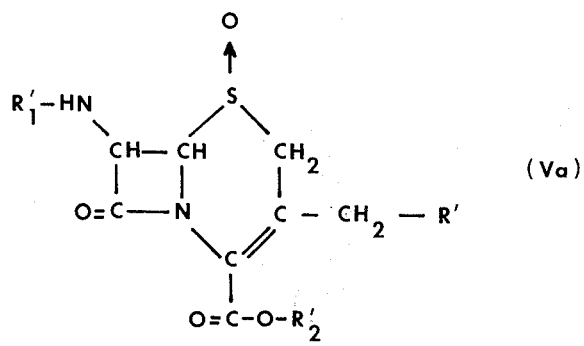

(Va)

in which R', $R_1'$ and $R_2'$ have the above given meaning.

These compounds, which may exist in the form of mixtures of isomeric 1-oxides or in the form of the 1α- and 1β-oxide isomers, represent, as indicated above, valuable intermediate products which can be converted into the compounds of formula IV in a simple manner.

The invention further comprises compounds of formula IV, wherein R, $R_1^a$, $R_1^b$ and $R_2$ have the abovementioned meanings, especially the preferred meanings indicated for the corresponding groups in compounds of formula I, with the exception of compounds of formula IV, wherein R represents an optionally substituted pyrryl or indolyl residue or a dicarbonylmethyl radical, in which each of the carbonyl groupings is part of an acyl residue or of an esterified carboxyl group, or both together are part of a bivalent diacyl residue, $R_1^a$ is hydrogen or an acyl group $R_1^b$ is hydrogen and $R_2$ has the abovementioned meanings, of compounds of formula IV, wherein R represents the 2,4-dihydroxy-phenol group, a phenyl group with two adjacent hydroxyl groups and an ethyl group in the m-position and p-position, respectively to these hydroxyl groups, the 2,4,6-trihydroxy-phenyl radical, the 2-hydroxy-1- naphthyl radical, the dicarboxymethyl radical, the carboxycarbonylmethyl radical, a dimethylaminophenyl radical, the 1-oxido-2-picolyl radical or the 2-hydroxy-1,4-dioxo-1,4-dihydro-3-naphthyl radical, $R_1^a$ represents the phenylacetyl radical, $R_1^b$ is hydrogen, and $R_2$ represents hydrogen, of compounds of formula IV, wherein R represents 2,4-dimethoxyphenyl, $R_1^a$ represents phenylacetyl, $R_1^b$ is hydrogen, and $R_2$ represents methyl, of compounds of the formula IV, in which R stands for 2-oxo-cyclohexyl, $R_1^a$ is hydrogen, 2-thienylacetyl, α-amino-phenylacetyl or α-(tert.-butyloxycarbonylamino)-phenylacetyl, $R_1^b$ is hydrogen and $R_2$ represents diphenylmethyl, or of compounds of the formula IV, in which R represents 2-oxo-cyclohexyl, $R_1^a$ is 2-thienylacetyl or α-amino-phenylacetyl, $R_1^b$ is hydrogen, and $R_2$ represents hydrogen, as well as salts of such compounds possessing salt-forming groups.

The above new compounds of formula IV, wherein $R_1^a$ represents an acyl radical occurring in pharmacologically active N-acyl derivatives of 6-amino-penam-3-carboxylic acid compounds or 7-amino-ceph-3-em-4-carboxylic acid compounds, $R_1^b$ is hydrogen and $R_2$ represents hydrogen or a radical replaceable by hydrogen under physiological conditions, or salts of such compounds which possess salt-forming groups, show valuable pharmacological properties, especially against micro-organisms, such as gram-positive and gram-negative bacteria, for example *Staphylococcus aureus*, penicillin-resistant *Staphylococcus aureus* and *Escherichia coli*, and in particular do so in dilutions of down to 0.001γ/ml. The compounds are therefore useful for the treatment of infections caused by such micro-organisms. It is also possible to use the compounds of formula IV as intermediate products for the manufacture of other compounds, especially pharmacologically valuable compounds. Thus, it is for example possible, in compounds of formula IV, wherein $R_1^a$ represents an acyl group, for example an easily removable acyl group, such as the acyl radical of a suitable carbonic acid half-derivative, for example carbonic acid half-ester, or for example represents an acyl group contained in naturally occurring or biosynthetically preparable N-acyl derivatives of 6-amino-penam-3-carboxylic acid compounds or 7-amino-ceph-3-em-4-carboxylic acid compounds, or represents a trityl group or an organic silyl or stannyl radical, and $R_1^b$ is hydrogen, to replace such a group $R_1^a$ by hydrogen (for example according to one of the processes described above) and, in a compound obtainable in this way, to substitute the free amino group (for example according to the process described above), for example by acylation with the introduction of an acyl group contained in highly active N-acyl derivatives of 6-amino-penam-3-carboxylic acid compounds or 7-amino-ceph-3-em-4-carboxylic acid compounds. Furthermore it is possible, in compounds of formula IV wherein $R_2$ represents a radical which together with the carboxyl grouping forms an esterified carboxyl group which can easily be split, to convert the esterified carboxyl group into the free carboxyl group, for example according to the processes described above, and/or, where appropriate, to convert the free carboxyl group into an esterified carboxyl group which can be split under physiological conditions.

Compounds of formula IV which should be mentioned as being particularly valuable, for example as pharmacologically active compounds or as intermediate products, are those wherein R represents an at most bicyclic aromatic hydrocarbon radical, that is to say phenyl or naphthyl radical, possessing in at least one of the ortho- and para-positions or in positions equivalent thereto one or more hydroxyl, lower alkoxy, e.g. methoxy, lower alkylthio, e.g. methylthio, amino and/or di-lower alkylamino, e.g. dimethylamino, as well as lower alkanoyloxy, e.g. acetyloxy groups and optionally other substituents, such optionally present substituents being lower alkyl, e.g. methyl, hydroxyl, lower alkoxy, e.g. methoxy, lower alkanoyloxy, e.g. acetyloxy, lower alkylthio, e.g. methythio, trifluoromethyl, amino, di-lower alkylamino, e.g. dimethylamino, lower alkanoylamino, e.g. acetylamino, lower alkanoyl, e.g. acetyl, carboxyl, lower alkoxycarbonyl, e.g. methoxycarbonyl or ethoxycarbonyl, 2-halogeno-lower alkoxycarbonyl, e.g. 2,2,2-trichloroethoxycarbonyl, 2-bromoethoxycarbonyl or 2-iodoethoxycarbonyl, carbamoyl, sulpho or sulphamoyl groups and/or halogen e.g. fluorine, chlorine or bromine atoms, an optionally substituted at most bicyclic monooxacyclic or monothiacyclic radical of aromatic character, bonded via a carbon atom and having an uneven number of ring members in the hetero-ring, such as an optionally substituted furyl, for example 2-furyl or benzofuryl, thienyl, for example 2-thienyl or benzothienyl, for example, 3-benzothienyl radical, with optionally present substituents denoting lower alkyl, e.g. methyl, carboxymethyl, lower alkoxycarbonylmethyl, e.g. methoxycarbonylmethyl or ethoxycarbonylmethyl, 2-halogeno-lower alkoxy-carbonylmethyl, e.g. 2,2,2-trichloroethoxy carbonylmethyl or 2-bromoethoxycarbonylmethyl, trifluoromethyl, hydroxyl, lower alkoxy, e.g. methoxy, lower alkanoyloxy, e.g. acetyloxy, lower alkylthio, e.g. methylthio, amino, di-lower alkylamino, e.g. dimethylamino, lower alkanoylamino, e.g. acetylamino, lower alkanoyl, e.g. acetyl, carboxyl, lower alkoxycarbonyl, e.g. methoxycarbonyl or ethoxycarbonyl, 2-halogeno-lower alkoxycarbonyl, e.g. 2,2,2-trichloroethoxycarbonyl, 2-bromoethoxycarbonyl or 2-iodoethoxycarbonyl, carbamoyl, sulpho or sulphamoyl groups and/or halogen, e.g. fluorine, chlorine or bromine atoms, or represents a radical of formula $R_a(R_b)CH-$, wherein each of the groups $R_a$ and $R_b$ represents a formyl, lower alkanoyl, e.g. acetyl, lower alkoxycarbonyl, e.g. methoxycarbonyl or ethoxycarbonyl, or cyano group, at least one of $R_a$ and $R_b$ being formyl or cyano, $R_1^a$ denotes hydrogen or an acyl contained in a naturally occurring or biosynthetically, semi-synthetically, or wholly synthetically preparable, especially pharmacologically active, such as highly active, N-acyl derivative of a 6-amino-penam-3-carboxylic acid compound or 7-amino-ceph-3-em-4-carboxylic acid compound, or an easily removable acyl radical of a carbonic acid half-derivative, especially a carbonic acid half-ester, $R_1^b$ is hydrogen and $R_2$ represents hydrogen or an organic radical $R_2^A$, which together with the —C(=O)—O— grouping forms an esterified carboxyl group which can easily be split on treatment with water, with an acid agent, with a chemical reducing agent under neutral or weakly acid conditions, or by hydrolysis or hydrogenolysis, or an esterified carboxyl group which can easily be split under physiological conditions, or a group which is easily converted into such group and represents for example, tri-lower alkyl-silyl, e.g. trimethylsilyl, tert.-lower alkyl or tert.-lower alkenyl, e.g. tert.-butyl, 2-halogeno-lower alkyl, e.g. 2,2,2-trichloroethyl, 2-chloroethyl, 2-bromoethyl or 2-iodoethyl, optionally substituted diphenylmethyl, e.g. benzhydryl or 4,4'-dimethoxydiphenylmethyl, phenacyl, 4-methoxy-benzyl, 4-nitro-benzyl or lower alkanoyloxymethyl, such as acetyloxymethyl, with the exception of those compounds of formula IV, in which R represents the 2,4-dihydroxyphenyl group, a phenyl with two adjacent hydroxyl groups and an ethyl group in the m-position and p-position, respectively to these hydroxyl groups, the 2,4,6-trihydroxy-phenyl radical, the 2-hydroxy-1-naphthyl radical, or a dimethylaminophenyl radical, $R_1{}^a$ represents the phenyl-acetyl radical, and $R_1{}^b$ and $R_2$ represents hydrogen, as well as salts of such compounds possessing salt-forming groups.

Particularly valuable compounds are those compounds for formula IV, wherein R represents a phenyl or naphthyl radical substituted in one of the ortho- or para-positions or in a position equivalent hereto by hydroxyl, lower alkoxy, for example, methoxy, lower alkanoyloxy, e.g. acetyloxy, or lower alkylthio, e.g. methylthio, whereby such residue may be further substituted, preferably in the other positions by hydroxyl or lower alkoxy, e.g. methoxy, or represents a furyl, e.g. 2-furyl, thienyl, e.g. 2-thienyl radical, optionally substituted by carboxy or lower alkoxycarbonyl, e.g. methoxycarbonyl or ethoxycarbonyl, $R_1{}^a$ represents hydrogen or an acyl radical contained in naturally occurring or biosynthetically preparable N-acyl derivatives of 6-amino-penam-3-carboxylic acid compounds or 7-amino-ceph-3-em-4-carboxylic acid compounds, such as an optionally substituted phenylacetyl or phenyloxyacetyl radical, also an optionally substituted lower alkanoyl or lower alkenoyl radical, for example the 4-hydroxy-phenylacetyl, hexanoyl, octanoyl, 3-hexanoyl, 5-amino-5-carboxy-valeryl, n-butyl-mercaptoacetyl or allylmercaptoacetyl radical, and especially the phenylacetyl or phenyloxyacetyl radical, an acyl radical occurring in highly active N-acyl derivatives or 6-amino-penam-3-carboxylic acid compounds or 7-amino-ceph-3-em-4-carboxylic acid compounds, such as formyl, 2-chloroethylcarbamoyl, cyanoacetyl or 2-thienylacetyl, especially phenylglycyl, wherein phenyl represents optionally hydroxyl-substituted and/or halogen substituted, for example chlorine substituted phenyl, for example phenyl, or 3- or 4-hydroxy- or 3,5-dichloro-4-hydroxy-phenyl, and wherein the amino group is optionally substituted and, for example, represents a sulphoamino group, optionally present in the salt form, or an amino group which is substituted by an optionally substituted carbamoyl group, such as an optionally substituted ureidocarbonyl group, for example ureidocarbonyl or $N^3$-trichloromethylureidocarbonyl, or by an optionally substituted guanidinocarbonyl group, for example guanidinocarbonyl, or by an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such an acyl radical, preferably a suitable acyl radical of a carbonic acid half-ester, such as 2,2,2-trichloroethyloxycarbonyl, 2-chloroethoxycarbonyl, 2-bromoethoxycarbonyl, 2-iodoethoxycarbonyl, tert.-butoxycarbonyl or phenacyloxycarbonyl, or of a carbonic acid half-amide, such as carbamoyl or N-methylcarbamoyl, also thienylglycyl, such as 2-thienylglycyl, (optionally with an amino group which is substituted, for example as indicated above), or 1-amino-cyclohexylcarbonyl (optionally with an amino group which is substituted, for example as indicated above) and also $\alpha$-carboxy-phenylacetyl or $\alpha$-carboxy-2-thienylacetyl (optionally with a functionally modified carboxyl group, for example a carboxyl group present in the salt form, such as sodium salt form, or in the ester form, such as lower alkyl ester form) or $\alpha$-sulfophenylacetyl or $\alpha$-sulfo-2-thienylacetyl (in which sulfo may be functionally modified, e.g. as the carboxyl group) or an acyl radical of a carbonic acid half-ester which can be split off easily, especially under acid conditions, for example on treatment with trifluoroacetic acid on reductively with zinc in the presence of aqueous acetic acid, such as tert.-butoxycarbonyl, phenylacylcarbonyl, 2,2,2-trichloroethoxycarbonyl or 2-iodoethoxycarbonyl, or 2-chloroethoxycarbonyl or 2-bromoethoxycarbonyl, which can be converted into the latter, and $R_1{}^b$ represents hydrogen and $R_2$ represents hydrogen or a radical $R_2{}^A$, which together with the —C(=O)—O— grouping forms an esterified carboxyl group which can be split easily on treatment with a chemical reducing agent under neutral or weakly acid conditions, with an acid agent or hydrolytically, preferably under weakly basic conditions, as well as hydrogenolytically and above all represents a methyl group which is polysubstituted by optionally substituted hydrocarbon radicals, such as lower alkyl radicals, especially tert.-butyl or diphenylmethyl, and 2,2,2-trichloroethyl, 2-iodoethyl, and 2-bromoethyl which can easily be converted into 2-iodoethyl, or phenacyl, as well as 4-methoxybenzyl or 4-nitrobenzyl, as well as lower alkanoyloxymethyl, e.g. acetyloxymethyl.

Such compounds are especially those of the formula

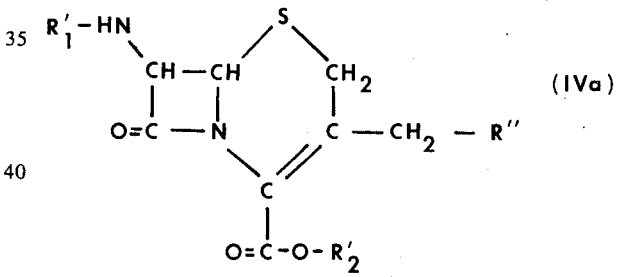

in which R'' is 2- or 4-hydroxy-phenyl, 2,5- or 3,4-dihydroxyphenyl, 2- or 4-lower alkoxy-, e.g. 2- or 4-methoxy-phenyl, 2,4-, 2,5- or 3,4-di-lower alkoxy-, e.g. 2,4-, 2,5- or 3,4-dimethoxy-phenyl, 2- or 4-lower alkanoyloxy-, e.g. 2- or 4-acetyloxy-phenyl, 4-lower alkyl-thio-, e.g. 4-methylthio-phenyl, 2-thienyl, 2-furyl, 5-carboxy-2-furyl, 5-lower alkoxycarbonyl-, e.g. 5-methoxycarbonyl-2-furyl or 5-ethoxycarbonyl-2-furyl, and $R_1$ and $R_2$ have the meaning given above, as well as salts of such compounds with salt-forming groupings.

The pharmacologically active compounds of the present invention are useful in the manufacture of pharmaceutical compositions, containing an effective amount thereof in conjunction or admixture with inorganic or organic, solid or liquid excipients suitable for enteral or parenteral application. Preferred are tablets and gelatin capsules comprising the active ingredient together with diluents, e.g. lactose, dextrose, sucrose, mannitol, sorbitol, cellulose and/or glycine, and lubricants, e.g. silica, talcum, stearic acid or salt thereof, such as magnesium or calcium salts thereof, and/or polyethyleneglycol; tablets also contain binders, e.g. magnesium aluminum silicate, starches, e.g. corn, wheat or rice starch or arrow root, gelatin, tragacanth, methylcellulose, sodium carboxymethylcellulose and/or polyvinylpyrrolidone, and, if desired, disintegrants, e.g. starches, agar, alginic acid or a salt, such as the sodium salt, thereof, and/or effervescent mixtures and adsorbents, colorants, flavors and/or sweeteners. Injectable compositions are preferably aqueous isotonic solutions or suspensions, suppositories advantageously fatty emulsions or suspensions. They may be sterilized and/or contain auxiliary substances, such as preserving, stabilizing, wetting and/or emulsifying agents, solubilizers, salts for regulating the osmotic pressure and/or buffers. The pharmaceutical preparations, which in addition may include other therapeutically valuable substances, are prepared according to known methods, e.g. conventional mixing, granulating or coating methods and contain froom about 0.1 to about 75%, preferably from about 1 to about 50% of the active ingredient.

The following Examples are intended to illustrate the invention; temperatures are given in degrees Centigrade.

EXAMPLE 1:

A mixture of 5 g of 3-acetoxymethyl-7(N-phenylacetyl-amino)-ceph-2-em-4$\xi$-carboxylic acid and 10 ml of absolute anisole is dissolved in 40 ml of trifluoracetic acid and the clear solution is evaporated to dryness under a water pump vacuum and with repeated addition of toluene. The residue is dissolved in acetone, and the solution is mixed with about 30 g of silica gel and evaporated to dryness. The residue is suspended in methylene chloride and the suspension is applied to a column (diameter: 35 mm) of 150 g of silica gel. Elution is carried out with methylene chloride and mixtures of methylene chloride and acetic acid ethyl ester (fractions of 400 ml). Unreacted anisole is eluted with 2 fractions of pure methylene chloride. 3-(4-Methoxybenzyl)-7-(N-phenylacetyl-amino)-ceph-2-em-4$\xi$-carboxylic acid mixed with 3-(2-methoxy-benzyl)-7-(N-phenylacetyl-amino)-ceph-2-em-4$\xi$-carboxylic acid, is obtained by elution with 6:1 to 1:1 mixtures of methylene chloride and acetic acid ethyl ester. Additional, impure material is obtained with acetic acid ethyl ester and with acetic acid ethyl ester containing 5% of methanol. The pure product is crystallised from a mixture of acetic acid ethyl ester and cyclohexane and melts at 181.5°–182°C (uncorrected); $[\alpha]_D^{20} = +379° \pm 1°$ (c = 0.989 in dioxane); thin layer chromatogram (silica gel G): Rf = 0.61 (system n-butanol/acetic acid/water, 75:7.5:21), Rf = 0.72 (system acetic acid ethyl ester/pyridine/acetic acid/water, 62:21:6:11) and Rf = 0.63 (system n-butanol/pyridine/acetic acid/water, 38:24:8:30); ultraviolet absorption spectrum (in 95% strength ethanol), $\lambda_{max} = 224$ m$\mu$($\epsilon = 19200$), and shoulder at about 255 m$\mu$ ($\epsilon = 7200$) and at about 279 m$\mu$ ($\epsilon = 3000$); infrared absorption spectrum (in mineral oil): characteristic bands at 3.02$\mu$, 3.19$\mu$ (shoulder), 3.30$\mu$, 5.67$\mu$, 5.77$\mu$, 6.05$\mu$, 6.23$\mu$, 6.54$\mu$, 6.61$\mu$, 6.69$\mu$, 7.07$\mu$, 7.49$\mu$, 7.99$\mu$, 8.24$\mu$, 8.52$\mu$, 9.71$\mu$, 13.31$\mu$, 14.41$\mu$ and 15.05$\mu$. Further recrystallisation from a mixture of acetone, methylene chloride and cyclohexane results in enrichment of 3-(4-methoxybenzyl)-7-(N-phenylacetyl-amino)-ceph-2-em-4$\xi$-carboxylic acid, with the melting point rising to 188°C.

EXAMPLE 2:

0.800 g of 3-acetoxymethyl-7-(N-phenylacetyl-amino)-ceph-2-em-4$\xi$-carboxylic acid is mixed with a solution of 1.12 g of hydroquinone-dimethyl-ether (twice recrystallised from methanol, melting point 54°–55°C, uncorrected) in 4.47 ml of trifluoroacetic acid, and the clear yellow solution is left to stand for 15 minutes at room temperature and evaporated in a rotary evaporator. The residue is four times evaporated to dryness with a few milliliters of absolute toluene, is then freed of the trifluoroacetic acid over the course of 30 minutes in a high vacuum over solid potassium hydroxide, and is taken up in 50 ml of an 0.5 molar aqueous dipotassium hydrogen phosphate solution and 100 ml of acetic acid ethyl ester. The mixture is well shaken and the organic phase is separated off and extracted twice more with 20 ml of the buffer solution. The aqueous solutions are twice extracted by shaking with 100 ml portions of acetic acid ethyl ester. The combined organic extracts are dried over anhydrous sodium sulphate and evaporated to dryness; excess hydroquinone-dimethyl-ether is thus obtained.

The aqueous phases (pH 7.5) are covered with 150 ml of acetic acid ethyl ester and adjusted to pH 2 with 5 molar aqueous phosphoric acid. The aqueous layer is separated off, saturated with sodium chloride and re-extracted with 2 portions, each of 100 ml, of acetic acid ethyl ester. The organic solutions are washed six times with 30 ml portions of a saturated aqueous sodium chloride solution (final pH value: about 4), dried over sodium sulphate and freed of the solvent under reduced pressure. The residue is dissolved in acetone, mixed with about 3 g of silica gel and evaporated to dryness. The residue is charged onto a column (diameter: 20 mm) of 30 g of silica gel. Elution is carried out with methylene chloride containing from 1 – 25% of acetic acid ethyl ester, with the desired 3-(2,5-dimethoxybenzyl)-7-(N-phenylacetyl-amino)-ceph-2-em-4$\xi$c-carboxylic acid being extracted with methylene chloride containing 12 – 15% of acetic acid ethyl ester. The product is crystallised from a mixture of acetone, acetic acid ethyl ester and cyclohexane, melting point 181.5°–182.5°C (uncorrected; with decomposition). After two recrystallisations from the same solvent mixture and drying over phosphorus pentoxide and paraffin chips for 16 hours in a high vacuum, the analytically pure preparation melts at 182°–183°C (uncorrected); $[\alpha]_D^{20} \times +326° \pm 1°$ (c = 1.139 in dioxane); thin layer chromatogram (silica gel G): Rf = 0.67 (system n-butanol/acetic acid/water, 75:7.5:21), Rf = 0.48 (system n-butanol/ethanol/water, 40:10:50), Rf = 0.70 (system acetic acid ethyl ester/pyridine/acetic acid/water, 62:21:6:11) and Rf = 0.63 (system n-butanol/pyridine/acetic acid/water, 38:24:8:30); ultraviolet absorption spectrum (in 95% ethanol): $\lambda_{max}$ 293 m$\mu$ ($\epsilon = 4350$), $\lambda_{min}$ 272 m$\mu$ ($\epsilon = 2000$), and shoulders at 258 m$\mu$ ($\epsilon = 4900$), 250 m$\mu$ ($\epsilon = 6000$) and 221 m$\mu$ ($\epsilon = 17600$); infrared absorption spectrum (in mineral oil): characteristic bands at 2.99$\mu$, 3.16$\mu$ (shoulder), 3.28$\mu$ (shoulder), 5.68$\mu$, 5.77$\mu$, 6.01$\mu$, 6.56$\mu$, 6.65$\mu$, 7.08$\mu$, 8.14$\mu$, 8.53$\mu$, 9.53$\mu$, 12.36$\mu$, 14.04$\mu$, 14.28$\mu$ and 14.43$\mu$.

EXAMPLE 3:

A solution of 0.8 g of freshly distilled 1-methoxynaphthalene in 2.2 ml of trifluoroacetic acid is mixed with 0.4 g of 3-acetoxymethyl-7-(N-phenylacetylamino)-ceph-2-em-4ξ-carboxylic acid and the resulting solution is left to stand for 15 minutes at room temperature. It is then diluted with an equal amount of toluene and evaporated to dryness under reduced pressure. The residue is taken up in 50 ml of acetic acid ethyl ester and 30 ml of a 10% strength aqueous dipotassium hydrogen phosphate solution. The whole is thoroughly shaken, the organic layer is separated off and the aqueous phase is extracted with two 50 ml portions of acetic acid ethyl ester. The aqueous phase is covered with 50 ml of acetic acid ethyl ester and the pH value is adjusted to 2 by adding 2% strength aqueous phosphoric acid. After vigorous shaking, the organic solution is separated off, and the aqueous phase is twice extracted with 50 ml portions of acetic acid ethyl ester. The combined organic extracts are washed three times with 50 ml portions of a saturated aqueous sodium chloride solution, dried over anhydrous sodium sulphate, filtered and evaporated to dryness under reduced pressure. 3-(4-Methoxy-1-naphthylmethyl)-7-(N-phenylacetylamino)-ceph-2-em-4ξ-carboxylic acid is obtained as an oily residue, which on trituration with acetic acid ethyl ester crystallises and after recrystallisation from methanol melts at 196°C; thin layer chromatogram (silica gel): Rf = 0.71 (system n-butanol/acetic acid/water, 75:7.5:21), Rf = 0.76 (system n-butanol/acetic acid/water, 67:10:23) and Rf = 0.52 (system n-butanol/ethanol/water, 40:10:50); ultraviolet absorption spectrum (in methanol): $\lambda_{max}$ = 225 m$\mu$ ($\epsilon$ = 17,600) and 298 m$\mu$ ($\epsilon$ = 8300) and shoulder at 308 m$\mu$ ($\epsilon$ = 6400) and 322 m$\mu$ ($\epsilon$ = 3950); infrared absorption spectrum (in mineral oil): characteristic bands at 3.02$\mu$, 5.69$\mu$, 5.77$\mu$, 6.06$\mu$ and 6.59$\mu$.

EXAMPLE 4:

1.95 g of 3-acetoxymethyl-7-(N-phenylacetylamino)-ceph-2-em—4ξ—carboxylic acid are dissolved in a solution of 4.7 g of phenol in 15 ml of trifluoroacetic acid, and the solution is left to stand for 15 minutes at room temperature and is then diluted with an equal amount of toluene. After evaporation under reduced pressure, the residue is taken up in 100 ml of acetic acid ethyl ester and 50 ml of an aqueous 10% strength dipotassium hydrogen phosphate solution, the mixture is well shaken and the organic phase is separated off. The aqueous layer is twice washed with 100 ml portions of acetic acid ethyl ester to remove the excess phenol and then covered with 100 ml of acetic acid ethyl ester, and its pH value is adjusted to 2 by means of 20% strength aqueous phosphonic acid. The organic layer is separated off after thorough shaking, the aqueous solution is twice extracted with 100 ml portions of acetic acid ethyl ester, and the combined organic extracts are washed three times with 50 ml portions of a saturated aqueous sodium chloride solution, dried over anhydrous sodium sulphate, filtered and evaporated to dryness under reduced pressure. The residue is triturated with acetic acid ethyl ester and yields 3-(4-hydroxybenzyl)-7-(N-phenylacetyl-amino)-ceph-2-em-4ξ-carboxylic acid, which after recrystallisation from a mixture of acetic acid ethyl ester and methanol melts at 210°C; thin layer chromatogram (silica gel): Rf= 0.72 (system n-butanol/acetic acid/water, 75:7.5:21), Rf = 0.77 (system n-butanol/acetic acid/water, 67:10:23) and Rf = 0.49 (system n-butanol/ethanol/water, 40:10:50); ultraviolet absorption spectrum (in methanol): $\lambda_{max}$ = 224 m$\mu$ ($\epsilon$ = 15800) and 276 m$\mu$ ($\epsilon$ = 2400), and shoulder at 282 m$\mu$ ($\epsilon$ = 1900); infrared absorption spectrum (in mineral oil): characteristic bands at 3.01$\mu$, 5.77$\mu$, 5.80$\mu$, 6.07$\mu$ and 6.62$\mu$.

EXAMPLE 5:

0.1 g of 3-acetoxymethyl-7-(N-phenylacetyl-amino)-ceph-2-em-4ξ-carboxylic acid are dissolved in a solution of 0.056 g of anisole in 5 ml of chloroform, and the solution is cooled to 0°C and saturated with boron trifluoride gas for 15 minutes. The temperature of the reaction mixture is thereafter brought to room temperature over the course of 2 hours; 50 ml of acetic acid ethyl ester are added, and the mixture is again cooled to 0°C and slowly poured into 50 ml of a 10% strength aqueous dipotassium hydrogen phosphate solution. The pH value is adjusted to 7.5 and the mixture is thoroughly shaken. The aqueous phase is twice washed with 50 ml portions of acetic acid ethyl ester, the pH value is adjusted to 2 by means of 20% strength aqueous phosphoric acid, and three extractions with 50 ml portions of acetic acid ethyl ester are carried out. The oroganic extracts are repeatedly washed with a saturated aqueous sodium chloride solution, dried over anhydrous sodium sulphate, filtered and evaporated under reduced pressure. 3-(4-Methoxy-benzyl)-7-(N-phenylacetyl-amino)-ceph-2-em-4ξ-carboxylic acid containing a small amount of the corresponding 2-methoxy-benzyl compound are thus obtained as the residue; in a thin layer chromatogram, this acid does not differ from the product of the process of example 1.

EXAMPLE 6:

A solution of 0.088 g of anisole and 0.025 g of iodine in 2 ml of acetone is mixed with 0.069 g of 3-hydroxymethyl-7-(N-phenylacetyl-amino)-ceph-2-em-4ξ-carboxylic acid and the solution is left to stand for 15 minutes at room temperature and then evaporated under reduced pressure. The residue is taken up in 2 ml of acetic acid ethyl ester and 2 ml of 10% strength aqueous dipotassium hydrogen phosphate solution, the pH is adjusted to 7.5, and the two layers are separated after thorough shaking. The aqueous phase is twice washed with 7.5 ml portions of acetic acid ethyl ester, its pH value is adjusted to 2 with 20% strength aqueous phosphoric acid, and it is extracted three times with 7.5 ml portions of acetic acid ethyl ester. The combined organic extracts are washed with a saturated aqueous sodium chloride solution, dried over anhydrous sodium sulphate, filtered and evaporated under reduced pressure. The residue represents 3-(4-methoxy-benzyl)-7-(N-phenylacetyl-amino)-ceph-2-em-4ξ-carboxylic acid, which contains a small amount of the corresponding 2-methoxy-benzyl compound and which in a thin layer chromatogram does not differ from the product of the process of example 1.

EXAMPLE 7:

0.1 g of 3-hydroxymethyl-7-(N-phenylacetyl-amino)-ceph-2-em-4ξ-carboxylic acid is dissolved in a solution of 0.056 g of anisole in 0.8 ml of trifluoroacetic acid. The solution is left to stand for 15 minutes at room temperature and is then diluted with an equal amount of toluene. The solution is evaporated under reduced pressure and the residue is worked up in accordance with the method described in example 6. 3-(4-methoxy-benzyl)-7-(N-phenylacetyl-amino)-ceph-2-em-4ξ-carboxylic acid, containing a small amount of the corresponding 2-methoxy-benzyl compound, is thus obtained; in a thin layer chromatogram, this acid does not differ from the product of the process of example 1.

EXAMPLE 8:

A solution of 0.044 g of anisole in 1 ml of anhydrous formamide is mixed with 0.044 g of 7-(N-phenylacetylamino)-3-trifluoroacetoxymethyl-ceph-2-em-4ξ-carboxylic acid and the mixture is left to stand for 1 hour at 50°C under a nitrogen atmosphere. It is then evaporated to dryness under reduced pressure and the residue is worked up in accordance with the process described in example 6. 3-(4-Methoxy-benzyl)-7-(N-phenylacetyl-amino)-ceph-2-em-4ξ-carboxylic acid, containing a small amount of the corresponding 2-methoxybenzyl compound, is thus obtained; in a thin layer chromatogram, this acid does not differ from the product of the process of example 1.

The starting material can be manufactured as follows:

A solution of 0.8 g of 3-acetoxymethyl-7-(N-phenylacetyl-amino)-ceph-2-em-4ξ-carboxylic acid in 4 ml of trifluoroacetic acid is left to stand for 15 minutes at room temperature and is then diluted with an equal quantity of toluene. The volatile constituents are evaporated under reduced pressure and at room temperature. The residue is taken up in 100 ml of chloroform and the mixture is filtered. The filtrate is concentrated to a small volume under reduced pressure and cooled. The resulting solid material is filtered off and yields 7-(N-phenylacetyl-amino)-3-trifluoroacetoxymethyl-ceph-2-em-4ξ-carboxylic acid, melting at 139°–140°C; infrared absorption spectrum (in mineral oil): characteristic bands at $3.01\mu$, $5.60\mu$, $5.65\mu$, $5.73\mu$, $5.77\mu$, $6.02\mu$ and $6.54\mu$. A further quantity of the desired product can be obtained by further concentration and cooling of the filtrate.

EXAMPLE 9:

A solution of 0.044 g of anisole and 0.0172 g of p-toluenesulphonic acid in 2 ml of anhydrous dioxane is mixed with 0.035 g of 3-hydroxymethyl-7-(N-phenylacetyl-amino)-ceph-2-em-4ξ-carboxylic acid and the resulting solution is left to stand for one hour at room temperature. The solvent is removed under reduced pressure and the residue is triturated with diethyl ether to remove the excess of p-toluenesulphonic acid and is worked up in accordance with the process described in example 6. 3-(4-Methoxy-benzyl)-7-(N-phenylacetyl-amino)-ceph-2-em-4ξ-carboxylic acid containing a small amount of the corresponding 2-methoxybenzyl compound is thus obtained; in a thin layer chromatogram, this acid does not differ from the product of the process of example 1.

EXAMPLE 10:

A solution of 0.055 g of resorcinol in 0.3 ml of trifluoroacetic acid is mixed with 0.04 g of 3-acetoxymethyl-7-(N-phenylacetyl-amino)-ceph-2-em-4ξ-carboxylic acid and the solution is left to stand for 15 minutes at room temperature. It is diluted with an equal quantity of toluene and then evaporated to dryness under reduced pressure. 3-(2,4-Dihydroxybenzyl)-7-(N-phenylacetyl-amino)-ceph-2-em-4ξ-carboxylic acid is obtained by working up the residue in accordance with the process indicated in example 6; this acid shows the following Rf values in a thin layer chromatogram (silica gel): 0.66 (system n-butanol/acetic acid/water, 75:7.5:21), 0.70 (system n-butanol/acetic acid/water, 67:10:23) and 0.52 (system n-butanol/ethanol/water, 40:10:50).

EXAMPLE 11:

A solution of 0.063 g of phloroglucinol in 0.3 ml of trifluoroacetic acid is mixed with 0.04 g of 3-acetoxymethyl-7-(N-phenylacetyl-amino)-ceph-2-em-4ξ-carboxylic acid, and the solution is left to stand for 30 minutes at room temperature and diluted with an equal quantity of toluene. The mixture is evaporated to dryness under reduced pressure and the residue is worked up in accordance with the process described in example 6. 7-(N-Phenylacetyl-amino)-3-(2,4,6-trihydroxybenzyl)-ceph-2-em-4ξ-carboxylic acid is thus obtained, showing the following Rf values in a thin layer chromatogram (silica gel): 0.73 (system n-butanol/acetic acid/water, 67:10:23) and 0.55 (system n-butanol/ethanol/water, 40:10:50).

EXAMPLE 12:

A solution of 1.1 g of pyrocatechol in 6 ml of trifluoroacetic acid is mixed with 0.8 g of 3-acetoxymethyl-7-(N-phenylacetyl-amino)-ceph-2-em-4ξ-carboxylic acid and the solution is left to stand for 15 minutes at room temperature. It is diluted with an equal quantity of toluene, the mixture is evaporated to dryness under reduced pressure, and the residue is twice triturated with 30 ml portions of diethyl ether to remove the excess pyrocatechol. The residue is worked up in accordance with the process described in example 6 and yields 3-(3,4-dihydroxybenzyl)-7-(N-phenylacetyl-amino)-ceph-2-em-4ξ-carboxylic acid which after crystallisation from a mixture of acetic acid ethyl ester and acetone is obtained in the form of colourless crystals, melting point 114°C; thin layer chromatogram (silica gel): Rf = 0.71 (system n-butanol/acetic acid/water, 75:7.5:21), Rf = 0.73 (system n-butanol/acetic acid/water, 67:10:23) and Rf = 0.44 (system n-butanol/ethanol/water, 40:10:50); ultraviolet absorption spectrum (methanol): $\lambda_{max}$ 222 m$\mu$ ($\epsilon$ = 17600), 250 m$\mu$ ($\epsilon$ = 6800) and 283 m$\mu$ ($\epsilon$ = 3700); infrared absorption spectrum (in mineral oil): characteristic bands at $3.01\mu$, $5.72\mu$, $5.87\mu$ and $6.06\mu$.

EXAMPLE 13:

A solution of 0.055 g of hydroquinone in 0.3 ml of trifluoroacetic acid is mixed with 0.04 ml of 3-acetoxymethyl-7-(N-phenylacetyl-amino)-ceph-2-em-4ξ-carboxylic acid, and the mixture is left to stand for 15 minutes at room temperature and is then diluted with an equal volume of toluene. This mixture is evaporated to dryness under reduced pressure and the residue is worked up in accordance with the process described in example 6. The 3-(2,5-dihydroxybenzyl)-7-(N-phenylacetyl-amino(-ceph-2-em-4ξ-carboxylic acid thus obtained shows the following Rf values in a thin layer chromatogram (silica gel): 0.65 (system n-butanol/acetic acid/water, 75:7.5:21), 0.68 (system n-butanol/acetic acid/water, 67:10:23) and 0.51 (system n-butanol/ethanol/water, 40:10:50).

EXAMPLE 14:

A solution of 3.4 g of thiophene in 200 ml of trifluoroacetic acid is mixed with 4 g of 3-acetoxymethyl-7-(N-phenylacetyl-amino)-ceph-2-em-4ξ-carboxylic acid and the solution is left to stand for 15 minutes at room temperature and then mixed with an equal quantity of toluene, and the mixture is evaporated under reduced pressure. The residue is triturated with acetic acid ethyl ester and the solid material is twice crystallised from a mixture of methanol and acetic acid ethyl ester. 7-(N-Phenylacetyl-amino)-3-(2-thenyl)-ceph-2-em-4ξ-carboxylic acid is thus obtained as colourless crystals, melting point 189°C; thin layer chromatogram (silica gel): Rf = 0.72 (system n-butanol/acetic acid/water, 75:7.5:21), Rf = 0.81 (system n-butanol/acetic acid/water, 67:10:23) and Rf = 0.50 (system n-butanol/ethanol/water, 40:10:50); ultraviolet absorption spectrum (in methanol): $\lambda_{max}$ = 233 m$\mu$ ($\epsilon$ = 15400); infrared absorption spectrum (in mineral oil): characteristic bands at 3.01$\mu$, 5.73$\mu$, 5.82$\mu$ and 6.05$\mu$. A further quantity of the desired product can be obtained by concentrating the mother liquor and recrystallising the crystalline material.

EXAMPLE 15:

A solution of 0.504 g of 2-furanecarboxylic acid methyl ester in 20 ml of trifluoroacetic acid is mixed with 0.4 g of 3-acetoxymethyl-7-(N-phenylacetyl-amino)-ceph-2-em-ξ-carboxylic acid and the resulting solution is left to stand for 45 minutes at room temperature and then diluted with an equal volume of toluene. The mixture is evaporated to dryness under reduced pressure; the oily residue is triturated with acetic acid ethyl ester and yields 3-(5-methoxycarbonyl-2-furfuryl)-7-(N-phenylacetyl-amino)-ceph-2-em-ξ-carboxylic acid, which after recrystallisation from acetic acid ethyl ester melts at 193°C; thin layer chromatogram (silica gel): Rf = 0.65 (system n-butanol/acetic acid/water, 75:7.5:21), Rf = 0.75 (system n-butanol/acetic acid/water, 67:10:23) and Rf = 0.43 (system n-butanol/ethanol/water, 40:10:50).

EXAMPLE 16:

0.04 g of 3-acetoxymethyl-7-(N-phenylacetyl-amino)-ceph-2-em-4ξ-carboxylic acid and 0.027 g of furane are simultaneously dissolved in 2 ml of trifluoroacetic acid; the solution is left to stand for 15 minutes at room temperature and is then diluted with an equal volume of toluene. The mixture is evaporated to dryness under reduced pressure and the residue is worked up in accordance with the process described in example 6. 3-Furfuryl-7-(N-phenylacetyl-amino)-ceph-2-em-4ξ-carboxylic acid is thus obtained, showing the following Rf values in a thin layer chromatogram (silica gel): 0.75 (system n-butanol/acetic acid/water, 67:10:23) and 0.52 (system n-butanol/ethanol/water, 40:10:50).

EXAMPLE 17:

0.04 g of 3-acetoxymethyl-7-(N-phenylacetyl-amino)-ceph-2-em-4ξ-carboxylic acid is dissolved in a solution of 0.117 g of indole in 0.3 ml of trifluoroacetic acid; the solution is left to stand for 15 minutes at room temperature and is then diluted with an equal volume of toluene. The mixture is evaporated to dryness under reduced pressure, the residue is worked up in accordance with the process described in example 6, and 3-(3-indolylmethyl)-7-(N-phenylacetyl-amino)-ceph-2-em-4ξ-carboxylic acid is thus obtained; in a thin layer chromatogram (silica gel), this acid shows Rf values of 0.73 (system n-butanol/acetic acid/water, 75:75:21), 0.82 (system n-butanol/acetic acid/water, 67:10:23) and 0.65 (system n-butanol/ethanol/water, 40:10:50).

EXAMPLE 18:

0.04 g of 3-acetoxymethyl-7-(N-phenylacetyl-amino)-ceph-2-em-4ξ-carboxylic acid is dissolved in a solution of 0.13 g of 1-methylindole in 0.3 ml of trifluoroacetic acid, and the solution is left to stand for 15 minutes at room temperature and diluted with an equal quantity of toluene. The mixture is evaporated to dryness under reduced pressure and the residue is worked up in accordance with the process described in example 6. 3-(1-Methyl-3-indolylmethyl)-7-(N-phenylacetyl-amino)-ceph-2-em-4ξ-carboxylic acid is thus obtained; in a thin layer chromatogram (silica gel), this acid shows Rf values at 0.85 (system n-butanol/acetic acid/water, 67:10:23) and at 0.58 (system n-butanol/ethanol/water, 40:10:50).

EXAMPLE 19:

A solution of 0.044 g of anisole and 0.0125 g of iodine in 2 ml of acetone is mixed with 0.04 g of 3-acetoxymethyl-7-(N-phenylacetyl-amino)-ceph-2-em-ξ-carboxylic acid; the solution is left to stand for 15 minutes at room temperature and is then worked up in accordance with the process described in example 6. 3-(4-Methoxy-benzyl)-7-(N-phenylacetyl-amino)-ceph-2-em-ξ-carboxylic acid, containing a small quantity of the corresponding 2-methoxybenzyl compound, is thus obtained; in a thin layer chromatogram, this acid does not differ from the product of the process of example 1.

EXAMPLE 20:

11.7 Grams of 3-acetyloxymethyl-7$\beta$-phenylacetyl-amino-ceph-2-em-4ξ-carboxylic acid are dissolved in a solution of 18.6 g of guaiacol in 300 ml of trifluoroacetic acid and the mixture is left to stand to 15 minutes at room temperature, then diluted with an equal volume of toluene and evaporated under reduced pressure. The residue is partitioned between ethyl acetate and an aqueous dipotassium hydrogen phosphate buffer solution (pH 7.5) and the layers are separated. The aqueous layer is thoroughly washed with ethyl acetate, its pH then adjusted to 2.5 with 20% aqueous phosphoric acid and again extracted with ethyl acetate. The latter extracts are washed with water and a saturated aqueous sodium chloride solution, dried over magnesium sulphate and evaporated under reduced pressure. The residue is recrystallised from ethyl acetate to yield the 3-(4-hydroxy-3-methoxy-benzyl)-7$\beta$-phenylacetyl-amino-ceph-2-em-4ξ-carboxylic acid, m.p. 198–199°; thin-layer chromatogram (silica gel): Rf = 0.76 (system n-butanol/acetic acid/water 67:10:23) and Rf = 0.43 (system n-butanol/ethanol/water 40:10:50); ultraviolet absorption spectrum (in methanol): $\lambda_{max}$ = 235 m$\mu$ ($\epsilon$ = 6800) and 282 m$\mu$ ($\epsilon$ = 1820); infrared absorption spectrum (in mineral oil): characteristic bands at 2,85$\mu$, 2,99$\mu$, 5,67$\mu$, 5.74$\mu$ and 6.56$\mu$. It is possible to obtain a further amount of the desired product from the mother liquor via the diphenylmethyl ester.

EXAMPLE 21:

A solution of 0.56 g of 2-furan carboxylic acid in 40 ml of trifluoroacetic acid is treated with 1.00 g of 3-acetyloxymethyl-7$\beta$-phenyl-acetyl-amino-ceph-2-em-4ξ-carboxylic acid and left to stand for 60 minutes at room temperature, then diluted with the same volume of toluene. The mixture is evaporated to dryness under reduced pressure and the residue triturated several times with a 3:7-mixture of diethyl ether and toluene and filtered. The filter residue constitutes the 3-(5-carboxy-furfuryl)-7β-phenylacetyl-amino-ceph-2-em-4ξ-carboxylic acid, which after recrystallisation from ethyl acetate melts at 194°–195°.

EXAMPLE 22:

A solution of 7.8 g of 3-acetyloxymethyl-7β-phenylacetyl-amino-ceph-2-em- 4ξ-carboxylic acid in 60 ml of trifluoroacetic acid, prepared at room temperature within 15 minutes, is treated with an equal volume of toluene and evaporated to dryness. The residue, which contains the 7β-phenylacetyl-amino-3-trifluoroacetyloxymethyl-ceph-2-em- 4ξ-carboxylic acid, is dissolved in 200 ml of dry formamide and treated with 5.80 ml of furan. After reacting for 1 hour at 50° under nitrogen, the reaction mixture is cooled and treated with ethyl acetate and 10% aqueous dipotassium hydrogen phosphate solution (pH 7.5). The aqueous solution is separated and washed several times with ethyl acetate. The aqueous phase is adjusted to pH 2.5 with 20% aqueous phosphoric acid and extracted with ethyl acetate. The resulting organic extract is washed with water and a saturated aqueous sodium chloride solution, dried over magnesium sulphate and evaporated under reduced pressure. The solid residue is crystallised from ethal acetate to yield the almost pure 3-furfuryl-7β-phenylacetyl-amino-ceph- 2-em-4ξ-carboxylic acid, which after repeated recrystallisation from ethyl acetate melts at 188°–190°; thin-layer chromatogram (silica gel): Rf = 0.75 (system n-butanol/acetic acid/water 67:10: 23) and Rf = 0.53 (system n-butanol/ethanol/water 40:10:50); ultraviolet absorption spectrum (in methanol): strong terminal absorption; infrared absorption spectrum (in mineral oil); characteristic bands at 3,01μ, 5,66μ, 5,75μ, 6,02μ and 6,54μ.

EXAMPLE 23:

A solution of 3.9 g of 3-acetyloxymethyl-7β-phenylacetyl-amino-ceph-2-em -4ξ-carboxylic acid and 5.0g of 2-methoxycarbonyl-pyrrole in 20 ml of trifluoroacetic acid is allowed to stand for 15 minutes at room temperature and then diluted with an equal volume of toluene. The solution is evaporated to dryness under reduced pressure and the residue is partitioned between ethyl acetate and a 10% aqueous dipotassium hydrogen phosphate solution (pH 7.8). The layers are separated; the aqueous phase is washed several times with ethyl acetate, adjusted to pH 2.5 by addition of a 20% aqueous phosphoric acid solution and extracted with ethyl acetate. The resulting extracts are washed with water and a saturated aqueous sodium chloride solution, dried over magnesium sulphate and evaporated under reduced pressure. The residue is dissolved in 10 ml of methanol and the solution diluted with 90 ml of ethyl acetate.

3.8 Grams of diphenyldiazomethane in 50 ml of ethyl acetate are added to the solution containing the resulting 3-(5-methoxycarbonyl-2-pyrrylmethyl)-7β-phenylacetyl-amino-ceph-2-em-4ξ-carboxylic acid, the mixture is stirred for 30 minutes at room temperature and evaporated to dryness under reduced pressure. The residue is triturated with a 1:1-mixture of petroleum ether and diethyl ether and the residue chromatographed on 200 g of silica gel; elution is carried out with methylene chloride containing 5% of ethyl acetate, fractions of 200 ml being taken. Fractions 8–10 are combined and chromatographed once more on silica gel. Elution is performed with 50 ml fractions of methylene chloride containing 10% ethyl acetate. Fractions 1–5 contain the almost pure 3-(5-methoxycarbonyl-2-pyrrylmethyl)- 7β-phenylacetyl-amino-ceph-2-em-4ξ-carboxylic acid diphenylmethyl ester; thin-layer chromatogram (silica gel): Rf = 0.68 (system toluene/ethyl acetate 1:1) and Rf = 0.52 (system toluene/acetone 4:1).

EXAMPLE 24:

A solution of 1.5 ml of thioanisol in 10 ml of trifluoroacetic acid is treated with 1.17 g of 3-acetyloxymethyl-7β-phenylacetyl-amino-ceph-2-em-4ξ-carboxylic acid and the mixture is left to stand for 30 minutes at room temperature. After diluting the mixture with an equal volume of toluene, the volatile fractions are evaporated under reduced pressure. The residue is partitioned between ethyl acetate and a 10% aqueous dipotassium hydrogen phosphate solution (pH = 7.5). The layers are separated; the aqueous phase is washed several times with ethyl acetate, adjusted to pH 2.5 with 20% aqueous phosphoric acid and extracted with ethyl acetate. The resulting organic extracts are washed with water and a saturated aqueous sodium chloride solution, dried over magnesium sulphate and evaporated under reduced pressure, to yield the 3-(4-methylthio-benzyl)- 7β-phenylacetyl-amino-ceph-2-em-4ξ-carboxylic acid diphenylmethyl ester, which without purification.

The above crude product is dissolved in 20 ml of ethyl acetate and treated with 0.6 g of diphenyldiazomethane in 10 ml of ethyl acetate. The solution is left to stand for 60 minutes at room temperature, then evaporated to dryness under reduced pressure, and the residue is triturated with petroleum ether. The solid residue is chromatographed on 30 g of silica gel. Elution is carried out with 100 ml fractions of methylene chloride and from fractions 5–7 is obtained the 3-(4-methylthio-benzyl)-7β-phenylacetyl-amino-ceph-2-em-4ξ-carboxylic acid diphenylmethyl ester, which after recrystallisation from ethyl acetate melts at 161°-162°; thin-layer chromatogram (silica gel): Rf = 0.80 (system toluene/ethyl acetate 1:1) and Rf = 0.71 (system toluene/acetone 4:1); infrared absorption spectrum (in mineral oil): characteristic bands at 2,99μ, 5,63μ, 5,77μ, 6,02μ and 6,53μ.

EXAMPLE 25:

A mixture of 0.40 g of 3-acetyloxymethyl-7β-phenylacetyl-amino-ceph-2-em-4ξ-carboxylic acid and 0.515 g of acetylacetone is covered with 3 ml of trifluoroacetic acid; the mixture is left to stand for 15 minutes at room temperature and evaporated to dryness under reduced pressure. The residue is partitioned between a 10% aqueous dipotassium hydrogen phosphate solution and ethyl acetate. The organic phase is washed with the aqueous dipotassium hydrogen phosphate solution and the organic solutions are discarded. The combined aqueous phases are covered with ethyl acetate, and acidified with 20% aqueous phosphoric acid; the aqueous layer is extracted several times with ethyl acetate and the organic solutions are combined, washed until neutral, dried over sodium sulphate and evaporated under reduced pressure. The resulting amorphous 3-(2,2-diacetylethyl)-7β-phenylacetyl-amino-ceph-2-em-4ξ-carboxylic acid is almost a uniform substance; thin-layer chromatogram (silica gel): Rf = 0.62 (system n-butanol/ethanol/water 40:10:50), Rf = 0.66 (system: ethyl acetate/pyridine/acetic acid/water 62:21:6:11) and Rf = 0.62 (system: ethyl acetate/n-butanol/pyridine/acetic acid/water 42:21:21:6:10).

EXAMPLE 26

A solution of 0.390 g of 3-acetyloxymethyl-7β-phenylacetyl-amino-ceph-2-em-4ξ-carboxylic acid and 0.670 g of 1-benzothiophene in 2 ml of trifluoroacetic acid is stirred for 15 minutes at room temperature, then diluted with 2 ml of toluene. The mixture is evaporated under reduced pressure, the residue is treated with 30 ml of a 10% aqueous dipotassium hydrogen phosphate solution and extracted with 3 × 50 ml of ethyl acetate. The organic extracts are washed with a saturated aqueous sodium chloride solution, dried over sodium sulphate and evaporated under a water jet vacuum. An oily residue is obtained from which the excess 1-benzthiophene is removed at 50° under a high vacuum. The residue is crystallized from methanol and ethyl acetate to yield the 3-(3-benzothienylmethyl)-7β-phenylacetyl-amino-ceph-2-em-4ξ-carboxylic acid in the form of white crystals, m.p. 178°-180°; thin-layer chromatogram (silica gel): Rf = 0.77 (system: n-butanol/acetic acid/water 75:7.5:21), Rf = 0.62 (system: n-butanol/acetic acid/water 67:10:23) and Rf = 0.60 (system: ethyl acetate/pyridine/acetic acid/water 62:21:6:11); infrared absorption spectrum (in mineral oil): characteristic bands at 3,05μ, 3,68μ, 5,67μ, 5,75μ (shoulder), 6,04μ and 6,55μ.

EXAMPLE 27:

A solution of 3.52 g of 7β-phenylacetyl-amino-3-trifluoroacetyloxymethyl-ceph-2-em-4ξ-carboxylic acid and 2.4 g of 1-pyrrolidino-cyclohxane (b.p. 107°/10 mm Hg) in 400 ml of absolute benzene is heated for 5 minutes under reflux. The reaction solution, which contains the 7β-phenylacetyl-amino-3-[2-(1-pyrrolidino)-cyclohex-1-enyl-methyl]-ceph-2-em-4ξ-carboxylic acid, is cooled and, after addition of 80 ml of 2N hydrochloric acid and 200 ml of acetone, is left to stand for 1 hour at room temperature. After diluting the mixture with 200 ml of water and raising the pH value to 7.5 by treatment with an aqueous tripotassium phosphate solution, the acetone is almost completely evaporated off under reduced pressure. The neutral fractions in the residue are removed by extraction with ethyl acetate and discarded. The aqueous phase is covered with fresh ethyl acetate and acidified with 20% aqueous phosphoric acid to pH 2.5. The aqueous layer is separated, re-extracted with ethyl acetate and discarded. The organic extracts are washed with a saturated aqueous sodium chloride solution and dried over magnesium sulphate. After evaporation of the solvent under reduced pressure, the 3-(2-oxo-cyclohexyl)-methyl-7β-phenylacetyl-amino-ceph-2-em-4ξ-carboxylic acid is obtained in amorphous form; thin-layer chromatogram (silica gel): Rf = 0.55 (system: n-butanol/acetic acid/water 67:10:23) and Rf = 0.43 (system: n-butanol/ethanol/water 40:10:50), (detection with ultraviolet light or iodine).

EXAMPLE 28

A mixture of 4.6 g of an approximately 1:3-mixture of 3-acetyloxymethyl-7β-formylamino-ceph-3-em-4-carboxylic acid and 3-acetyloxymethyl-7β-formylamino-ceph-2-em-4ξ-carboxylic acid (prepared as described below), 7 ml of thiophene and 28 ml of trifluoroacetic acid is allowed to stand for 20 minutes at room temperature and then evaporated to dryness while repeatedly adding toluene. The semi-crystalline residue is dissolved in hot methyl acetate and the solution diluted with methylene chloride and cyclohexane, whereupon a slightly yellow, coarsely crystalline precipitate forms, which is filtered off and dried, to yield the 7β-formylamino-3-(2-thenyl)-ceph-2-em-4ξ-carboxylic acid, m.p. 164°-166° (decomposition starts at 160°); thinlayer chromatogram (silica gel); Rf = 0.60 (system: n-butanol/acetic acid/water 75:7.5:21), Rf = 0.47 (system: n-butanol/ethanol/water 40:10:50), Rf = 0.66 (system: n-butanol/acetic acid/water 40:10.40) and Rf = 0.55 (system: ethyl acetate/pyridine/acetic acid/water 62:21:6:11); ultraviolet absorption spectrum (in 95% ethanol):$\lambda_{max}$ = 234 mμ ($\epsilon$ = 13900) and $\lambda_{max}$ = 216 mμ ($\epsilon$ =10900); infrared absorption spectrum (in mineral oil): characteristic bands at 3,08μ, 3,87μ, 5,68μ, 5,80μ, 6,04μ, 6,52μ 7,07μ, 8,06μ, 8,23μ, 8,53μ, 8,69μ, 9,65μ, 9,74μ, 11,79μ and 14,24μ. A further quantity of the desired product is obtained if the mother liquor is chromatographed on 50 times its weight of silica gel; the 7β-formulamino-3-(2-thenyl)-ceph-2-em-4ξ-carboxylic acid is eluted with a 3:1-mixture of methylene chloride and ethyl acetate.

The starting material can be manufactured as follows:

A solution of 5 g of 3-acetyloxymethyl-7β-formylamino-ceph-3-em-4-carboxylic acid in 20 ml of pyridine and 2 ml of dimethylsulphoxide is treated with 2 ml of acetic acid anhydride and the mixture left to stand for 2 hours at room temperature. The brown reaction mixture is evaporated to dryness several times while adding absolute toluene and the residue is covered with ethyl acetate. After acidifiying with 20% aqueous phosphoric acid and saturating with sodium chloride, the layers are separated. The aqueous phase is re-extracted with ethyl acetate and the combined organic solutions are repeatedly washed with a saturated aqueous sodium chloride solution, dried over magnesium sulphate, treated with an active charcoal preparation and evaporated under reduced pressure. An approximately 1:3-mixture of 3-acetyloxymethyl-7β-formylamino-ceph-3-em-4-carboxylic acid and 3-acetyloxymethyl-7β-formylamino-ceph-2-em-4ξ-carboxylic acid is obtained, which is used without further purification.

EXAMPLE 29:

16.0 Grams of 3-acetyloxymethyl-7β-[N-2,2,2-trichloroethoxycarbonyl-D-(α)-phenylglycyl]-amino-ceph-2-em-4ξ-carboxylic acid are treated with 30 ml of thiophene and 120 ml of trifluoroacetic acid and the reaction mixture is left to stand for 20 minutes at room temperature, then evaporated to dryness several times while adding toluene on each occasion. The partially crystalline residue is charged onto 800 g of silica gel (column; washed with concentrated hydrochloric acid), and the 3-(2-thenyl)-7β-[N-2,2,2-trichloroethoxycarbonyl-D-(α)-phenylglycyl]-amino-ceph-2-em-4ξ-carboxylic acid is eluted with a 9:1-mixture of methylene chloride and methyl acetate. The fractions which are pure according to thin-layer chromatography are combined and crystallised from a mixture of acetone, methyl acetate and cyclohexane; the product crystallises in the form of colourless needles and melts (after heating from 195°) at 202.5° – 203.5°; $[\alpha]_D^{20}$ =+245° ± 1° (c = 1.013 in dioxane); thin-layer chromatogram (silica gel): Rf = 0.73 (system: n-butanol/acetic acid/water 75:7.5:21), Rf = 0.66 (system: n-butanol/ethanol/water 40:10:50), Rf = 0.80 (system: n-butanol/acetic acid/water 40:10:40) and Rf = 0.79 (system: ethyl acetate/pyridine/acetic acid/water 62:21:6:11).

The starting material can be manufactured as follows:

A suspension of 20.0 g of N-2,2,2-trichloroethoxycarbonyl-D-(α)-phenyl-glycine in 400 ml of a 1:1-mixture of tetrahydrofuran and acetonitrile is treated with 8.5 ml of triethylamine. After cooling to −10°, 8.0 ml of chloroformic acid isobutyl ester is added dropwise under anhydrous conditions and the mixture is stirred for 15 minutes at −10°. Upon addition of a further 100 ml of absolute acetonitrile, a clear solution is obtained that is treated dropwise with a mixture of 16.0 g of 7β-amino-ceph-3-em-4-carboxylic acid and 8.1 ml of triethylamine in 200 ml of 50% aqueous tetrahydrofuran, the dropwise addition being so performed that the internal temperature does not rise above 0°. The reaction mixture is further stirred for 30 minutes at 0°and for 90 minutes at room temperature. The bulk of the solvent is then evaporated under reduced pressure. The residue is taken up in 200 ml of a 0.5 molar aqueous dipotassium hydrogen phosphate solution and 200 ml of ethyl acetate and filtered with the aid of a glass-filter funnel having a coating of diatomaceous earth. The layers of the filtrate are separated; the organic phase is re-extracted with a further amount of the dipotassium hydrogen phosphate solution and discarded. The aqueous phases are washed with ethyl acetate, covered with fresh ethyl acetate and acidified with concentrated phosphoric acid to pH 2. The organic phase is separated off and repeatedly washed with a concentrated aqueous sodium chloride solution. The aqueous phases are reextracted with 2 × 150 ml of ethyl acetate and discarded. The combined organic extracts are dried over sodium sulphate and freed from solvent under reduced pressure. The residue is chromatographed on 600 g of silica gel. Unchanged N-2,2,2-trichloroethoxycarbonyl-D-(α)-phenylglycine is eluted with a 4:1-mixture of toluene and ethyl acetate. Using 7:3- to 1:1-mixtures of toluene and ethyl acetate the 3-acetyloxymethyl-7-[N-2,2,2-trichloroethoxycarbonyl-D-(α)-phenylglycyl]-amino-ceph-3-em-4-carboxylic acid is eluted, which crystallises from a mixture of methylene chloride, diethyl ether and toluene. The pure substance is isolated in the form of a gelatinous precipitate, which after drying yields a colourless powder; thin-layer chromatogram (silica gel; development with iodine vapour): Rf = 0.61 (system: n-butanol/acetic acid/water 75:7.5:21), Rf = 0.44 (system: n-butanol/ethanol/water 40:10:50), Rf = 0.67 (system: n-butanol/acetic acid/water 40:10:40), Rf = 0.64 (system: ethyl acetate/pyridine/acetic acid/water 62:21:6:11) and Rf = 0.70 (system: ethyl acetate/n-butanol/pyridine/acetic acid/water 42:21:21:6:10).

If a small amount of the above 3-acetyloxymethyl-7-[N-2,2,2-trichloroethoxycarbonyl-D-(α)-phenylglycyl]-amino-ceph-3-em-4-carboxylic acid is treated with diphenyldiazomethane in a 4:1-mixture of dioxane and methanol, the 3-acetyloxymethyl-7-[N-2,2,2-trichloroethoxycarbonyl-D-(α)-phenylglycyl]-amino-ceph-3-em-4-carboxylic acid diphenyl-methyl ester is obtained, which after recrystallisation from a mixture of methylene chloride, diethyl ether and cyclohexane melts at 153°–154.5°(uncorr.); $[\alpha]_D^{20} = -14° \pm 1°$ (c = 1.155 in chloroform).

A solution of 8.9 g of 3-acetyloxymethyl-7-[N-2,2,2-trichloroethoxycarbonyl-D-(α)-phenylglycyl]-amino-ceph-3-em-4-carboxylic acid in 40 ml of pyridine is treated with 3.4 ml of acetic anhydride and left to stand for 18 hours at 4°. The brown reaction solution is evaporated to dryness while adding absolute toluene and freed from volatile fractions under a high vacuum. The residue is chromatographed on 50 times its weight of silica gel (washed with concentracted hydrochloric acid). The 3-acetyloxymethyl-7β-[N-2,2,2-trichloroethoxycarbonyl-D-(α)-phenylglycyl]-amino-ceph-2-em-4ξ-carboxylic acid is eluted with methylene chloride, containing 15% of methyl acetate and crystallised from a mixture of ethyl acetate and cyclohexane, m.p. 164.5°–165.5° (uncorr.; with decomp.); $[\alpha]_D^{20} = +247°$ ± 1° (c = 1.037 in dioxane); thin-layer chromatogram (silica gel): Rf = 0.64 (system: n-butanol/acetic acid/water 75:7.5:21), Rf = 0.48 (system: n-butanol/ethanol/water 40:10:50), Rf = 0.63 (system: n-butanol/acetic acid/water 40:10:40) and Rf = 0.64 (system: ethyl acetate/pyridine/acetic acid/water 62:21:6:11); ultraviolet absorption spectrum (in 95% ethanol): strong terminal absorption and shoulders at 247 m$\mu$ ($\epsilon$ = 7200) and 230 m$\mu$ ($\epsilon$ = 10400); infrared absorption spectrum (in mineral oil); characteristic bands at 2,98$\mu$, 5,67$\mu$, 5,73$\mu$, 5,77$\mu$, 5,86$\mu$, 6,00$\mu$, 6,54$\mu$, 7,08$\mu$, 7,80$\mu$, 8,05$\mu$, 8,20$\mu$, 8,50$\mu$, 8,98$\mu$, 9,52$\mu$, 9,63$\mu$ and 11,98$\mu$.

The corresponding 3-acetyloxymethyl-7β-[N-2,2,2-trichloroethoxycarbonyl-D-(α)-phenylglycyl]-amino-ceph-2-em-4ξ-carboxylic acid-diphenylmethylester melts at 127.5°–129°(uncorr.); $[\alpha]_D^{20} = +224°$ ± 1° (c = 1.048 in chloroform); thin-layer chromatogram (silica gel): Rf = 0.03 (system: toluene/ethyl acetate 1:1), Rf = 0.60 (system: toluene/ethyl acetate 2:1); Rf = 0.56 (system: toluene/acetone 4:1) and Rf = 0.29 (system: toluene/acetone 9:1); ultraviolet absorption spectrum (in 95% ethanol): $\lambda_{max}$ = 249 m$\mu$ ($\epsilon$ = 8550) and $\lambda_{min}$ = 241 m$\mu$ ($\epsilon$ = 7900); infrared absorption spectrum (in mineral oil): characteristic bands at 2,97$\mu$, 5,58$\mu$, 5,74$\mu$, 5,84$\mu$, 5,98$\mu$, 6,52$\mu$, 7,37$\mu$, 7,43$\mu$, 8,07$\mu$, 8,20$\mu$, 8,32$\mu$, 8,54$\mu$, 9,04$\mu$, 13,24$\mu$, 13,91$\mu$, 14,17$\mu$ and 14,38$\mu$.

EXAMPLE 30:

A solution of 60.0 g of 3-acetyloxymethyl-7β-(D-5-diphenylmethoxycarbonyl-5-phthalimido-valeroyl-amino)-ceph-2-em-4ξ-carboxylic acid-diphenylmethyl ester in approximately 200 ml of absolute pyridine is left to stand in the dark for 3½ days at room temperature under nitrogen, then evaporated to dryness several times while adding toluene on each occasion. The residue is dissolved in 150 ml of freshly distilled furan-2-carboxylic acid methyl ester and treated with 300 ml of absolute trifluoroacetic acid. The mixture is left to stand for 60 minutes at room temperature and evaporated to dryness under reduced pressure and the residue is evaporated to dryness several times with toluene. The crude product is partitioned between 3 portions each of a 0.5 molar aqueous dipotassium hydrogen phosphate solution and ethyl acetate. The organic extracts are discarded with the neutral fractions. The aqueous extracts are covered with fresh ethyl acetate and acidified by addition of 20% aqueous phosphoric acid to pH 2. The aqueous phase is separated, saturated with sodium chloride, re-extracted with 2 additional portions of ethyl acetate and discarded. The organic extracts are washed several times with a saturated aqueous sodium chloride solution, dried over magnesium sulphate and freed from solvent under reduced pressure. The brownish, amorphous crude product is chromatographed on 700 g of silica gel (purified with concentrated hydrochloric acid) and the 7β-(D-5-carboxy-5-phthalimido-valeroyl-amino)-3-(5-methoxycarbonyl-furfuryl)-ceph-2-em-4ξ-carboxylic acid is eluted with methylene chloride, containing 40–50% of ethyl acetate.

The fractions, which contain the desired product according to thin-layer chromatogram on silica gel (plates) in the system n-butanol/acetic acid/water 67:10:23, are dissolved in 200 ml of a 4:1-mixture of dioxane and methanol and esterified for 3 hours at room temperature with an excess solution of diphenyl-diazomethane in diethyl ether. The crude product is purified by means of a rapid chromatogram on silica gel (elution with methylene chloride containing 15–30% of ethyl acetate), thus yielding the amorphous 7β-(D-5-diphenylmethoxycarbonyl-5-phthalimido-valeroyl-amino)-3-(5-methoxycarbonyl-furfuryl)-ceph-2-em-4ξ-carboxylic acid-diphenylmethyl ester.

EXAMPLE 31:

A mixture of 9.73 g of 3-acetyloxymethyl-7β-phenylacetyl-amino-ceph-2-em-4ξ-carboxylic acid and 10 g of 4-fluorophenol is dissolved in 50 ml of trifluoroacetic acid and the clear solution is evaporated several times while adding toluene on each occasion. The residue is chromatographed on 300 g of silica gel. The excess 4-fluorophenol is eluted with methylene chloride and the 2-(5-fluoro-2-hydroxybenzyl)-7β-phenylacetylamino-cepth-2-em-4ξ-carboxylic acid with a 4:1-mixture of methylene chloride and ethyl acetate and recrystallised from ethyl acetate, m.p. 185°–187°; thin-layer chromatogram (silica gel): Rf = 0.55 (system: n-butanol/acetic acid/water 75:7.5:21), Rf = 0.73 (system: n-butanl/ethanol/water 40:10:50) and Rf = 0.84 (system: chloroform/methanol 1:1).

EXAMPLE 32

A solution of 12.0 g. of 3-acetyloxymethyl-7β-[N-2,2,2-trichloroethoxycarbonyl-D-(α)-phenylglycyl]-amino-ceph-3-em-4-carboxylic acid in 54 ml of pyridine is treated with 4.58 ml of acetic anhydride and left to stand for 16 hours at 4°. The reaction mixture is evaporated to dryness several times while adding absolute toluene. The residue is dissolved in ethyl acetate and adjusted to pH 2 with 1N hydrochloric acid. The organic phase is washed with a saturated aqueous sodium chloride solution, dried over sodium sulphate and evaporated to dryness under reduced pressure. The residue is treated with 24.5 ml of anisol and 89 ml of trifluoroacetic acid and the reaction mixture is left to stand for 20 minutes, then evaporated to dryness several times while adding toluene on each occasion. The partially crystalline residue is chromatographed on 600 g of silica gel (purified with concentrated hydrochloric acid; column). The approximately 1:1-mixture of 3-(2-methoxybenzyl)-7β-[N-2,2,2-trichloroethoxycarbo-nyl-D-(α)-phenylglycyl]-amino-ceph-2-em-4ξ-carboxylic acid and the corresponding 3-(4-methoxybenzyl)-7β-[N-2,2,2-trichloroethoxycarbonyl-D-(α)-phenylglycyl]-amino-ceph-2-em-4ξ-carboxylic acid is eluted with a 9:1-mixture of methylene chloride and ethyl acetate. The fractions, that are pure according to thin-layer chromatography, are combined and recrystallised from a mixture of acetone and cyclohexane, m.p. 215°–222° (with decomp.); ultraviolet absorption spectrum (in ethanol): $\lambda_{max}$ = 229,5 mμ (ε = 12680) and $\lambda_{shoulder}$ = 252 mμ (ε = 5800); infrared absorption spectrum (potassium bromide): characteristic bands at 2,90μ, 3,00μ, 3,30μ, 3,38μ, 3,53μ, 3,91μ, 5,66μ, 5.75μ, 5,85μ, 6,00μ, 5,61μ, 7,51μ, 8,00μ, 8,20μ, 8,49μ, 8,97μ, 9,60μ, 9,69μ, 12,30μ, 13,25μ, 13,82μ and 14,33μ; thin-layer chromatogram (silica gel): Rf = 0.61 (system: n-butanol/ethanol/water 40:10:50), Rf = 0.74 (system: n-butanol/acetic acid/water 75:7.5:21) and Rf = 0.86 (system: ethyl acetate/pyridine/acetic acid/water 62:21:6:11).

EXAMPLE 33:

If in the process of Example 29 3-acetyloxymethyl-7β-[N-2-bromoethoxycarbonyl-D-(α)-phenyl-glycyl]-amino-ceph-2-em-4ξ-carboxylic acid (obtained by isomerisation of 3-acetyloxymethyl-7G2s-[N-2-bromoethoxycarbonyl-D-(α)-phenylglycyl]-amino-ceph-3-em-4-carboxylic acid) is used instead of 3-acetyloxymethyl-7β-[N-2,2,2-trichloroethoxycarbo-nyl-D-(α)-phenylglycyl]-amino-ceph-2-em-4ξ-carboxylic acid and it is reacted with 2-furanacetic acid 2-bromoethyl ester and trifluoroacetic acid, the 3-[5-(2-bromoethoxycarbonyl)-methyl-furfuryl]-7β-[N-2-bromoethoxycarbonyl-D-(α)-phenylglycyl]-amino-ceph-2-em-4ε-carboxylic acid is obtained, which after recrystallisation from a mixture of methylene chloride and cyclohexane melts at 103°–105°; thin-layer chromatogram (silica gel): Rf = 0.62 (system: n-butanol/acetic acid/water 75:7.5:21) and Rf = 0.52 (system: n-butanol/ethanol/water 40:10:50); ultraviolet absorption spectrum (in ethanol): $\lambda_{max}$ = 237 mμ (ε = 8950) and $\lambda_{shoulder}$ = 254.5 mμ (ε = 5270); infrared absorption spectrum (methylene chloride): characteristic bands at 2,93μ, 3,02μ, 3,43μ, 5.60μ, 5,65μ, 5,75μ, 5,90μ, 601μ, 6,69μ, 7,24μ, 7,51μ, 8,22μ, 8,51μ, 9,82μ and 12,58μ.

The 3-acetyloxymethyl-7β-[N-2-bromoethoxycarbonyl-D-(α)-phenylglycyl]-amino-ceph-2-em-4ξ-carboxylic acid used as starting material can be manufactured as follows:

22.7 Grams of D-(α)-phenylglycine are suspended in 300 ml of water and brought into solution by addition of 80 ml of 2N aqueous sodium hydroxide. The clear solution is treated with 150 ml of diethyl ether and cooled to 0° to −5°. At this temperature, and while stirring vigorously, 21.8 ml (37.5 g) of 2-bromoethoxycarbonyl chloride in 200 ml of dioxane and 100 ml of a 2N aqueous sodium hydroxide solution are added dropwise simultaneously within 1 hour. The reaction solution is further stirred for 1 hour at 0° and treated with 1000 ml of diethyl ether. After brief stirring, the layers are separated; the organic phase is washed with 50 ml of water and discarded. The aqueous fractions are covered with 500 ml of ethyl acetate, acidified to pH 2.5 with 20% aqueous phosphoric acid and saturated with sodium chloride; the aqueous layers are re-extracted with 2 × 150 ml of ethyl acetate and discarded. The organic extracts are washed with 4 portions of saturated aqueous sodium chloride solution (50 ml on each occasion), dried over magnesium sulphate and freed from solvent under reduced pressure.

The residue is dissolved in methylene chloride while heating and treated with cyclohexane. The mixture is left to stand at approximately 4°, whereupon a thick broth of needle-shaped crystals forms, which are collected by suction filtration while cooling. The colourless precipitate is washed with a 1:9-mixture of methylene chloride and cyclohexane and with pentane, and dried to constant weight in a vacuum exsiccator, thus yielding 2-bromoethoxycarbonyl-D-(α)-phenylglycine, m.p. 99–100° (uncorr.). From the filtrate, it is possible to obtain a further amount of yellow crystals, m.p. 83°–88°, which can be crystallised again, m.p. 96°–98°. The analysis sample melts unchanged at 99°–100° (uncorr.) after further crystallisation from the methylene chloride-cyclohexane mixture.

A solution of 30.2 g of 2-bromoethoxycarbonyl-D-(α)-phenylglycine in 500 ml of absolute tetrahydrofuran is treated with 13.2 ml of absolute triethylamine and cooled to −10°. While stirring thoroughly, 13.5 ml of chloroformic acid isobutyl ester are added under anhydrous conditions. The resulting white suspension is further stirred for 15 minutes at −10°. In the meantime, 32.6 g of 7-amino-cephalosporanic acid (approx. 90%) are suspended in 400 ml of 50% aqueous tetrahydrofuran and brought into solution by addition of 15.8 ml of triethylamine. Upon cooling to 0°, this solution is passed into the mixed anhydride. The reaction mixture is stirred for 1 hour at 0°–10° and for a further hour at room temperature (20°–25°C). The tetrahydrofuran is then evaporated under reduced pressure, the residue is diluted with 300 ml of water and extracted with 200 ml of ethyl acetate. The organic phase is separated and re-extracted with 100 ml of a 0.5% aqueous dipotassium hydrogen phosphate solution. A quantity of undissolved material is removed by filtration. The ethyl acetate extracts are dried over magnesium sulphate and evaporated. According to thin-layer chromatogram, the residue contains only a small amount of desired material in addition to nonpolar by-products and is discarded. The aqueous extracts are covered with 400 ml of ice-cooled ethyl acetate and acidified to pH 2.5 with approximately 5 molar aqueous phosphoric acid. The precipitate that separates out in the process is filtered off, washed with water and ethyl acetate and dried; according to chromatogram on silica gel plates, it is almost pure 7-amino-cephalosporanic acid. The aqueous phase of the filtrate is separated, re-extracted with 2 × 300 ml of ethyl acetate and discarded. The organic extracts are washed with 300 ml of water and 300 ml of saturated aqueous sodium chloride solution, dried over anhydrous magnesium sulphate and freed from solvent under reduced pressure. The residue is dried under a high vacuum to yield a slightly yellowish foam, which is as single substance according to thin-layer chromatography. This foam is dissolved in ethyl acetate with addition of acetone and chromatographed on a column of 800 g of silica gel. Elution is effected with a 9:1-mixture of ethyl acetate and methanol; nonpolar by-product and the yellow colouration are removed in the first runnings. The 3-acetyloxymethyl-7β-[N-2-bromoethoxycarbonyl-D-(α)-phenyl-glycyl]-amino-ceph-2-em-4ξ-carboxylic acid, , which is pure according to thin-layer chromatography, is crystallised from ethyl acetate and recrystallised from a mixture of acetone, methyl acetate and cyclohexane and dried under a high vacuum at room temperature, m.p. 159.5°–161° (with decomp.; uncorr.); $[\alpha]_D^{20}$ = +21° ± 21° (c = 0.989 in methanol).

The 2-furanacetic acid 2-bromoethyl ester used as starting material can be manufactured as follows:

A solution of 15.12 g of furanacetic acid in 120 ml of methylene chloride is cooled to 0°; 15.6 g of chloromethylene-dimethylammonium chloride are added and the mixture is stirred for 10 minutes while cooling with ice. A solution of 30 g of 2-bromoethanol and 19.4 ml of pyridine in 60 ml of methylene chloride is then added dropwise with stirring and the reaction mixture is left to stand for 20 minutes while cooling with ice and for 1 hour at room temperature. The solution is extracted three times with a 5% aqueous sodium bicarbonate solution and once with a saturated aqueous sodium chloride solution, dried over sodium sulphate and distilled under reduced pressure. The 2-furanacetic acid 2-bromoethyl ester is obtained at 76°/0.25 mm; infrared absorption spectrum (in methylene chloride): characteristic bands at 3,44μ, 5,72μ, 6,10μ, 7,49μ, 8,20μ, 8,68μ, 9,31μ and 9,86μ.

EXAMPLE 34:

If in Example 1 the 2-furanacetic acid 2-bromoethyl ester is used instead of the anisole, the 3-[5-(2-bromoethoxycarbonyl)-methyl-furfuryl]-7β-phenylacetylamino-ceph-2-em-4-carboxylic acid is obtained, which after recrystallisation from a mixture of methylene choride and cyclohexane melts at 131°–132°; thin-layer chromatogram (silica gel): Rf = 0.75 (system: n-butanol/acetic acid/water 75:7.5:21) and Rf = 0.58 (system: n-butanol/ethanol/water 40:10:50:); ultraviolet absorption spectrum (in ethanol): $\lambda_{max}$ = 222 mμ (ε = 15050) and $\lambda_{shoulder}$ = 250 mμ (ε = 6660); infrared absorption spectrum (in methylene chloride): characteristic bands at: 2,90μ, 3,39μ, 5,57μ, 5,70μ, 5,89μ, 6,02μ, 6,60μ, 7,22μ, 7,58μ, 8,22μ, 8,57μ, 8,80μ, 11,43μ and 12,54μ.

EXAMPLE 35:

If in the process of Example 29, the 3-acetyloxymethyl-7β-[N-2-bromoethoxycarbonyl-D-(α)-phenyl-glycyl]-amino-ceph-2-em-4ξ-carboxylic acid is instead of the 3-acetyloxymethyl-7β-[N-2,2,2-trichloroethoxycarbonyl-D-(α)-phenylglycyl]-amino-ceph-2-em-4G2c-carboxylic acid and is reacted with phenol and trifluoroacetic acid, a 1:2-mixture of 7G2s-[N-2-bromoethoxycarbonyl-D-(α)-phenyl-glycyl]-amino-3-(2-hydroxybenzyl)-ceph-2-em-4G2c-carboxylic acid and the 7β-[N-2-bromoethoxycarbonyl-D-(α)-phenylglycyl]-amino-3-(4-hydroxybenzyl)-ceph-2-em-4ξ-carboxylic acid and is reacted with can be separated by crystallisation from a mixture of methylene chloride, acetone and cyclohexane. The 7β-[N-2-bromoethoxycarbonyl-D-(α)-phenyl-glycyl]-amino-3-(2-hydroxybenzyl)-ceph-2-em-4ξ-carboxylic acid and the 7β-[N-2-bromoethoxycarbo-from a mixture of methylene chloride, acetone and cyclohexane; thin-layer chromatogram (silica gel): Rf = 0.53 (system: chloroform/methanol 1:1) and Rf = 0.35 (system: n-butanol/acetic acid/water 75:7.5:21); infrared absorption spectrum (in mineral oil): characteristic bands at 3.08μ, 5,68μ , 5.76μ, 5,85μ, 5,97μ, 6,47μ, 6,88μ, 7,27μ, 8,20μ, 8,51μ, 9,59μ, 13,75μ and 14,38μ.

EXAMPLE 36

The residue obtained according to the process below and which contains an approximately 3:1-mixture of 3-acetyloxymethyl-7β-[N-2-bromoethoxycarbonyl- D-(α)-phenylglycyl]-amino-ceph-2-em-4ξ-carboxylic acid and 3-acetyloxymethyl- 7β-[N-2-bromoethoxycarbonyl-D-(α)-phenylglycyl]-amino-ceph-3-em-4-carboxylic acid is dissolved in 124 g of freshly distilled furan-2-carboxylic acid methyl ester and 250 ml of trifluoroacetic acid. After a reaction time of 20 minutes the mixture is evaporated to dryness several times under a high vacuum while repeatedly adding absolute toluene. The residual foam is dissolved in 300 ml of ethyl acetate and 500 ml of a 0.5 molar aqueous dipotassium hydrogen phosphate solution. The pH of the mixture is raised to 8.5 by addition of a 50% aqueous tripotassium phosphate solution. The organic phase is separated, re-extracted with 2 × 100 ml of the aqueous dipotassium hydrogen phosphate solution and discarded. The aqueous phase is shaken out with 2 × 100 ml of ethyl acetate, covered with 300 ml of fresh ethyl acetate and acidified with 20% aqueous phosphoric acid to pH 2.5. The aqueous phase is separated, re-extracted with 2 additional portions of ethyl acetate after saturation with sodium chloride and discarded. The organic extracts are washed several times with a saturated aqueous sodium chloride solution, dried over magnesium sulphate and freed from solvent under reduced pressure.

The residue is taken up in acetone and treated with activated charcoal while heating. Upon evaporation of the acetone, the crude product is dissolved in warm ethyl acetate. On addition of cyclohexane, faintly yellow crystals begin to separate out; these are filtered off and dried, to give the 7β-[N-2-bromoethoxycarbonyl-D-(α)-phenylglycyl]-amino-3-(5-methoxycarbonyl-furfuryl)-ceph-2-em-4ξ-carboxylic acid. The mother liquors are chromatographed on 600 g of silica gel (purified with concentrated hydrochloric acid). The reaction product, which is a single substance according to thin-layer chromatography, is eluted with methylene chloride, containing 12–15% of ethyl acetate and crystallised from a mixture of acetone, ethyl acetate and cyclohexane. The analytical sample is crystallised once more from the same solvent system and dried for 22 hours under a high vacuum at 164°–164.5° (with decomp.; uncorr.); $[\alpha]_D^{20} = 198° \pm 1°$ (c = 1.007 in dioxane); thin-layer chromatogram (silica gel, plates with fluorescence indicator; detection with ultraviolet light $\lambda = 254$ mμ and iodine vapour): Rf = 0.72 (system:n-butanol/acetic acid/water 75:7.5:21), Rf = 0.43 (system: n-butanol/ethanol/water 40:10:50), Rf = 0.74 (system: n-butanol/acetic acid/water 44:12:44) and Rf = 0.78 (system: ethyl acetate/pyridine/acetic acid/water 62:21:6:11); ultraviolet absorption spectrum (in 95% aqueous ethanol): $\lambda_{max} = 261$ mμ (ε = 18550) and $\lambda_{min} = 232$ mμ (ε = 11650); infrared absorption spectrum (in mineral oil): characteristic bands at 3,03μ, 3,25μ, 5,68μ, 5,77μ, 5,80μ (shoulder), 5,89μ, 6,02μ, 6,50μ, 7,59μ, 7,96μ, 8,04μ, 8,21μ, 8,51μ, 8,76μ, 9,82μ and 13,17μ.

The starting material can be manufactured as follows: A solution of 44.0 g of 3-acetyloxymethyl-7β-[N-2-bromoethoxycarbonyl-D-(α)-phenylglycyl]-amino-ceph-3-em-4-carboxylic acid in 200 ml of absolute pyridine is left to stand for 2 hours at room temperature after addition of 17 ml of acetic acid anhydride. The dark reaction solution is evaporation to dryness under a high vacuum. The residue, which contains the 3-acetyloxymethyl-7β-[N-2-bromoethoxycarbonyl-D-(α)-phenylglycyl]-amino-ceph-2-em-4ξ-carboxylic acid, is partitioned between ethyl acetate and a 0.5 molar aqueous dipotassium hydrogen phosphate solution; the organic phase is re-extracted with the buffer solution and discarded. The aqueous phase is covered with fresh ethyl acetate and acidified to pH 2 with 20% aqueous phosphoric acid. The aqueous phase is separated, saturated with sodium chloride, reextracted with ethyl acetate and discarded. The organic extracts are washed with a saturated aqueous sodium chloride solution, dried over magnesium sulphate and freed from solvent under reduced pressure.

EXAMPLE 37:

A solution of 1.50 g of 3-(4-methoxy-benzyl)-7-(N-phenylacetyl-amino)ceph-2-em-4ξ-carboxylic acid, containing a small quantity of 3-(2-methoxy-benzyl)-7-(N-phenylacetyl-amino)-ceph-2-em-4ξ-carboxylic acid, in 50 ml of a 4:1 mixture of dioxane and methanol, is treated with a solution of diphenyldiazomethane in cyclohexane, added in portions, until a red colour persists, and the mixture is left to stand for 3 hours at room temperature. The solvent is removed under reduced pressure and the residue is chromatographed on a column with 135 g of silica gel. Non-polar impurities are eluted with methylene chloride, and the desired product is eluted with methylene chloride containing 2% of acetic acid ethyl ester. The residue of the combined extract is recrystallised from a mixture of methylene chloride, 1,1,1-trichlorethane and cyclohexane, whereupon a product melting at 128° – 129°C (uncorrected) is obtained. Further recrystallisation from the same solvent mixture results in the enrichment of 3-(4-methoxy-benzyl)-7-(N-phenylacetyl-amino)-ceph-2-em-4ξ-carboxylic acid diphenylmethyl ester and the melting point rises to 145° – 145.5°C. (corrected; correction + 1.5°C). The pure 3-(4-methoxy-benzyl)-7β-(N-phenylacetyl-amino)-ceph-2-em-4ξ-carboxylic acid diphenylmethyl ester obtained after four recrystallisations is dried in a high vacuum at 35°C; $[\alpha]_D^{20} = +317° \pm 1°$ (c = 1.269 in chloroform); thin layer chromatogram (silica gel G; development with iodine vapour): Rf = 0.58 (system toluene/acetone, 4:1), Rf = 0.19 (system toluene/acetone, 19:1), Rf = 0.56 (system toluene/diethyl ether, 1:1), Rf = 0.31 (system toluene/acetic acid ethyl ester, 4:1), Rf = 0.38 (system toluene/acetic acid ethyl ester, 3:1) and Rf = 0.86 (system toluene/acetic acid ethyl ester); ultraviolet absorption spectrum (in 95% ethanol): $\lambda_{max} = 285$ mμ (ε = 1900), $\lambda_{shoulder} = 253$ mμ (ε = 8600) and strong end absorption; infrared absorption spectrum: characteristic bands in methylene chloride at 2.92μ, 5.61μ, 5.73μ, 5.93μ, 6.20μ, 6.62μ, 6.67μ (shoulder), 6.88μ, 8.48μ and 9.69μ, and in mineral oil at 2.99μ, 5,63μ, 5.77μ, 6.05μ, 6.56μ, 6.61μ, 7.42μ, 8.00μ, 8.33μ, 8.58μ and 9.71μ.

EXAMPLE 38

A solution of 5.1 g of the crude 3-(2,5-dimethoxybenzyl)-7-(N-phenylacetyl-amino)-ceph-2-em-4ξ-carboxylic acid in 100 ml of 4:1 mixture of dioxane and methanol is treated with a solution of diphenyldiazomethane in cyclohexane until a red colour persists. After 16 hours standing at room temperature, the mixture is evaporated to dryness under reduced pressure and the residue is chromatographed on silica gel containing 5% of watar. 3-(2,5-Dimethoxy-benzyl)-7-(N-phenylacetyl-amino)-ceph-2-em-4ξ-carboxylic acid diphenylmethyl ester is eluted with methylene chloride containing 3 – 4% of acetic acid methyl ester. The residue from the eluate is crystallised from a mixture of acetone and cyclohexane, melting point 145° – 146.5°C (uncorrected); $[\alpha]_D^{20} = + 268° \pm 1°$ (c = 1.018 in chloroform); thin layer chromatogram (silica gel; development with iodine vapour): Rf = 0.19 (system toluene/acetone, 19:1), Rf = 0.57 (system toluene/acetone, 4:1), Rf = 0.40 (system toluene/acetic acid ethyl ester, 4:1) and Rf = 0.56 (system toluene/diethyl ether, 1:1); ultraviolet absorption spectrum (in 95% strength non-denatured ethanol): $\lambda_{max}$ = 291 mµ ($\epsilon$ = 4550) and 250 mµ ($\epsilon$ = 6850), and $\lambda_{min}$ = 272 mµ ($\epsilon$ = 2350); infrared absorption spectrum: characteristic bands in methylene chloride at 2.98µ, 3.49µ, 5.60µ, 5.71µ, 5.91µ, 6.65µ, 7.56µ, 8.14µ, 8.45µ and 9.57µ, and in mineral oil at 2.98µ, 5.59µ, 5.75µ, 5.98µ, 6.02µ (shoulder), 6.53µ, 6.65µ and 8.12µ.

EXAMPLE 39

A solution of 10.9 g of 3-(4-methoxy-1-naphthylmethyl)-7β-phenylacetylamino-ceph-2-em-4ξ-carboxylic acid in 300 ml of methylene chloride is treated with 1.80 ml of pyridine, then successively with 2.50 ml of 2,2,2-trichloroethanol in 20 ml of methylene chloride and 4.95 g of dicyclohexylcarbodiimide in 40 ml of methylene chloride. The addition of the reagents is carried out at room temperature and while stirring. The reaction mixture is stirred for 20 hours at room temperature, freed from dicyclohexylurea by means of filtration and the filtrate is evaporated under reduced pressure. The residue is taken up in ethyl acetate and mixed with an aqueous dipotassium hydrogen phosphate buffer solution (pH 7.5). The aqueous portion is separated, washed several times with ethyl acetate and the pH adjusted to 2.5 with 20% aqueous phosphoric acid. After repeated extraction with ethyl acetate, the organic extracts from the aqueous phase having pH 2.5 are combined, washed with water and a saturated aqueous sodium chloride solution, dried over magnesium sulphate and evaporated under reduced pressure. The residue is chromatographed on 450 g of silica gel, elution being carried out with methylene chloride containing 5% of methyl acetate, fractions of 500 ml being taken. The residue of the fractions 12–13 is crystallised from ethyl acetate and yields the 3-(4-methoxy-1-naphthylmethyl)-7β-phenylacetylamino-ceph-2-em-4ξ-carboxylic acid 2,2,2-trichloroethylester, which melts at 145–147°; $[\alpha]_D^{20} = + 271° \pm 1°$ (c = 0,918 in chloroform); ultraviolet absorption spectrum (in methanol): $\lambda_{max}$ = 210 mµ ($\epsilon$ = 67000), 232 mµ ($\epsilon$ = 41200), 298 mµ ($\epsilon$ = 9990) and 322 mµ ($\epsilon$ = 4960); infrared absorption spectrum (in mineral oil): characteristic bands at 2,90µ, 5,62µ, 5,68µ, 6,02µ, 6,27µ and 6,60µ; thin-layer chromatogram (silica gel): Rf = 0.27 (system: toluene/ethyl acetate 4:1) and Rf = 0.38 (system: toluene/acetone 9:1).

Fraction 14 of the chromatogram yields the desired ester together with a by-product and fractions 15–17 yield an impure by-product which is crystallised from ethyl acetate. The mother liquor of crystallisation and fractions 14 are combined, evaporated to dryness and the residue is chromatographed on 60 g of silica gel, extraction being performed with methylene chloride containing 3% of methyl acetate; and fractions of 100 ml being taken. Fractions 4 and 5 contain a further amount of the 3-(4-methoxy-1-naphthylmethyl)-7β-phenylacetyl-amino-ceph-2-em-4ξ-carboxylic acid 2,2,2-trichloroethyl ester.

EXAMPLE 40

A solution of 6.3 g of 3-(4-hydroxy-3-methoxybenzyl)-7β-phenylacetylamino-ceph-2-em-4ξ-carboxylic acid in 20 ml of methanol is diluted with 70 ml of ethyl acetate, then treated with 3.9 g. of diphenyldiazomethane. The reaction mixture is stirred for 1 hour at room temperature and then evaporated under reduced pressure. The residue is crystallised from ethyl acetate; the mother liquor is evaporated to dryness and the residue crystallised from cyclohexane. The two crystalline products are combined and recrystallised from a mixture of ethyl acetate and cyclohexane. The resulting 3-(4-hydroxy-3-methoxy-benzyl)-7β-phenylacetyl-amino-ceph-2-em-4ξ-carboxylic acid diphenylmethyl ester melts at 165°–166°C; $[\alpha]_D^{20} = + 343° \pm 1°$ (c = 0.947 in 95% ethanol); thin-layer chromatogram (silica gel): Rf = 0.48 (system toluene/ethyl acetate 1:1) and Rf = 0.36 (system toluene/acetone 4:1); ultraviolet absorption spectrum (in 95% ethanol): $\lambda_{max}$ = 255 mµ ($\epsilon$ = 3930) and 282 mµ ($\epsilon$ = 1860); infrared absorption spectrum (in mineral oil): characteristic bands at 2,80µ, 2,98µ, 5.62µ, 5.77µ, 6,02µ and 6.59µ.

EXAMPLE 41

A solution of 7β-phenylacetylamino-3-(2-thenyl)-ceph-2-em-4ξ-carboxylic acid in 150 ml of methanol is diluted with 200 ml of ethyl acetate, then treated with 9.70 g of diphenyldiazomethane in 20 ml of ethyl acetate. The reaction mixture is stirred at room temperature for 1 hour and evaporated to dryness under reduced pressure. The residue is crystallised from ethyl acetate and chromatographed on 400 g of silica gel. Elution with ethyl acetate yields the 7β-phenylacetylamino-3-(2-thenyl)-ceph-2-em-4ξ-carboxylic acid diphenylmethylester, which after recrystallisation from ethyl acetate melts at 166°–167°; $[\alpha]_D^{20} = + 359° \pm 2°$ (c = 0.490 in 95% ethanol); thin-layer chromatogram (silica gel): Rf = 0.73 (system: toluene/ethyl acetate 1:1) and Rf = 0.56 (system: toluene/acetone 4:1); ultraviolet absorption spectrum (in 95% alkanol): strong terminal absorption; infrared absorption spectrum (in mineral oil); characteristic bands at 2,97µ, 5,62µ, 5,75µ, 6,03µ and 6,54µ.

EXAMPLE 42

A solution of 0.337 g of amorphous 3-(2,2-diacetylethyl)-7β-phenylacetyl-amino-ceph-2-em-4ξ-carboxylic acid in 5 ml of methanol and 50 ml of ethyl acetate is treated with an excess of diphenyldiazomethane and the solvent is removed under reduced pressure after a 30 minute reaction period. The residue is triturated with petroleum ether, the insoluble material filtered off and chromatographed on 20 g of silica gel (column). The 3-(2,2-diacetylethyl)-7β-phenylacetyl-amino-ceph-2-em-4ξ-carboxylic acid diphenylmethyl ester is eluted with a 9:1-mixture of methylene chloride and ethyl acetate in a colourless, amorphous form; ultraviolet absorption spectrum (in methanol): $\lambda_{max}$ = 286 mµ ($\epsilon$ = 6240) and 255 mµ ($\epsilon$ = 7450); infrared absorption spectrum (in methylene chloride): characteristic bands at: 2,69µ, 2,90µ, 5,60µ, 5,72µ, 5,92µ, 6,22µ, 6,65µ, 6,88µ, 7,19µ, 7,57µ, 8,17µ, 8,46µ, 8,65µ, 9,27µ, 9,72µ, 10,23µ and 10,54µ.

EXAMPLE 43

A suspension of 0.456 g of 3-(5-methoxycarbonylfurfuryl)-7β-phenylacetyl-amino-ceph-2-em-4ξ-carboxylic acid in 5 ml of water is treated in a vessel equipped with a stirrer and an automatic triturating apparatus (adjusted to pH 9.5; contains 0.1N aqueous sodium hydroxide solution to regulate the pH value) with 10 ml of the sodium hydroxide solution (1 equivalent) at room temperature, whereupon a complete solution is obtained. The temperature is raised to 30°–34°. The addition of the sodium hydroxide solution decreases after 3½ hours; a further 8 ml are added during this period. The solution is then cooled, diluted with water and washed with ethyl acetate. The pH value of the aqueous layer is adjusted to 2.5 by the addition of 20% aqueous phosphoric acid. After extraction with ethyl acetate, the resulting extracts are washed with water and a saturated aqueous sodium chloride solution, dried over sodium sulphate and evaporated under reduced pressure. The reaction is repeated and the last two residues are combined. The resulting crude product contains in addition to unreacted starting material the 3-(5-carboxy-furfuryl)-7β-phenylacetyl-amino-ceph-2-em-4ξ-carboxylic acid and is further processed without purification.

The above crude product is dissolved in 5 ml of methanol, the solution diluted with 30 ml of ethyl acetate and treated with a solution of 1.2 g of diphenyldiazomethane in 50 ml of ethyl acetate. The mixture is stirred for 2 hours at room temperature and the solvent is removed under reduced pressure. The residue is crystallised from methanol to yield a crystalline product (A); a further product (B) is isolated from the crystallization mother liquor. Product (A) consists of a new product contaminated by tetraphenylketazine, whereas product (B) contains tetraphenylketazine, the new product and 3-(5-methoxycarbonyl-furfuryl)-7β-phenylacetyl-amino-ceph-2-em-4ξ-carboxylic acid diphenylmethyl ester; both products are chromatographed individually. Product (A) is chromatographed on 30 g of silica gel, elution being carried out with methylene chloride, then with a 1:1-mixture of methyl acetate and methylene chloride and 100 ml fractions being taken. The tetraphenylketazine is removed with 5 fractions of methylene chloride and the first fraction with the solvent mixture contains the pure 3-(5-diphenylmethoxycarbonyl-furfuryl)-7β-phenylacetylamino-ceph-2-em-4ξ-carboxylic acid diphenylmethyl ester, which after repeated recrystallisation from ethyl acetate melts at 155°–156°; $[\alpha]_D^{20} = +217° \pm 1°$ (c = 0.844 in chloroform); thin-layer chromatogram (silica gel): Rf = 0.73 (system: toluene/ethyl acetate 1:1) and Rf = 0.59 (system: toluene/acetone 4:1); ultraviolet absorption spectrum (in methanol): $\lambda_{max} = 262$ mμ (ε = 23200) and $\lambda_{min} = 236$ mμ (ε = 12200); infrared absorption spectrum (in mineral oil): characteristic bands at 2,98μ, 5,77μ, 5,80μ, 6,04μ and 6,52μ.

Product (B) from the mother liquor is chromatographed on 30 g of silica gel. The tetraphenylketazine is washed out with 400 ml methylene chloride and the 3-(5-diphenylmethoxycarbonyl-furfuryl)-7β-phenylacetyl-amino-ceph-2-em-4ξ-carboxylic acid diphenylmethyl ester is eluted with a further 400 ml of methylene chloride. The 3-(5-methoxycarbonyl-furfuryl)-7β-phenylacetyl-amino-ceph-2-em-4ξ-carboxylic acid diphenylmethyl ester is eluted with methylene chloride containing 10% of methyl acetate.

EXAMPLE 44:

A mixture of 0.550 g of 3-(5-diphenylmethoxycarbonyl-furfuryl)-7β-phenylacetyl-amino-ceph-2-em-4ξ-carboxylic acid diphenylmethyl ester and 0.380g of anisol is treated with 10 ml of trifluoroacetic acid and left to stand for 10 minutes at room temperature. The mixture is diluted with an equal volume of toluene and evaporated under reduced pressure. The residue is partitioned between ethyl acetate and a 10% aqueous dipotassium hydrogen phosphate solution (pH 7.8). The layers are separated, the aqueous phase is washed several times with ethyl acetate and the pH adjusted to 2.5 by addition of 20% aqueous phosphoric acid. After extraction with ethyl acetate, the resulting organic extracts are washed with water and a saturated aqueous sodium chloride solution, dried over sodium sulphate and evaporated under reduced pressure. The residue is recrystallised from ethyl acetate and yields the 3-(5-carboxy-furfuryl)-7β-phenylacetyl-amino-ceph-2-em-4ξ-carboxylic acid, which melts at 194°–195°; $[\alpha]\Sigma D20 + 315° \pm 1°$ (c = 1.010 in dioxan); thin-layer chromatogram (silica gel): Rf = 0.65 (system n-butanol/acetic acid/water 67:10:23) and Rf = 0.38 (system n-butanol/ethanol/water 40:10:50); infrared absorption spectrum (in mineral oil): characteristic bands at 2,99μ, 5,67μ, 5,76μ, 5,90μ, 6,04μ, 6,26μ, 6,51μ and 6,53μ (shoulder).

EXAMPLE 45:

A solution of 6.50 g of 3-(4-hydroxy-benzyl)-7β-phenylacetyl-amino)-ceph-2-em-4ξ-carboxylic acid in 15 ml of methanol is diluted with 200 ml of ethyl acetate and treated at room temperature in small amounts with a total of 5.82 g of crude diphenyldiazomethane. The reaction solution, which at first generates large amounts of nitrogen, is left to stand for 1 hour at room temperature, and retains its purplish red colouration. The solvent is then distilled off under reduced pressure. The residue is digested with a 1:1-mixture of diethyl ether and petroleum ether; the undissolved material is filtered off and washed repeatedly with the diethyl ether-petroleum ether mixture on the suction filter. The faintly yellow crude product is dissolved in methylene chloride and chromatographed on 400 g of silica gel. Non-polar impurities are washed out with methylene chloride, containing 5–7% of methyl acetate (4 fractions of 500 ml each). The colourless 3-(4-hydroxy-benzyl)17β-phenylacetyl-amino-ceph-2-em-4ξ-carboxylic acid diphenylmethyl ester, which is pure according to chromatography, is eluted with 4 fractions of 500 ml each of a 9:1-mixture of methylene chloride and methyl acetate. The residue is crystallised from a mixture of methylene chloride, diethyl ether and cyclohexane; after repeated crystallisation from the solvent mixture and after drying for 15 hours under a high vacuum at 35°, it melts in the form of fine, colourless needles at 133°–134°; $[\alpha]\Sigma D20 + 334° \pm 1°$ (c = 1.070 in chloroform); thin-layer chromatogram (silica gel): Rf = 0.44 (system: toluene/acetone 4:1), Rf = 0.59 (system: toluene/acetone 2:1) and Rf = 0.72 (system: toluene/ethyl acetate 1:1); ultraviolet absorption spectrum (in 95% ethanol): $\lambda_{max} = 253$ mμ (ε = 7650), $\lambda_{min} = 249$ mμ (ε = 7600) and shoulder at 280 mμ (ε = 2400); infrared absorption spectrum (in methylene chloride): characteristic bands at 2,76μ, 2,89μ, 5,60μ, 5,72μ, 5,93μ, 6,19μ, 6,25μ, 6,61μ, 6,67μ (shoulder), 7,50μ, 7,55μ, 8,17μ, 8,45μ, 8,54μ, 8,63μ, 10,20μ and 12,13μ.

EXAMPLE 46:

A solution of 6.85 g of crystallised 3-(5-methoxycarbonyl-furfuryl)-7β-phenylacetyl-amino-ceph-2-em-4ξ-carboxylic acid in 50 ml of methanol is treated with 100 ml of ethyl acetate and the methanol is almost completely removed under reduced pressure. A total of 6.0 g of crude diphenyldiazomethane is then added in small amounts. The reaction mixture is freed from solvent after a total reaction period of 60 minutes at room temperature. The residual oil is triturated with 500 ml of petroleum ether, the undissolved material is filtered off and crystallised from 100 ml of hot ethyl acetate. The first crystalline fraction is recrystallised twice from a mixture of methylene chloride and cyclohexane to yield the 3-(5-methoxycarbonyl-furfuryl)-7β-phenylacetyl-amino-ceph-2-em-4ξ-carboxylic acid diphenylmethyl ester in the form of colourless felted needles, m.p. 164°-166°; $[\alpha]\Sigma D20 + 267° \pm 1°$ (c = 1.134 in chloroform): thin-layer chromatogram (silica gel): Rf = 0.71 (system: toluene/ethyl acetate 1:1), Rf = 0.60 (system: toluene/ethyl acetate 2:1), Rf = 0.70 (system: toluene/acetone 2:1), Rf = 0.49 (system: toluene/acetone 4:1) and Rf = 0.30 (system toluene/acetone 9:1); ultraviolet absorption spectrum (in 95% ethanol): $\lambda_{max} = 268$ mμ ($\epsilon = 21000$) and $\lambda_{min} = 234$ mμ ($\epsilon = 11000$); infrared absorption spectrum (in mineral oil): characteristic bands at 2,98μ, 5,61μ, 5,74μ, 6,03μ, 6,53μ, 7,59μ, 8,26μ, 8,54μ, 8,72μ, 9,81μ, 10,14μ, 13,13μ and 14,42μ.

The second crystalline fraction, which results upon addition of cyclohexane, is chromatographed together with the mother liquor of the first fraction on 120 g of silica gel. The above ester compound is eluted with methylene chloride containing 3–5% of methyl acetate, and crystallised from a mixture of methylene chloride and cyclohexane. The crude 3-hydroxymethyl-7β-phenylacetyl-amino-ceph-2-em-4ξ-carboxylic acid diphenylmethyl ester is eluted with methylene chloride, containing 10-20% methyl acetate.

EXAMPLE 47:

A solution of 0.81 g of 3-(2-oxo-cyclohexyl)-methyl-7β-phenylacetyl-amino-ceph-2-em-4ξ-carboxylic acid in 5 ml of methanol and 50 ml of ethyl acetate, is treated with 0.58 g of diphenyldiazomethane in 20 ml of ethyl acetate. The mixture is stirred for 45 minutes at room temperature and evaporated to dryness. The residue is digested with petroleum ether to remove excess diphenyldiazomethane. The resulting insoluble, viscous oil is chromatographed on 30 g of silica gel. The 3-(2-oxocyclohexyl)-methyl-7β-phenylacetyl-amino-ceph-2-em-4ξ-carboxylic acid diphenylmethyl ester is eluted with 19:1- and 9:1-mixtures of methylene chloride and methyl acetate. The colourless amorphous product is almost a uniform substance according to thin-layer chromatgraphy (silica gel): Rf = 0.41 (system: toluene/acetone 4:1) and Rf = 0.63 (system: toluene/ethyl acetate 1:1); ultraviolet absorption (in methanol): $\lambda_{max} = 251$ mμ ($\epsilon = 6000$), $\lambda_{min} = 242$ mμ ($\epsilon = 5750$) and $\lambda_{shoulder} = 286$ mμ ($\epsilon = 2800$); infrared absorption spectrum (in methylene chloride): characteristic bands at 2,91μ, 5,62μ, 5,73μ, 5,92μ, 5,95μ, 6,63μ, 6,67μ, 6,88μ, 7,26μ, 7,58μ, 8,16μ, 8,43μ, 8,60μ, 9,06μ, 9,73μ and 10,23μ.

EXAMPLE 48:

If in the process of Example 37 the 3-[5-(2-bromoethoxycarbonyl)-methyl-furfuryl]-7β-[N-2-bromoethoxycarbonyl-D-(α)-phenylglycyl]-amino-ceph-2-em-4ξ-carboxylic acid is used instead of the 3-(2,5-dimethoxy-benzyl)-7β-phenylacetylamino-ceph-2-em-4ξ-carboxylic acid and is esterified in the dioxane-methanol mixture with diphenyldiazomethane, the 3-[5-(2-bromoethoxycarbonyl)-methyl-furfuryl-7β-[N-2-bromoethoxycarbonyl-D-(α)-phenylglycyl]-amino-ceph-2-em-4ξ-carboxylic acid diphenylmethyl ester is obtained, which is recrystallised from a mixture of methyl acetate and isopropanol, m.p. 72°-73°; thin-layer chromatogram (silica gel): Rf = 0.75 (system: methylene chloride/acetone 10:1), Rf = 0.26 (system: toluene/ethyl acetate 2:1), and Rf = 0.96 (system: chloroform/ethanol 10:1); ultraviolet absorption spectrum (in ethanol: $\lambda_{max} = 216$ mμ ($\epsilon = 26350$) and $\lambda_{shoulder} = 252$ mμ ($\epsilon = 7150$); infrared absorption spectrum (in methylene chloride): characteristic bands at: 2,87 μ, 3,40μ, 5,53μ, 5,66μ, 5,71μ, 6,61μ, 7,50μ, 8,16μ, 8,55μ, 9,72μ and 10,17μ.

EXAMPLE 49:

If in the process of Example 37 the 7β-[N-2-bromoethoxycarbonyl-D-(α)-phenylglycyl]-amino-3-(4-hydroxy-benzyl)-ceph-2-em-4ξ-carboxylic acid is used instead of the 3-(2,5-dimethoxy-benzyl)-7β-phenylacetylamino-ceph-2-em-4ξ-carboxylic acid and is esterified in a 9:1-mixture of dioxane and methanol with diphenyldiazomethane, the 7β-[N-2-bromoethoxycarbonyl-D-(α)-phenylglycyl]-amino-3-(4-hydroxybenzyl)-ceph-2-em-4ξ-carboxylic acid diphenylmethyl ester is obtained, which after recrystallization from a mixture of methyl acetate and isopropanol melts at 99°-100°; thin-layer chromatogram (silica gel): Rf = 0.55 (system: chloroform/methanol 97:3) and Rf = 0.25 (system: chloroform/acetone 9:1); ultraviolet absorption spectrum (in ethanol): $\lambda_{max} = 214$ mμ ($\epsilon = 20100$) and $\lambda_{shoulder} = 254$ mμ ($\epsilon = 4740$); infrared absorption spectrum (in methylene chloride); 2,86μ, 2,91μ, 3,27μ, 3,34μ, 5,60μ, 5,74μ, 5,88μ, 6,18μ, 6,60μ, 6,67μ, 6,87μ, 7,18μ, 7,51μ, 8,18μ, 8,45μ, 8,53μ, 9,25μ, 9,61μ, 10,31μ, 10,57 μ and 12,17μ.

EXAMPLE 50:

A solution of 6.7 g of crude crystalline 3-(5-methoxycarbonyl-furfuryl)-7β-[N-2-bromoethoxycarbonyl-D-(α)-phenylglycyl]-amino-ceph-2-em-4ξ-carboxylic acid in 100 ml of a 4:1-mixture of dioxane and methanol is left to stand for 3 hours with an excess of solid diphenyldiazomethane. Upon addition of a few drops of acetic acid, the reaction solution is evaporated to dryness under reduced pressure. The faintly yellow residual foam is dissolved in a small amount of methylene chloride and subjected to a rapid chromatogram on 300 g of silica gel (column). The 3-(5-methoxycarbonyl-furfuryl)-7β-[N-2-bromoethoxycarbonyl-D-(α)-phenylglycyl]-amino-ceph-2-em-4ξ-carboxylic acid diphenylmethyl ester, which is pure according to thin-layer chromatography, is eluted with a 9:1-mixture of methylene chloride and methyl acetate and crystallised from a mixture of methylene chloride, diethyl ether and cyclohexane. For purpose of analysis, a sample is again crystallised from the same solvent; the resulting crystals sinter in the range of 129°-138° and then melt sharply at 163° (uncorr.); [ $\alpha]_D^{20} = + 192° \pm 1°$ (c = 0.985 in chloroform): thin-layer chromatogram (silica gel, plates; detection with UV light λ = 254 mμ and iodine vapour): Rf = 0.44 (system: toluene/acetone 4:1), Rf = 0.19 (system: toluene/acetone 9:1), Rf = 0.24 (system: toluene/ethyl acetate 4:1) and Rf = 0.68 - 0.70 (system: toluene/ethyl acetate 1:1); ultraviolet absorption spectrum (in 95% aqueous ethanol): $\lambda_{max} = 260$ mμ ($\epsilon = 20200$) and $\lambda_{min} = 236$ mμ ($\epsilon = 11200$); infrared absorption spectrum (in mineral oil): characteristic bands at: 3,00μ, 3,24μ, 5,62μ, 5,75μ, 5,89μ, 6,01μ, 6,48μ, 7,37μ, 7,63μ, 7,84μ, 8,26μ, 8,55μ, 8,74μ, 9,83μ, 13,19μ and 14,14μ.

EXAMPLE 51:

A solution of 0.975 g of 7β-formylamino-3-(2-thenyl)-ceph-2-em-4ξ-carboxylic acid in 10 ml of dioxane is treated with 1.2 ml of a 1:1-mixture of concentrated hydrochloric acid and water and left to stand for 3 days at room temperature. The faintly yellow reaction solution is lyophilised to yield the 7β-amino-3-(2-thenyl)-ceph-2-em-4ξ-carboxylic acid hydrochloride, which according to thin-layer chromatogram which contains only traces of the starting material; thin-layer chromatogram (silica gel; detection with iodine vapour); Rf = 0.40 (system: n-butanol/acetic acid/water 67:10:23; starting material Rf = 0.56), Rf = 0.51 (system: n-butanol/pyridine/acetic acid/water 40:24:6:30; starting material Rf = 0.60), and Rf = 0.43 (system: ethyl acetate/n-butanol/pyridine/acetic acid/water 42:21:21:6:10; starting material Rf = 0.64).

EXAMPLE 52:

A suspension of 0.666 g of lyophilised 7β-amino-3-(2-thenyl)-ceph-2-em-4ξ-carboxylic acid hydrochloride in 20 ml of absolute methylene chloride is treated with 0.56 ml of triethylamaine. The mixture is cooled to −10° and a solution of 0.34 g of phenylacetic chloride in 5 ml of absolute methylene chloride is added dropwise while stirring with a magnetic stirrer. Stirring is continued for 1 hour at −10° and for 1 hour at room temperature. The reaction solution is diluted with 20 ml of methylene chloride and extracted several portions of a 0.5 molar aqueous dipotassium hydrogen phosphate solution. The aqueous extracts are covered with ethyl acetate and acidified to pH 2 with 20% phosphoric acid. The phases are separated, the aqueous phase is reextracted with ethyl acetate and discarded. The organic extracts are washed with a saturated aqueous sodium chloride solution, dried over magnesium sulphate and freed from solvent under reduced pressure. The residue is purified by means of a rapid chromatogram on 20 g of silica gel, washed with concentrated hydrochloric acid. The 7β-phenylacetylamino-3-(2-thenyl)-ceph-2-em-4ξ-carboxylic acid is eluted with a 3:1-mixture of methylene chloride and methyl acetate and recrystallised from a mixture of acetone and 1,1,1-trichloroethane; after drying under high vacuum at 35°, the colourless crystals melt at 191.5°–192.5° (with decomp.).

EXAMPLE 53:

A solution of 0.333 g of 3-(4-methoxy-benzyl)-7-(N-phenylacetyl-amino)-ceph-2-em-4ξ-carboxylic acid diphenylmethyl ester in 4 ml of a 10% strength solution of triethylamine in absolute pyridine is left to stand under a nitrogen atmosphere for 3½ days at room temperature with exclusion of light and is then evaporated to dryness under reduced pressure. The residue is mixed with toluene and the mixture is evaporated to dryness; this operation is repeated twice more. The crude product is chromatographed on a 100-fold amount of silica gel.

The desired 3-(4-methoxy-benzyl)-7-(N-phenylacetyl-amino)-ceph-3-em-4-carboxylic acid diphenylmethyl ester is eluted with a 7:3 mixture of toluene and methylene chloride; after two recrystallisations from a mixture of methylene chloride, 1,1,1-trichlorethane and cyclohexane, the ester melts at 198.5°–199.5°C (uncorrected); $[\alpha]_D^{20} = -86° \pm 1°$ (c = 0.870 in chloroform); thin layer chromatogram (silica gel G; development with iodine vapour): Rf = 0.61 (system toluene/acetone, 4:1), Rf = 0.22 (system toulene/acetone, 19:1), Rf = 0.58 (system toluene/diethyl ether, 1:1) and Rf = 0.87 (system toluene/acetic acid ethyl ester, 1:1); ultraviolet absorption spectrum (in 95% strength ethanol, non-denatured): $\lambda_{max} = 259$ mμ ($\epsilon = 10700$) and $\lambda_{min} = 247$ mμ ($\epsilon = 10100$); infrared absorption spectrum (in methylene chloride): characteristic bands at 2.90μ, 3.51μ, 5.58μ, 5.77μ, 5.92μ, 6.19μ, 6.31μ, 6.61μ, 6.66μ (shoulder), 7.27μ, 8.48μ, 8.61μ, 9.02μ, 9.69μ and 9.87μ. On further elution with the 7:3 mixture of toluene and methylene chloride, mixed fractions with increasing content of 3-(4-methoxy-benzyl-7-(N-phenylacetyl-amino)-ceph-2-em-4ξ-carboxylic acid diphenylmethyl ester are obtained. A further quantity of the desired ceph-3-em compound can be obtained from these fractions by crystallisation from a mixture of methylene chloride, 1,1,1-trichlorethane and cyclohexane. Finally, small quantities of the ceph-2-em compound are eluted with pure methylene chloride, and this compound together with the mother liquor from the above crystallisation can again be subjected to the isomerisation.

EXAMPLE 54:

A solution of 0.667 g of 3-(2,5-dimethoxy-benzyl)-7-(N-phenylacetyl-amino)-ceph-2-em-4ξ-carboxylic acid diphenylmethyl ester in 8 ml of absolute pyridine is mixed with 0.8 ml of absolute triethylamine. The yellowish solution is left to stand for 3 days in the dark under a nitrogen atmosphere and at room temperature and is then evaporated to dryness under reduced pressure. The residue is repeatedly mixed with absolute toluene and in each case the mixture is evaporated to dryness. The crude product is chromatographed on a column of 60 g of silica gel (with 5% of water). 3-(2,5-Dimethoxy-benzyl)-7-(N-phenylacetyl-amino)-ceph-3-em-4-carboxylic acid diphenylmethyl ester is eluted with a 3:7-mixture of toluene and methylene chloride; after recrystallisation from a mixture of methylene chloride and cyclohexane, the ester melts at 158° – 158.5°C (uncorrected); it is dried for 20 hours in a high vacuum at 35°C; $[\alpha]_D^{20} = -8° \pm 1°$ (c = 0.972 in chloroform); thin layer chromatography (silica gel; development with iodine vapour): Rf = 0.60 (system toluene/-diethyl ether, 1:1), Rf = 0.86 (system toluene/acetic acid ethyl ester, 1:1) and Rf = 0.32 (system toluene-/acetone, 4:1); ultraviolet absorption spectrum (in 95% strength ethanol; non-denatured): $\lambda_{max} = 263$ mμ ($\epsilon = 10850$) and $\lambda_{min} = 242$ mμ ($\epsilon = 8150$); infrared absorption spectrum: characteristic bands in methylene chloride at 2.92μ, 3,52μ, 5.61μ, 5.79μ, 5.93μ, 6.67μ, 7.29μ, 8.21μ, 8.51μ, 8.62μ, 9.56μ and 9.88μ, and in mineral oil at 2.98μ, 5.66μ, 5.77μ, 6.03μ, 6.51μ, 6.66μ, 7.47μ, 7.90μ, 8.05μ, 8.54μ, 8.96μ, 9.47μ, 14.20μ and 14.43μ.

Using pure methylene chloride, a mixture of 3-(2,5-dimethoxy-benzyl)-7-(N-phenylacetyl-amino)-ceph-3-em-4-carboxylic acid dephenylmethyl ester and the starting material is eluted, and this together with the crystallisation mother liquor can be subjected to a new equilibration experiment.

EXAMPLE 55:

A solution of 10.2 g of 7β-phenylacetyl-amino-3-(2-thenyl)-ceph-2-em-4ξ-carboxylic acid diphenylmethyl ester in 130 ml of a 9:1-mixture of pyridine and triethylamine is left to stand in the dark and under nitrogen for 3½ days at room temperature, then evaporated under reduced pressure. The residue is evaporated several times to dryness with toluene and then triturated with ethyl acetate. The solid residue is recrystallised from ethyl acetate and yields the somewhat impure 7β-phenylacetyl-amino-3-(2-thenyl)-ceph-3-em-4-carboxylic acid diphenylmethyl ester. The mother liquors of trituration and crystallisation are evaporated to dryness and yield on evaporation a mixture of the 7β-phenylacetylamino-3-(2-thenyl)-ceph-2-em-4ξ-carboxylic acid diphenylmethyl ester and the 7β-phenylacetyl-amino-3-(2-thenyl)-ceph-3-em-4-carboxylic acid diphenylmethyl ester which is chromatographed on 160 g of silica gel. Elution is performed with methylene chloride containing 2% of ethyl acetate, fractions of 200 ml (of 100 ml from fraction 9) being taken. Fractions 5-8 yield some impure 7β-phenylacetyl-amino-3-(2-thenyl)-ceph-3-em-4-carboxylic acid diphenylmethyl ester and fractions 9-11 some impure 7β-phenylacetyl-amino-3-(2-thenyl)ceph-2-em-4ξ-carboxylic acid diphenylmethyl ester. The product of fractions 5-8 is crystallised from ethyl acetate and combined with the first crystalline product and chromatographed on 60 g of silica gel. Elution is performed with methylene chloride containing 0.5% of ethyl acetate, fractions of 60 ml being taken. Fractions 7-9 yields the pure 7β-phenylacetyl-amino-3-(2-thenyl)-ceph-3-em-4-carboxylic acid diphenylmethyl ester, which after crystallisation from ethyl acetate melts at 184°C; $[\alpha]_D^{20} = -65° \pm 1°$ (c = 0.968 in chloroform): thin-layer chromatogram (silica gel): Rf = 0.46 (system: toluene/ethyl acetate 4:1) and Rf = 0.57 (system: toluene/acetone 9:1); ultraviolet absorption spectrum (in 95% ethanol): $\lambda_{max} = 264μ$ ($\epsilon = 9600$); infrared spectrum (in mineral oil); characteristic bands at 2,99μ, 5,59μ, 5,77μ, 5,98μ, 6,10μ and 6,50μ.

EXAMPLE 56:

A solution of 4.10 g of 3-furfuryl-7β-phenylacetyl-amino-ceph-2-em-4ξ-carboxylic acid diphenylmethyl ester in 25 ml of absolute pyridine and 5 ml of absolute triethylamine is left to stand for 3½ days under nitrogen at room temperature. The reaction solution is then evaporated to dryness several times while adding toluene. The residue is chromatographed on 200 g of silica gel (column.), fractions of 250 ml eah being taken. a product is eluted in fraction 8 with methylene chloride containing 2% ethyl acetate. This product consists mainly of the desired 3-furfuryl-7β-phenylacetyl-amino-ceph-3-em-4-carboxylic acid diphenylmethyl ester and after two crystallisations from a mixture of methylene chloride, diethyl ether and cyclohexane, yields the pure product in the form of colourless felted needles, m.p. 186.5° – 187° (uncorr.); $[\alpha]_D^{20} = -23° \pm 1°$ (c = 0.974 in chloroform): thin-layer chromatogram (silica gel; development with iodine vapour): Rf = 0.83 (system: toluene/ethyl acetate 1:1), Rf = 0.75 (system: toluene/ethyl acetate 2:1), Rf = 0.68 (system: toluene-/acetone 4:1) and Rf = 0.51 (system: toluene/acetone 9:1) (the Rf values for the corresponding ceph2-em compound are 0.80, 0.73, 0.66 and 0.48, respectively); ultraviolet absorption spectrum (95% ethanol: $\lambda_{max} = 264$ mμ ($\epsilon = 8150$) and $\lambda_{min} = 240$ mμ ($\epsilon = 5950$); infrared absorption spectrum: characteristic bands at 3,01μ, 5,60μ, 5,78μ, 6,01μ, 6,09μ, 6,51μ, 6,66μ, 8,14μ, 8,56μ, 9,08μ and 9,81μ (in mineral oil and 2,89μ, 5,58μ, 5,77μ, 5,92μ, 6,65μ, 8.17μ, 8,62μ, 9,14μ and 9,87μ.

Fraction 9 of the above chromatogram contains a mixture consisting of 3-furfuryl-7β-phenylacetyl-amino-ceph-3-em-4-carboxylic acid diphenylmethyl ester, an unidentifiable product and some starting material, from which a further amount of the 3-furfuryl-7β-phenylacetyl-amino-ceph-3-em-4-carboxylic acid diphenylmethyl ester can be obtained by repeated crystallisation.

EXAMPLE 57:

A solution of 6.1 g of 3-(4-hydroxy-3-methoxybenzyl)-7-phenylacetyl-amino-ceph-2-em-4ξ-carboxylic acid diphenylmethyl ester in 63.5 ml of absolute pyridine and 6.5 ml of triethylamine is left to stand for 3½ days under nitrogen at room temperature, then evaporated to dryness several times while adding toluene. The residue is separated by chromatography on 330 g of silica gel; elution is carried out with methylene chloride containing 3% methyl acetate, fractions of 250 ml each being taken. The 3-(4-hydroxy-3-methoxy-benzyl)-7β-phenylacetyl-amino-ceph-3-em-4-carboxylic acid diphenylmethyl ester is isolated in fractions 6-8, whereas fractions 9 and 10 contain a mixture of the product and the starting material. The succeeding fractions 11-16 contain principally unchaged starting material. The material from fractions 9 and 10 and the mother liquors of the crystallised products (from a mixture of methylene chloride, diethyl ether and cyclohexane) of fractions 6-8 are chromatographed once more on 130 g of silica gel. Elution is effected with methylene chloride containing 1% of ethyl acetate, fractions of 100 ml each being taken. 3-(4-Hydroxy-3-methoxy-benzyl)-7β-phenylacetyl-amino-ceph-3-em-4-carboxylic acid diphenylmethyl ester, which is almost pure according to chromatography, is eluted in fractions 6-18. These fractions are crystallised from a mixture of methylene chloride, diethyl ether and cyclohexane; the 3-(4-hydroxy-3-methoxybenzyl)-7β-phenylacetyl-amino-ceph-3-em-4-carboxylic acid diphenylmethyl ester melts at 166°–167° (the analytical sample is dried for 15 hours under a high vacuum at 35° and still contains cyclohexane according to the nuclear reasonance spectrum). The solvent can be completely removed after final drying for 20 hours at 45°; m.p. 166°–167.5°C (uncorr.) $[\alpha]_D^{20} = -92° \pm 1°$ (c = 0.968 in chloroform): thin-layer chromatogram (silica gel):

Rf = 0.70 (system: toluene/ethyl acetate 1:1), Rf = 0.50 (system: toluene/ethyl acetate 2:1), Rf = 0.44 (system: toluene/acetone 4:1) and Rf = 0.21 (system: toluene/acetone 9:1) (the Rf values of the corresponding ceph-2-em compound are 0.68, 0.46, 0.40 and 0.15, respectively); ultraviolet absorption spectrum (in 95% ethanol): $\lambda_{max}$ = 272 m$\mu$ ($\epsilon$ = 9150) and $\lambda_{min}$ = 244 m$\mu$ ($\epsilon$ = 7300); infrared absorption spectrum: characteristic bands at: 2,78$\mu$, 3,02$\mu$, 5,60$\mu$, 5,83$\mu$, 6,02$\mu$, 6,54$\mu$, 6,60$\mu$, 7,90$\mu$, 8,08$\mu$, 8,56$\mu$, 8,90$\mu$, 9,12$\mu$ and 14,41$\mu$ (in mineral oil) and 2,80$\mu$, 2,90$\mu$, 5,60$\mu$, 5,78$\mu$, 6,21$\mu$, 6,61$\mu$, 7,27$\mu$, 8,12$\mu$, 8,28$\mu$, 8,50$\mu$ and 8,62$\mu$ (in methylene chloride).

EXAMPLE 58:

A solution of 2.0 g of 3-(4-hydroxy-benzyl)-7$\beta$-phenyl-acetyl-amino-ceph-2-em-4$\xi$-carboxylic acid diphenylmethyl ester in 21.6 ml of absolute pyridine and 2.4 ml of triethylamine is left to stand for 3½ days in the dark at room temperature. The faintly yellow solution is evaporated several times under reduced pressure while adding toluene. The residue is taken up in methylene chloride and chromatographed on 100 g of silica gel. After washing with methylene chloride, elution is carried out with methylene chloride, containing 5% of ethyl acetate, fractions of 100 ml of the solvent mixture being taken. Fractions 5–8 contain almost pure 3-(4-hydroxy-benzyl)-7$\beta$-phenyl-acetyl-amino-ceph-3-em-4-carboxylic acid diphenylmethyl ester, which after recrystallisation from a mixture of methylene chloride, diethyl ether and cyclohexane, melts in the form of fine, rather waxy crystals at 167°–168° (analytical sample: m.p. 169°–170° after repeated recrystallisations from methylene chloride, diethyl ether and cyclohexane and drying under a high vacuum at 35°); $[\alpha]_D^{20}$ = −84° ± 1° (c = 0.936 in chloroform): thin-layer chromatogram (silica gel): Rf = 0.50 (system: toluene/ethyl acetate 2:1), Rf = 0.69 (system: toluene/ethyl acetate 1:1), Rf = 0.20 (system: toluene/acetone 9:1) and Rf = 0.38 (system: toluene/acetone 4:1) (the corresponding ceph-2-em-compound has the following Rf values in these solvent systems: 0.43, 0.67, 0.15 and 0.38, respectively); ultraviolet absorption spectrum (in 95% ethanol): $\lambda_{max}$ = 267 m$\mu$ ($\epsilon$ = 9600) and $\lambda_{min}$ = 240 m$\mu$ ($\epsilon$ = 6700); infrared absorption spectrum (in mineral oil): characteristic bands at: 2,79$\mu$, 3,02$\mu$, 5,60$\mu$, 5,79$\mu$, 6,01$\mu$, 6,52$\mu$, 6,60$\mu$, 7,93$\mu$, 8,08$\mu$, 8,57$\mu$, 9,03$\mu$, 9,85$\mu$, 10,41$\mu$, 11,98$\mu$, 13,30$\mu$, 14,23$\mu$ and 14,46$\mu$.

Fractions 9 and 10 contain a mixture of the two isomeric compounds and are crystallised together with the mother liquors of fractions 5–8, in the process of which a further quantity of the pure ceph-3-em compound is obtained. Virtually pure starting material is obtained in the succeeding fractions and can be used again in further isomerisations.

EXAMPLE 59:

The mixture of 3-(2,5-dimethoxy-benzyl)-7-(N-phenylacetyl-amino)-ceph-2-em-4$\xi$-carboxylic acid diphenylmethyl ester and the corresponding ceph-3-em compound obtained according to the process described in example 54 by elution of the silica gel column with methylene chloride, and from the crystallisation mother liquor, is dissolved in 30 ml of absolute methylene chloride, then mixed with 0.364 g of purified 3-chloroperbenzoic acid whilst cooling in ice, and the whole left to stand for one hour at room temperature. The reaction mixture is treated with active charcoal and filtered, and the filtrate is evaporated to dryness. The residue is taken up in methylene chloride and the solution twice washed with 0.5 m aqueous dipotassium hydrogen phosphate solution; the aqueous wash solutions are re-extracted with methylene chloride. The organic extracts are twice washed with saturated aqueous sodium chloride solution, dried over magnesium sulphate and evaporated under reduced pressure. The crude product is dissolved in methylene chloride and mixed with cyclohexane, whilst warm, until the mixture begins to turn cloudy. After cooling, the finely crystalline material is filtered off and dried. After again crystallising from the same solvent mixture, the 3-(2,5-dimethoxybenzyl)-7-(N-phenylacetyl-amino)-ceph-3-em-4-carboxylic acid diphenylmethyl ester 1-oxide melts at 180° – 185°C (uncorrected; decomposition); $[\alpha]_D^{20}$ = + 63° ± 1° (c = 1.068 in chloroform); thin layer chromatography (silica gel G; development with iodine vapour): Rf = 0.44 (system toluene/acetone, 4:1), Rf = 0.48 (system toluene/acetic acid ethyl ester, 1:1), Rf = 0.09 (system toluene/acetic acid ethyl ester, 4:1) and Rf = 0.19 (system toluene/diethyl ester, 1:1); ultraviolet absorption spectrum (in 95% strength ethanol; non-denatured): $\lambda_{max}$ = 267 – 268 m$\mu$ ($\epsilon$ = 12600) and $\lambda_{min}$ = 244 m$\mu$ ($\epsilon$ = 7250); infrared absorption spectrum: characteristic bands in methylene chloride at 2.90$\mu$, 3.48$\mu$, 5.54$\mu$, 5.75$\mu$, 5.90$\mu$, 6.64$\mu$, 8.15$\mu$, 9.57$\mu$ and 9.88$\mu$ and in mineral oil at 2.97$\mu$, 5.61$\mu$, 5.77$\mu$, 5.99$\mu$, 6.49$\mu$, 6.65$\mu$, 7.72$\mu$, 8.12$\mu$, 8.45$\mu$, 8.52$\mu$, 9.40$\mu$, 9.47$\mu$, 9.66$\mu$ and 9.80$\mu$. A further quantity of the desired product can be obtained from the mother liquors by crystallisation.

EXAMPLE 60:

A solution of 4.5 g of a mixture of 3-(4-methoxybenzyl)-7-(N-phenylacetyl-amino)-ceph-2-em-4$\xi$-carboxylic acid diphenylmethyl ester and of the corresponding ceph-3-em compound, which can be obtained in the process of example 53 on purifying the crude product by chromatography, in 75 ml of methylene chloride is mixed with 1.34 g of purified 3-chloroperbenzoic acid and the mixture left to stand for one hour at room temperature. It is washed 3 times with 0.5 molar aqueous dipotassium hydrogen phosphate solution, and the aqueous solutions are extracted with methylene chloride. The organic solutions are washed with a saturated aqueous sodium chloride solution, dried over magnesium sulphate and evaporated under reduced pressure. The residue is chromatographed on a 30-fold quantity of silica gel. 3-(4-Methoxy-benzyl)-7-(N-phenylacetyl-amino)-ceph-3-em-4-carboxylic acid diphenylmethyl ester 1-oxide is eluted with a 9:1 mixture of methylene chloride and acetic acid methyl ester, crystallised from a mixture of methylene chloride and cyclohexane, recrystallised from a methylene chloride/diethyl ether mixture and an acetic acid methyl ester/diethyl ether mixture, and dried for 20 hours in a high vacuum at 35°C. The colourless felted crystals melt at 179° – 181°C (uncorrected; with decomposition); $[\alpha]_D^{20}$ = +71° ± 1° (c = 0.962 in chloroform); thin layer chromatogram: Rf = 0.39 (system toluene/diethyl ether, 1:1), Rf = 0.36 (system toluene/acetone, 4:1), Rf = 0.42 (system toluene/acetic acid ethyl ester, 1:1) and Rf = 0.10 (system toluene/acetic acid ethyl ester, 4:1); ultraviolet absorption spectrum (in 95% strength ethanol, non-denatured): $\lambda_{max}$ = 269 m$\mu$ ($\epsilon$ = 11500) and $\lambda_{min}$ = 241 m$\mu$ ($\epsilon$ = 5300); infrared absorption spectrum: characteristic bands at 2.93μ, 3.51μ, 5.57μ, 5.78μ, 5.92μ, 6.63μ (shoulder), 6.69μ, 7.27μ, 8.08μ, 8.54μ, 9.04μ, 9.61μ, 9.73μ and 9.91μ (in methylene chloride) and at 3.01μ, 5.62μ, 5.80μ, 6.02μ, 6.53μ, 6.70μ, 8.02μ and 9.66μ (in mineral oil).

EXAMPLE 61:

A solution of 2.9 g of 3-(4-methoxy-1-naphthylmethyl)-7β-phenylacetyl-amino-ceph-2-em-4ξ-carboxylic acid 2,2,2-trichloroethyl ester in 20 ml of methylene chloride is treated at 0° with 0.91 g of 3-chloro-perbenzoic acid. The mixture is left to stand for 1 hour at room temperature and is then washed with a 5% aqueous sodium sulphite solution, a 5% aqueous sodium hydrogen carbonate solution and a saturated aqueous sodium chloride solution. The solution is then dried over sodium sulphate and evaporated under reduced pressure. The residue is chromatographed on 100 g of silica gel, elution being carried out with methylene chloride, containing 10% of methyl acetate and fractions of 500 ml being taken. Fraction 3 contains the pure 3-(4-methoxy-1-naphthylmethyl)7β-phenylacetyl-amino-ceph-3-em-4-carboxylic acid 2,2,2-trichloroethyl ester-1-oxide, which melts at 195° – 196°; infrared absorption spectrum (in mineral oil): characteristic bands at 2,99μ, 5,61μ, 5,74μ, 5,99μ, 6,29μ and 6,52μ: thinlayer chromatogram (silica gel): Rf = 0.47 (system: toluene/ethyl acetate 1:1) and Rf = 0.43 (system: toluene/acetone 4:1).

EXAMPLE 62:

A solution of 3.35 g of the mixture of 7β-phenylacetyl-amino-3-(2-thenyl)-ceph-2-em-4ξ-carboxylic acid diphenylmethyl ester and 7β-phenylacetyl-amino-3-(2-thenyl)ceph-3-em-4-carboxylic acid diphenylmethyl ester (Example 51) in 50 ml of methylene chloride is cooled to 0° and treated with 1.1 g of 3-chloro-perbenzoic acid, the latter being added at once. Stirring is continued for 1 hour at room temperature and the reaction mixture is washed with a 50% sodium sulphite solution and a 5% aqueous sodium hydrogen carbonate solution, dried over magnesium sulphate and evaporated under reduced pressure to yield the 7β-phenylacetylamino-3-(2-thenyl)-ceph-3-em-4-carboxylic acid diphenylmethyl ester-1-oxide, which after recrystallisation from ethyl acetate, melts at 205°–206°: thin-layer chromatogram (silica gel): Rf = 0.45 (system: toluene/ethyl acetate 1:1) and Rf = 0.41 (system: toluene/acetone 4:1); infrared absorption spectrum (in mineral oil): characteristic bands at 3,00μ, 5,60μ, 5,79μ, 6,00μ and 6,52μ.

EXAMPLE 63:

A solution of 1.4 g of 3-furfuryl-7β-phenylacetylamino-ceph-2-em-4ξ-carboxylic acid diphenylmethyl ester in 40 ml of absolute methylene chloride is cooled in an ice bath, then treated with 0.52 g of purified 3-chloro-perbenzoic acid and left to stand for 1 hour at room temperature. The reaction solution is washed with a 5% aqueous sodium hydrogen sulphite solution, a 0.5 molar aqueous dipotassium hydrogen phosphate solution and distilled water; the aqueous phases are reextracted with a small amount of methylene chloride. The organic extracts are dried over magnesium sulphate and freed from solvent under reduced pressure. The residue is crystallised from a mixture of methyl acetate and cyclohexane and yields the 3-furfuryl-7β-phenylacetyl-amino-ceph-3-em-4-carboxylic acid diphenylmethyl ester-1-oxide, which melts at 205°–208° (analytical sample: m.p. 209°–210.5°, after recrystallisation from a mixture of ethyl acetate and cyclohexane and drying under a high vacuum at 35°C for 24 hours); $[\alpha]_D^{20} = +73° \pm 1°$ (c = 0.937 in doxane): thin-layer chromatography (silica gel): Rf = 0.53 (system: toluene/ethyl acetate 1:1), Rf = 0.37 (system: toluene/ethyl acetate 2:1), Rf = 0.41 (system: toluene/acetone 4:1), Rf=0.23 (system: toluene/acetone 9:1) and Rf = 0.89 (system: methylene chloride-/acetone 6:1); ultraviolet absorption spectrum (in 95% ethanol): $\lambda_{max}$ 266 mμ ($\epsilon$ = 9700) and $\lambda_{min}$ = 240 mμ ($\epsilon$ = 5150); infrared absorption spectrum (in mineral oil): characteristic bands at: 3,02μ, 5,58μ, 5,77μ, 6,00μ, 6,50μ, 6,66μ, 7,36μ, 8,11μ, 8,53μ, 9,00μ, 9,38μ, 9,66μ, 9,80μ, 10,38μ, 12,70μ, 13,32μ, 13,53μ, 13,71μ, 14,34μ and 14,44μ.

EXAMPLE 64:

A solution of 1.51 g of 3-(4-hydroxy-benzyl)-7β-phenylacetyl-amino-ceph-2-em-4ξ-carboxylic acid diphenylmethylester in 40 ml of methylene chloride is cooled in an ice bath and treated with 0.52 g of purified 3-chloro-perbenzoic acid. The mixture is allowed to react for 1 hour at room temperature and the reaction solution is extracted successively with a 5% aqueous sodium hydrogen sulphite solution, a 0.5 molar aqueous dipotassium phosphate solution and water. The aqueous phases are re-extracted twice with small amounts of methylene chloride. The organic extracts are combined, dried over anhydrous magnesium sulphate and evaporated to dryness under reduced pressure. The residue is crystallised from a mixture of methyl acetate and cyclohexane and yields the 3-(4-hydroxybenzyl)-7β-phenylacetyl-amino-ceph-3-em-4-carboxylic acid diphenylmethyl ester-1-oxide, which after further crystallisation from a mixture of methyl acetate and cyclohexane and drying under a high vacuum for 20 hours at 35° melts at 192°–193°; $[\alpha]\Sigma D20 + 36° \gamma 1°$ (c = 1.025 in dioxane); thinlayer chromatogram (silica gel: development with iodine): Rf = 0.18 (system: toluene/ethyl acetate 2:1), Rf = 0.36 (system: toluene/ethyl acetate 1:1), Rf = 0.24 (system: toluene/acetone 4:1), Rf = 0.07 (system: toluene/acetone 9:1) and Rf = 0.52 (system: methylene chloride/acetone 6:1); ultraviolet absorption spectrum (95% ethanol): $\lambda_{max}$ = 268 mμ ($\epsilon$ = 11300) and $\lambda_{min}$ = 241 mμ: infrared absorption spectrum (in mineral oil): characteristic bands at 2,94μ, 3,00μ, 5,60μ, 5,78μ, 5,85μ, 6,58μ, 6,65μ, 7,30μ, 7,99μ, 8,48μ, 8,70μ, 9,02μ, 9,78μ, 12,03μ, 13,45μ and 14,26μ.

EXAMPLE 65:

A solution of 15.1 g of 3-(5-methoxycarbonyl-furyl)7β-phenylacetyl-amino-ceph-2-em-4ξ-carboxylic acid diphenylmethyl ester (crystallised once from a mixture of ethyl acetate and diethyl ether) in 300 ml of absolute methylene chloride is cooled to 0° and treated with 4.87 g of purified 3-chloro-perbenzoic acid. The reaction solution is stirred for 1 hour at room temperature and then poured onto 500 ml of a 5% aqueous sodium sulphite solution. After shaking thoroughly, the organic phase is separated and washed with 3 × 200 ml of an aqueous sodium hydrogen carbonate solution and with 2 × 200 ml of water; the aqueous phases are re-extracted with 200 ml of methylene chloride. The organic extracts are dried over magnesium sulphate and concentrated. The concentrated solution is treated with cyclohexane while heating, whereupon a precipitate in the form of fine, colourless needles separates out, which after filtration, washing with diethyl ether and drying, yields the 3-(5-methoxycarbonylfurfuryl)-7β-phenylacetyl-amino-ceph-3-em-4-carboxylic acid diphenylmethyl ester 1-oxide, which melts after crystallisation from a mixture of acetone, diethyl ether and cyclohexane and drying for 20 hours at 35° and under a high vacuum at 198.5°–200° (uncorr.);$[\alpha]_D^{20} = +69°$ ± 1° (c = 0.963 in dioxane): thin-layer chromatogram (silica gel): Rf = 0.30 (system: toluene/ethyl acetate 1:1), Rf = 0.19 (system: toluene/ethyl acetate 2:1); Rf = 0.23 (system: toluene/acetone 4:1), Rf = 0.10 (system: toluene/acetone 9:1) and Rf = 0.72 (system: methylene chloride/acetone 6:1); ultraviolet absorption spectrum (in 95% ethanol): $\lambda_{max} = 267$ mμ (ε = 21800) and $\lambda_{min} = 233$ mμ (ε = 8600); infrared absorption spectrum (in mineral oil): characteristic bands at 2,99μ, 5,60μ, 5,77μ, 5,79μ (shoulder), 5,99μ, 6,52μ, 6,58μ, 6,68μ, 8,17μ, 8,29μ, 8,54μ, 8,69μ, 9,12μ, 9,59μ, 13,16μ, 13,88μ, 14,32μ and 14,44μ.

According to thin-layer chromatography (silica gel; inter alia system: toluene/ethyl acetate 1:1) the mother liquor contains still larger amounts of the desired product, which can be isolated by chromatography on silica gel (elution with methylene chloride containing 15–20% of ethyl acetate).

EXAMPLE 66:

A solution of 0.31 g of 3-(5-methoxycarbonyl-2-pyrrylmethyl)-7β-phenylacetyl-amino-ceph-2-em-4ξ-carboxylic acid diphenylmethyl ester in 10 ml of methylene chloride is cooled to 0°, treated with 0.100 g of 3-chloro-perbenzoic acid and stirred for 1 hour at room temperature. The reaction solution is washed with a 5% aqueous sodium sulphite and a 5% aqueous sodium hydrogen carbonate solution, dried over magnesium sulphate and evaporated to dryness under reduced pressure. The residue is chromatographed on 4 g of silica gel, the elution being carried out with 25 ml-fractions of methylene chloride containing 10% methyl acetate. Fractions 4–5 contain the desired 3-(5-methoxycarbonyl-2-pyrrylmethyl)7β-phenylacetyl-amino-ceph-3-em-4-carboxylic acid diphenylester-1-oxide, which after crystallisation from ethyl acetate melts at 195°–197°; thin-layer chromatography (silica gel): Rf = 0.28 (system: toluene/ethyl acetate 1:1) and Rf = 0.34 (system: toluene/acetone 4:1); ultraviolet absorption spectrum (in methanol): $\lambda_{max} = 274$ mμ (ε = 16400) and $\lambda_{min} = 245$ mμ (ε = 7000); infrared absorption spectrum (in mineral oil): characteristic bands at 2,99μ, 5,57μ, 5,68μ, 5,82μ, 6,04μ and 6,55μ.

EXAMPLE 67:

A solution of 17.4 g of amorphous 7β-(D-5-diphenyl-methoxycarbonyl-5-phthalimido-valeroyl-amino)-3-(5-methoxycarbonyl-furfuryl)-ceph-2-em-4ξ-carboxylic acid diphenylmethyl ester (purified by rapid chromatogram on silica gel) in 70 ml of methylene chloride is treated with 3.3 g of purified 3-chloro-perbenzoic acid and the pale yellow solution is left to stand for 90 minutes at room temperature. The reaction mixture is shaken with 50 ml of a 5% aqueous sodium hydrogen sulphite solution. The organic phase is separated, extracted with 100 ml of a 5 molar aqueous dipotassium hydrogen phosphate solution and washed repeatedly with water. The aqueous phases are re-extracted with 2 × 50 ml of methylene chloride and discarded. The combined organic extracts are treated with a small amount of an active charcoal preparation and dried over magnesium sulphate. The filtered solution is concentrated while heating to a volume of approx. 100 ml, the concentrate treated with diethyl ether until the onset of turbidity and left to stand initially at room temperature and then at approximately 4°. The colourless crystallised product is filtered off, washed with a mixture of diethyl ether and methylene chloride and with diethyl ether and dried. The analytical sample of the resulting 7β-(D-5-diphenylmethoxycarbonyl-5-phthalimido-valeroyl-amino)-3-(5-methoxycarbonyl-furfuryl)-ceph-3-em-4-carboxylic acid diphenylmethyl ester 1β-oxide is recrystallised twice from a mixture of methylene chloride and diethyl ether and dried under a high vacuum for 24 hours at 35°; m.p. 168°–169°; ultraviolet absorption spectrum (in 95% ethanol):$\lambda_{max}$ = 260 mμ (ε = 22000) and 239 mμ(ε = 17700) and $\lambda_{min}$ = 245 mμ (ε = 14500); infrared absorption spectrum: characteristic bands at: 2,96μ, 5,58μ, 5,73μ (shoulder), 5,75μ, 5,82μ, 5,93μ, 6,57μ, 7,18μ, 7,63μ, 7,95μ, 8,28μ, 8,56μ, 9,58μ, 9,69μ and 13,17μ (in mineral oil) and at 2,92μ, 5,55μ, 5,78μ, (shoulder), 5,80μ, 5,90μ, 6,60μ, 6,67μ, 7,19μ, 7,64μ, 8,22μ, 8,30μ, 8,54μ, 8,74μ, 9,12μ, 9,60μ, 9,82μ, 10,13μ and 10,48μ (in methylene chloride).

The mother liquors are evaporated to dryness, whereupon a yellow foam is obtained. In a thin-layer chromatogram (silica gel: system: toluene/acetone 2:1), the isomeric, more polar sulphoxide; relative Rf value = 0.64; and a less polar impurity in traces; Rf value = 1.30; can be detected in addition to a further amount of the above product. This mixture can be resolved by solumn chromatography on silica gel into the individual components.

EXAMPLE 68:

If in the process of Example 57 the 7β-[N-2-bromoethoxycarbonyl-D-(α)-phenylglycyl]-amino-3-(4-hydroxybenzyl)ceph-2-em-4ξ-carboxylic acid diphenylmethyl ester is used instead of the 3-(4-methoxy-1-naphthylmethyl)-7β-phenylacetylamino-2-em-4ξ-carboxylic acid 2,2,2-trichloroethyl ester in methylene chloride and oxidised with 3-chloro-perbenzoic acid, the mixture of the α- and β-1-oxides of 7β-[N-2-bromoethoxycarbonyl-D-(α)-phenylglycyl]-amino-3-(4-hydroxybenzyl)-ceph-3-em-4-carboxylic acid diphenylmethyl ester is obtained, which after recrystallisation from methanol melts at 170°–172°; thin-layer chromatogram (silica gel); α-isomer Rf = 0.20 and β-isomer Rf = 0.13 (system: toluene/acetone 4:1), α-isomer Rf = 0.91 and β-isomer Rf = 0.71 (system: chloroform/ethanol 20:1) and α-isomer Rf = 0.57 and β-isomer Rf = 0.34 (system: chloroform/ethanol 30:1); ultraviolet absorption spectrum (in ethanol):$\lambda_{max}$ = 207 mμ (ε = 13410) and $\lambda_{min}$ = 272 mμ (ε = 2790).

EXAMPLE 69:

A solution of 2.0 g of 3-(5-fluor-2-hydroxy-benzyl)7β-phenylacetylamino-ceph-2-em-4ξ-carboxylic acid in 10 ml of isopropanol is treated at 0°–5° in small amounts with 1.2 g of 3-chloro-perbenzoic acid and stirred for 2 hours. The reaction mixture is concentrated to half-volume and diluted with 10 ml of diethyl ether. The crystalline precipitate that forms is filtered off and recrystallised from methyl acetate to yield the 3-(5-fluoro-2-hydroxy-benzyl)-7-phenylacetylamino-ceph-3-em-4-carboxylic acid 1-oxide, which melts at 183°–185°; thin-layer chromatogram (silica gel) Rf = 0.48 (system: n-butanol/acetic acid/water 75:7.5:21), Rf = 0.64 (system: n-butanol/ethanol/water 40:10:50) and Rf = 0.77 (system: chloroform/methanol 1:1).

EXAMPLE 70:

A solution of 10.2 g of the mixture of 3-(2-methoxybenzyl)-7β-[N-2,2,2-trichloroethoxycarbonyl-D-(α)-phenylglycyl]-amino-ceph-2-em-4ξ-carboxylic acid and 3-(4-methoxybenzyl)-7β-[N-2,2,2-trichloroethoxycarbonyl-D-(α)-phenylglycyl]-amino-ceph-2-em-4ξ-carboxylic acid in 250 ml of a 1:1-mixture of acetonitrile and acetone is cooled to 0° and treated with 3.0 g of 3-chloro-perbenzoic acid. After the mixture has been stirred for 1½ hours while cooling with ice, white crystals precipitate, which can be dissolved again by adding 10 ml of dimethylsulphoxide. Stirring is continued for 1 hour while cooling with ice for 1 hour at room temperature. The solvent is then evaporated under reduced pressure, the residue is dissolved in methyl acetate and the solution is treated with diethyl ether. The white crystalline mixture of the 3-(2-methoxybenzyl)-7β-[N-2,2,2-trichloroethoxycarbonyl-D-(α)-phenylglycyl]-amino-ceph-3-em-4-carboxylic acid 1-oxide and the 3-(4-methoxybenzyl)-7β-[N-2,2,2-trichloroethoxycarbonyl-D-(α)-phenylglycyl]-amino-ceph-3-em-4-carboxylic acid 1-oxide precipitates, m.p. 216°–218° (with decomp.): thin-layer chromatogram (silica gel); Rf = 0.53 (system: n-butanol/ethanol/water 40:10:50), Rf = 0.88 (system: n-butanol/acetic acid/water 75:7.5:21) and Rf = 0.74 (system: ethyl acetate/pyridine/acetic acid/water 62:21:6:11); ultraviolet absorption spectrum (in acetonitrile): $\lambda_{max} = 270,5$ mμ ($\epsilon = 9930$), $\lambda_{min} = 221$ mμ ($\epsilon = 12790$) and $\lambda_{min} = 243$ mμ ($\epsilon = 5480$); infrared absorption spectrum (in mineral oil): characteristic bands at: 3,00μ, 5,62μ, 5,78μ, 5,96μ, 6,48μ, 6,83μ, 7,25μ, 7,99μ, 8,47μ, 8,96μ, 9,63μ, 10,00μ, 12,21μ, 13,88μ and 14,80μ.

EXAMPLE 71:

A solution of 5.40 g of 3-(2-thenyl)-7β-[N-2,2,2-trichloroethoxycarbonyl-D-(α)-phenylglycyl]-amino-ceph-2-em-4ξcarboxylic acid in 75 ml of isopropanol and 75 ml of acetonitrile is treated at 0°–5° with 2.22 g of 3-chloro-perbenzoic acid (techn. 85%). From the initially clear solution there separates out a white crystal broth, which after 2 hours stirring at 0°–5° is filtered off with the aid of a glass suction filter, washed with diethyl ether and recrystallised from a mixture of methanol, methyl acetate and cyclohexane to yield the 3-(2-thenyl)-7β-[-2,2,2-trichloroethoxycarbonyl-D-(α)-phenylglycyl]-amino-ceph-3-em-4-carboxylic acid 1-oxide, which melts at 216°–219°; thin-layer chromatogram (silica gel): Rf = 0.65 (system: n-butanol/acetic acid/water 75:7.5:21), Rf = 0.57 (system: n-butanol/ethanol/water 40:10:50) and Rf = 0.66 (system: chloroform/methanol 1:1); ultraviolet absorption spectrum (in ethanol): $\lambda_{max} = 239$ mμ ($\epsilon = 12300$) and $\lambda_{max} = 253$–261 mμ ($\epsilon = 10900$); infrared absorption spectrum (in mineral oil): characteristic bands at 3,05μ, 5,65μ, 5,80μ, 5,99μ and 9,98μ.

EXAMPLE 72:

A solution of 2.5 g of 3-(5-diphenylmethoxycarbonylfurfuryl)-7β-phenylacetylamino-ceph-2-em-4ξ-carboxylic acid diphenylmethyl ester in 10 ml of a 1:1-mixture of acetonitrile and isopropanol is treated at 0°–5° with 0.7 g of 3-chloroperbenzoic acid and stirred for 2 hours. The reaction product is worked up as usual (see Example 71) and the crude product is purified by column chromatography (silica gel; elution with a 4:1-mixture of methylene chloride and methyl acetate), to yield the colourless, foamy 3-(5-diphenylmethoxycarbonyl-furfuryl)-7β-phenylacetylamino-ceph-3-em-4-carboxylic acid diphenylmethyl ester 1-oxide; thin-layer chromatogram (silica gel); Rf = 0.43 (system: toluene/acetone 4:1) and Rf = 0.53 (system: toluene/ethyl acetate 4:1); ultraviolet absorption spectrum (in 95% aqueous ethanol): $\lambda_{max} = 269$–273 mμ ($\epsilon = 21000$).

EXAMPLE 73:

By treating 0.70 g of 3-(5-diphenylmethoxycarbonyl-furfuryl)-7β-phenylacetylamino-ceph-3-em-4-carboxylic acid diphenylmethyl ester 1-oxide with 5 ml of trifluoroacetic acid and 2 ml of anisole, the 3-(5-carboxy-furfuryl)-7β-phenylacetylamino-ceph-3-em-4-carboxylic acid 1-oxide is obtained; thin-layer chromatogram (silica gel): Rf = 0.15 (system: n-butanol/ethanol/water 40:10:50).

EXAMPLE 74:

A solution of 0.65 g of 3-(2,5-dimethoxy-benzyl)-7-(N-phenylacetyl-amino)-ceph-3-em-4-carboxylic acid diphenylmethyl ester 1-oxide in 45 ml of absolute dimethylformamide is treated with 3.6 g of sodium dithionite and the mixture is treated with 12 ml of acetyl chloride. The dark brown mixture, which becomes slightly warm during the reaction, is stirred for 3 hours at room temperature, then diluted with 200 ml of methylene chloride, and treated with a concentrated aqueous sodium hydrogen carbonate solution. When the vigorous evolution of carbon dioxide has subsided, the aqueous phase is separated off and re-extracted with methylene chloride. The organic extracts are repeatedly washed with water, dried over anhydrous magnesium sulphate and evaporated to dryness under reduced pressure.

The residue is chromatographed on 25 g of silica gel (containing 5% of water). 3-(2,5-dimethoxy-benzyl)-7-(N-phenylacetyl-amino)-ceph-3-em-4-carboxylic acid diphenylmethyl ester is eluted with a 7:3 mixture of toluene and methylene chloride and with pure methylene chloride; it melts at 157°–158.5°C (uncorrected) after recrystallisation from a mixture of methylene chloride and cyclohexane. The product is a single substance according to thin layer chromatography (silica gel G; systems toluene/diethyl ether, 1:1; toluene/acetic acid ethyl ester, 1:1; and toluene/acetone, 4:1) and in no way differs from the product obtainable according to the process of example 54.

EXAMPLE 75:

A solution of 2.65 g of 7β-phenylacetyl-amino-3-(2-thenyl)-ceph-3-em-4-carboxylic acid diphenylmethyl ester 1-oxide in 60 ml of a 9:1-mixture of tetramethylenesulphone and acetonitrile is cooled to 0° and treated in an ultrasonics bath with 2.25 g of sodium dithionite while stirring. One ml (1.1 g) of acetic acid chloride is added in small amounts within 60 minutes and the mixture is then poured into a cold 5% aqueous sodium hydrogen carbonate solution. Extraction is carried out three times with diethyl ether. The first extract yields a crystalline product; the resulting mother liquor and the two other extracts are washed with water until the tetramethylsulphone has been removed, dried over sodium sulphate and evaporated under reduced pressure. The residue is combined with the first crystalline product and chromatographed on 30 g of silica gel (purest). The 7β-phenylacetyl-amino-3-(2-thenyl)-ceph-3-em-4-carboxylic acid diphenylmethyl ester is eluted with methylene chloride and melts at 183°–184°.

EXAMPLE 76:

A solution of 0.317 g of 3-(4-methoxy-1-naphthylmethyl)-7β-phenylacetyl-amino-ceph-3-em-4-carboxylic acid 2,2,2-trichloroethyl ester 1-oxide in 10 ml of a 9:1-mixture of tetramethylenesulphone and acetonitrile is treated with 0.250 g of sodium dithionite. The mixture is cooled to 0° and agitated in an ultrasonics bath, then treated with 0.275 g of acetic acid chloride. The mixture is allowed to react for 30 minutes and an equal amount of acetic acid chloride is again added. After a further 30 minutes, the reaction mixture is poured out onto a 5% aqueous sodium hydrogen carbonate solution. After extraction with diethyl ester, the combined organic extracts are washed with water and a saturated aqueous sodium chloride solution, dried over magnesium sulphate and evaporated under reduced pressure. The residue is chromatographed on 10 g of silica gel, elution being carried out with methylene chloride and fractions of 50 ml being taken. Fractions 3 and 4 yield the 3-(4-methoxy-1-naphthylmethyl)-7β-phenylacetyl-amino-ceph-3-em-4-carboxylic acid 2,2,2-trichloroethyl ester, which after crystallisation from a mixture of ethyl acetate and diethyl ether melts at 164°–165°; thin-layer chromatogram (silica gel): Rf = 0.73 (system: toluene/ethyl acetate 1:1) and Rf = 0.59 (system: toluene/acetone 4:1); infrared absorption spectrum (in mineral oil): characteristic bands at 2,99μ, 5,63μ, 5,75μ, 5,99μ, 6,12μ, 6,29μ and 6,53μ.

EXAMPLE 77:

A solution of 1.55 g of 3-(5-methoxycarbonyl-2-furfuryl)-7β-phenylacetyl-amino-ceph-3-em-4-carboxylic acid diphenylmethyl ester 1-oxide, in 35 ml of a 9:1-mixture of absolute tetramethylenesulphone and acetonitrile, prepared while heating, is treated with 1.38 g of sodium dithionite-monohydrate. The mixture is stirred for a few minutes with a kinetic ultrasonic stirrer, in the process of which a fine suspension is formed. This suspension is cooled in an ice bath, treated with 0.6 ml of acetic acid chloride and stirred for 50 minutes at 0°–2°. The reaction solution is diluted with 100 ml of ethyl acetate, extracted with 3 portions (100, 50 and 50 ml, respectively) of 5% aqueous sodium hydrogen carbonate solution and washed with water. The aqueous extracts are re-extracted with 2 × 70 ml of ethyl acetate. The organic extracts are combined, dried over magnesium sulphate and freed from solvent under reduced pressure. The residue is covered with 50 ml of diethyl ether and the mixture is treated with approximately 200 ml of distilled water and left to stand for 30 minutes at 4°. The precipitate that forms is collected by suction filtration, washed with diethyl ether and dried under reduced pressure. The crude product is chromatographed on 65 g of silica gel. The 3-(5-methoxycarbonyl-2-furfuryl)-7β-phenylacetyl-amino-ceph-3-em-4-carboxylic acid diphenylmethyl ester is eluted with methylene chloride, containing 3% of methyl acetate and after crystallisation from a mixture of methylene chloride, diethyl ether and cyclohexane, melts at 189°–190° (analytical sample: m.p. 190°–191° in the form of colourless, felted needles after further crystallisation form the same mixture); $[\alpha]_D^{20} = -75° \pm 1°$ (c = 1.092 in chloroform): thin-layer chromatogram (silica gel): Rf = 0.72 (system: toluene/acetone 2:1), Rf = 0.60 (system: toluene/acetone 4:1), Rf = 0.36 (system: toluene/acetone 9:1) and Rf = 0.76 (system: toluene/ethyl acetate 1:1) and Rf = 0.65 (system: toluene/ethyl acetate 2:1); ultraviolet absorption spectrum (in 95% ethanol): $\lambda_{max} = 268$ mμ ($\epsilon = 21300$) and $\lambda_{min} = 273$ mμ ($\epsilon = 9100$); infrared absorption spectrum (in mineral oil): characteristic bands at: 2,99μ, 5,59μ, 5,74μ, 6,01μ, 6,48μ, 6,52μ (shoulder), 7,43μ, 7,61μ, 7,94μ, 8,12μ, 8,27μ, 8,51μ, 8,69μ, 9,16μ, 9,81μ, 10,36μ, 13,18μ, 13,61μ, 14,30μ and 14,42μ.

EXAMPLE 78:

A solution of 0.754 g of 3-(4-methoxybenzyl)-7β-[N-2,2,2-trichloroethoxycarbonyl-D-(α)-phenylglycyl]-amino-ceph-3-em-4-carboxylic acid 1-oxide in 5.5 ml of dimethylformamide is treated with 0.676 g of tin-II-chloride-dihydrate and the solution is cooled to 0°. While stirring, 2.4 ml of acetic acid chloride are added, the reaction mixture is stirred for 20 minutes at room temperature and poured onto ice. The resulting white crystalline product is filtered off, washed with water and recrystallised from a mixture of acetone and cyclohexane. The resulting 3-(4-methoxybenzyl)-7β-[N-2,2,2-trichloroethoxycarbonyl-D-(α)-phenylglycyl]-amino-ceph-3-em-4-carboxylic acid, which melts at 145°–148°; thin-layer chromatogram (silica gel): Rf = 0.65 (system: n-butanol/ethanol/water 40:10:50), Rf = 0.92 (system: n-butanol/acetic acid/water 75:7.5:21) and Rf = 0.85 (system: n-butanol/acetic acid/water 40:10:40); infrared absorption spectrum (in dioxane): characteristic bands at 3,05μ, 5,58μ, 5,65μ, 5,86μ, 6,50μ, 6,60μ, 7,61μ, 8,11μ, 8,44μ, 12,23μ, 13,27μ, 13,82μ and 14,23μ.

EXAMPLE 79:

A solution of 3.38 g of 3-(2-thenyl)-7β-[N-2,2,2-trichloroethoxycarbonyl-D-(α)-phenylglycyl]-amino-ceph-3-em-4-carboxylic acid 1-oxide and 3.1 g of tin-II-chloride in 100 ml of dimethylformamide is treated dropwise at −5° to 0° with 10 ml of acetic acid chloride, while stirring. After 1 hour, the reaction mixture is poured onto ice-cold water. The product precipitating in the process if filtered off, washed with water and dried in a vacuum exsiccator over phosphorous pentoxide. The resulting crude 3-(2-thenyl)-7β-[N-2,2,2-trichloroethoxycarbonyl-D-(α)-phenylglycyl]-amino-ceph-3-em-4-carboxylic acid, which melts at 128°–135°, is further processed without purification; thin-layer cromatogram (silica gel): Rf = 0.69 (system: n-butanol/acetic acid/water 75:7.5:21), Rf = 0.62 (system: n-butanol/ethanol/water 40:10:50) and Rf = 0.68 (system: chloroform/methanol 1:1).

EXAMPLE 80:

To a mixture of 1.3 g of crude 3-(5-carboxy-furfuryl)-7β-phenylacetylamino-ceph-3-em-4-carboxylic acid 1-oxide and 1.7 g of tin-II-chloride in 20 ml of dimethylformamide are added dropwise under anhydrous conditions 6 ml of acetic acid chloride, the temperature being maintained at 0°–5°. The reaction mixture is subsequently stirred for 2 hours and worked up in a conventional manner for free acids (see Example 78). Chromatography of the crude product (silica gel, washed with hydrochloric acid; elution with a 4:1-mixture of methylene chloride and ethyl acetate) and subsequent crystallisation from methyl acetate yield the 3-(5-carboxy-furfuryl)-7β-phenylacetylamino-ceph-3-em-4-carboxylic acid, m.p. 183°–186°; thin-layer chromatogram (silica gel); Rf = 0.24 (system: n-butanol/ethanol/water 40:10:50) and Rf = 0.55 (system: chloroform/methanol 1:1); infrared absorption spectrum (in mineral oil): characteristic bands at: 2,96μ, 3,18μ, 5,65μ, 5,73μ and 5,90μ.

EXAMPLE 81:

A solution of 0.365 g of 3-(4-methoxy-benzyl)-7-(N-phenylacetyl-amino)-ceph-3-em-4-carboxylic acid diphenylmethyl ester in 2 ml of anisole and 8 ml of trifluoracetic acid is left to stand for 20 minutes at room temperature. The trifluoracetic acid is removed under reduced pressure, the residue is mixed with toluene, and the mixture is again evaporated to dryness. The crude product is taken up in 50 ml of diethyl ether and 50 ml of 0.5 molar aqueous dipotassium hydrogen phosphate solution; the organic phase is separated off and twice extracted with 10 ml portions of the above dipotassium phosphate solution. The aqueous solutions are twice washed with 20 ml portions of diethyl ether, combined, covered with 50 ml of acetic acid ethyl ester and acidified to pH 2 with 20% strength aqueous phosphoric acid. The layers are separated; the aqueous solution is twice extracted with 20 ml portions of acetic acid ethyl ester, and the organic solutions are washed four times with 30 ml portions of a saturated aqueous sodium chloride solution, dried over anhydrous magnesium sulphate and evaporated under reduced pressure.

The residue is chromatographed on a column with 25 g of silica gel (with the addition of 5% of water). 3-(4-Methoxybenzyl)-7-(N-phenylacetyl-amino)-ceph-3-em-4-carboxylic acid is eluted with methylene chloride, containing 7 – 10% of acetone. A further quantity is obtained by elution with methylene chloride containing 12 – 20% of acetone, whilst the fraction eluted with pure acetone is contaminated with a polar substance. The fractions with the pure 3-(4-methoxybenzyl)-7-(N-phenylacetyl-amino)-ceph-3-em-4-carboxylic acid are combined, lyophilised from dioxane and dried for 15 hours under a high vacuum at 35°C. The initially amorphous substance can be obtained in a crystalline form and on recrystallisation from a mixture of acetic acid methyl ester, methylene chloride and cyclohexane melts at 170°–171.5°C; $[\alpha]_D^{20} = -56° \pm 1°$ (c = 0.961 in dioxane); thin layer chromatogram (silica gel G; development with iodine vapour): Rf = 0.64 (system n-butanol/acetic acid/water, 67:10:23), Rf = 0.715 (system n-butanol/acetic acid/water, 40:10:40), Rf = 0.74 (system acetic acid ethyl ester/pyridine/acetic acid/water, 62:21:6:11), Rf = 0.45 (system n-butanol/acetic acid/water, 75:7.5:21), Rf = 0.30 (system n-butanol/ethanol/water, 40:10:40) and Rf = 0.44 (system n-butanol/pyridine/acetic acid/water, 38:24:8:30); ultraviolet absorption spectrum: in 95% strength ethanol (non-denatured): $\lambda_{max} = 264$ mμ ($\epsilon = 9800$) and $\lambda_{min} = 239$ mμ ($\epsilon = 7450$), and in 0.1 N aqueous sodium hydrogen carbonate solution: $\lambda_{max} = 259$ mμ ($\epsilon = 13250$) and $\lambda_{min} = 237$ mμ ($\epsilon = 8850$).

EXAMPLE 82:

A mixture consisting of 0.7 g of 3-(2,5-dimethoxybenzyl)-7-(N-phenylacetyl-amino)-ceph-3-em-4-carboxylic acid diphenylmethyl ester and 4 ml of anisole in 16 ml of trifluoracetic acid is left to stand for 20 hours at room temperature. It is diluted with toluene and evaporated under reduced pressure; the residue is taken up several more times in toluene and the mixture evaporated, and the residue is then dried in a high vacuum and chromatographed on 30 g of silica gel (column) which has been purified with hydrochloric acid. The desired 3-(2,5-dimethoxy-benzyl)-7-(N-phenylacetyl-amino)-ceph-3-em-4-carboxylic acid is eluted with a 9:1 mixture of methylene chloride and acetic acid methyl ester and crystallised from a mixture of acetic acid methyl ester and cyclohexane; the colourless crystals melt at 207°C; thin layer chromatogram (silica gel G): Rf = 0.41 (system n-butanol/ethanol/water, 40:10:50), Rf = 0.74 (system n-butanol/acetic acid/water, 40:10:40) and Rf = 0.73 (system acetic acid ethyl ester/pyridine/acetic acid/water, 62:21:6:11); infrared absorption spectrum (in mineral oil): characteristic bands at 3.03μ, 5.62μ, 5.85μ, 5.95μ, 6.03μ, 6.48μ, 6.65μ, 7.32μ, 7.42μ, 8.06μ, 8.18μ, 9.54μ, 12.51μ, 13.83μ and 14.03μ; ultraviolet absorption spectrum (in 95% strength ethanol, non-denatured): $\lambda_{max} = 264$ mμ ($\epsilon = 8600$) and $\lambda_{min} = 243$ mμ ($\epsilon = 7100$).

EXAMPLE 83:

A mixture of 1.2 g of 7β-phenylacetly-amino-3-(2-thenyl)-ceph-3-em-4-carboxylic acid diphenylmethyl ester and 1.08 g of anisole is treated with 20 ml of trifluoroacetic acid and the batch is stirred for 15 minutes at room temperature. Upon addition of an equal amount of toluene, the solvent is evaporated under reduced pressure and the residue partitioned between ethyl acetate and an aqueous dipotassium hydrogen phosphate buffer solution (pH 7.8); the layers are isolated and the aqueous phase is washed repeatedly with ethyl acetate, then adjusted to pH 2.5 with 20% aqueous phosphoric acid. Extraction with ethyl acetate is carried out once more; the resulting extracts are washed with water and a saturated aqueous sodium chloride solution, dried over magnesium sulphate, and evaporated under reduced pressure. The residue is chromatographed on 20 g of silica gel (purest; deactivated with 10% water). The 7β-phenylacetylamino-3-(2-thenyl)-ceph-3-em-4-carboxylic acid, which is eluted with methylene chloride containing 30–50% of methyl acetate, cannot be obtained in crystalline form and by addition of 1 equivalent of a 2N solution of the sodium salt of 2-ethylpentanecarboxylic acid in methanol is converted into the sodium salt, which is precipitated by adding diethyl ether and is recrystallised from a mixture of methanol and ethanol, m.p. 227°–228° (with decomposition); thin-layer chromatogram (silica gel): Rf = 0.73 (system: n-butanol/acetic acid/water 67:10:23), Rf = 0.52 (system: n-butanol/ethanol/water 40:10:50) and Rf = 0.92 (system: ethyl acetate/pyridine/acetic acid/water 62:21:6:11); infrared absorption spectrum (in mineral oil): characteristic bands at: 3,01μ, 5.68μ, 6,01μ, 6,21μ and 6,50μ.

EXAMPLE 84:

A solution of 1.0 g of 3-(5-methoxycarbonyl-furfuryl)-7β-phenylacetyl-amino-ceph-3-em-4-carboxylic acid diphenylmethyl ester in a mixture of 16 ml of trifluoroacetic acid and 4 ml of anisole is left to stand for 15 minutes at room temperature. The reaction solution is then treated with 2 × 15 ml of glacial acetic acid and the batch evaporated to dryness under reduced pressure. The residual glacial acetic acid is removed by evaporation to dryness with the addition of toluene. The residue is dissolved in a small amount of methylene chloride and the solution diluted with methanol. The methylene chloride is evaporated while heating and the solution diluted with diethyl ether, whereupon colourless crystals begin to separate out; these are filtered off after cooling at 4°, washed with diethyl ether and pentane and briefly dried under reduced pressure. The resulting 3-(5-methoxycarbonyl-furfuryl)-7β-phenylacetyl-amino-ceph-3-em-4-carboxylic acid is purified by crystallisation from a mixture of methylene chloride, methanol and diethyl ether. The voluminous crystalline product precipitates very slowly on cooling the solution at 4°, is filtered off, washed with diethyl ether and petane and briefly dried. After drying for 16 hours under a high vacuum at 35°, the product melts at 154°–155.5°; $[\alpha]_D^{20} = -61° \pm 1°$ (c = 0.969 in dioxane); thin-layer chromatogram (silica gel; development with iodine); Rf = 0.60 (system: ethyl acetate/pyridine/acetic acid/water 62:21:6:11), Rf = 0.63 (system n-butanol/acetic acid/water 40:10:40), Rf = 0.66 (system: ethyl acetate/n-butanol/pyridine/acetic acid/water 42:21:21:6:10), Rf = 0.48 (system: n-butanol/acetic acid/water 75:7.5:21) and Rf = 0.31 (system: n-butanol/ethanol/water 40:10:50); ultraviolet absorption spectrum (in 95% ethanol): $\lambda_{max} = 268 m\mu$ ($\epsilon = 22300$) and $\lambda_{min} = 231 m\mu$ ($\epsilon = 7300$); infrared absorption spectrum (in mineral oil): characteristic bands at: 3,02μ, 5,61μ, 5,77μ, 5,83μ, 5,94μ, 6,00μ, 6,13μ, 6,51μ, 6,59μ, 7,35μ, 7,60μ, 8,40μ, 8,71μ, 9,11μ, 9,71μ, 10,20μ, and 12,34μ.

According to thin-layer chromatography on silica gel plates in the systems n-butanol/acetic acid/water (67:10:23) and ethyl acetate/pyridine/acetic acid/water (62:21:6:11), the mother liquors contain in addition to excess anisole a further amount of 3-(5-methoxycarbonyl-furfuryl)-7β-phenylacetylamino-ceph-3-em-4-carboxylic acid, which can be isolated by chromatography on silica gel (addition of 10% water); the elution of the product is effected with a 9:1-mixture of methylene chloride and methyl acetate.

EXAMPLE 85:

A solution of 0.789 g of 3-(4-hydroxy-benzyl)-7β-phenylacetyl-amino-ceph-3-em-4-carboxylic acid diphenylmethyl ester in 2 ml of anisole and 8 ml of trifluoroacetic acid is left to stand for 15 minutes at room temperature and evaporated under reduced pressure after addition of absolute toluene. The residue is partitioned between 50 ml of a 0.5 molar aqueous dipotassium hydrogen phosphate solution and 70 ml of diethyl ether; the organic phase is washed with a further amount of the buffer solution and discarded. The aqueous phases are combined, covered with 100 ml of ethyl acetate and acidified with 20% phosphoric acid. The aqueous solution is washed repeatedly with ethyl acetate; the organic solutions are combined, washed with a saturated aqueous sodium chloride solution, dried over magnesium sulphate and evaporated under reduced pressure. The residue is chromatographed on 35 g of silica gel (washed with concentrated hydrochloric acid); the 3-(4-hydroxybenzyl)-7β-phenylacetyl-amino-ceph-3-em-4-carboxylic acid is eluted with methylene chloride, containing 15–20% of methyl acetate, in the form of an amorphous product which is a uniform substance according to chromatography.

A solution of 0.444g of 3-(4-hydroxy-benzyl)-7β-phenylacetyl-amino-ceph-3-em-4-carboxylic acid in a small amount of methanol is treated with 0.5 ml of a 3-molar solution of the sodium salt of 2-ethyl-caproic acid in methanol. Diethyl ether is added dropwise, whereupon fine crystals begin to precipitate; these are filtered off, washed with a mixture of methanol and diethyl ether, then with diethyl ether and are dried for 16 hours under a high vacuum at 35°. The resulting sodium salt of the 3-(4-hydroxy-benzyl)-7β-phenylacetyl-amino-ceph-3-em-4-carboxylic acid decomposes on heating over 235° and turns brown. A further amount of the above sodium salt, which differs from the first product only through its pale yellow colour, crystallises from the mother liquor; $[\alpha]_D^{20} = +130° \pm 1°$ (c = 0.992 in water); thin-layer chromatography (silica gel): Rf = 0.69 (system: n-butanol/acetic acid/water 75:7.5:21), Rf = 0.45 (system: n-butanol/ethanol/water 40:10:50), Rf = 0.67 (system: n-butanol/acetic acid/water 40:10:40) and Rf = 0.60 (system: ethyl acetate/pyridine acetic acid/water 62:21:6:11); ultraviolet absorption spectrum (in 95% ethanol): $\lambda_{max} = 264 m\mu$ ($\epsilon = 11600$), shoulder at 225 mμ ($\epsilon = 13200$) and $\lambda_{min} = 239 m\mu$ ($\epsilon = 9000$); infrared absorption spectrum (in mineral oil): characteristic bands at: 2,92μ, 5,64μ, 5,99μ, 6,17μ, 6,27μ, 6,54μ, 6,60μ, 7,07μ, 7,89μ, 7,98μ, 8,42μ, 8,50μ, 12,13μ, 12,24μ, 12,77μ and 13,95μ.

EXAMPLE 86:

A solution of 0.885 g of the 3-(4-hydroxy-benzyl)-7β-phenylacetyl-amino-ceph-3-em-4-carboxylic acid diphenylmethyl ester in 25 ml of absolute acetonitrile is treated with 1.18 ml of acetyl chloride. The batch is cooled in an ice-bath and 1.2 ml of absolute pyridine are added dropwise. The precipitate that immediately forms is dissolved again by dilution with 80 ml of acetonitrile. After 2 hours, the yellow reaction solution is evaporated to dryness under reduced pressure while repeatedly adding toluene. The residue is taken up in 150 ml of methylene chloride and the solution is washed twice with a 1N aqueous sodium hydrogen carbonate solution and water; the aqueous solutions are back-extracted with methylene chloride. The organic extracts are combined, dried over anhydrous sodium sulphate and evaporated to dryness under reduced pressure. The residue is chromatographed on a column of 50 g of pure silica gel. Extraction is carried out with methylene chloride, fractions of 100 ml being taken. With fractions 6–9 the 3-(4-acetyloxy-benzyl)-7β-phenylacetyl-amino-ceph-3 -em-4-carboxylic acid diphenylmethyl ester, which is pure according to thin-layer chromatography, is eluted. It is recrystallised from a mixture of methylene chloride, diethyl ether and cyclohexane and melts in the form of colourless crystals at 172°–173.5°; $[\alpha]_D^{20} = -90° \pm 1°$ (c = 0.974 in chloroform); thin-layer chromatogram (silica gel): Rf = 0.58 (system: toluene/ethyl acetate 2:1), Rf = 0.37 (system: toluene/acetone 9:1) and Rf = 0.63 (system: toluene/acetone 4:1); ultraviolet absorption spectrum (in 95% ethanol): $\lambda_{max} = 264 m\mu$ ($\epsilon = 9350$) and $\lambda_{min} = 240 m\mu$ ($\epsilon = 7050$); infrared absorption spectrum: characteristic bands at: 3,01μ, 5,61μ, 5,69μ, 5,83μ, 6,03μ, 6,52μ, 7,40μ, 8,09μ, 8,15μ, 8,30μ, 8,54μ, 9,04μ, 9,85μ, and 10,93μ (in mineral oil) and at 2,90μ, 5,59μ, 5,65μ, 5,77μ, 5,91μ, 6,62μ, 7,27μ, 8,20μ, 8,30μ, 8,57μ, and 9,06μ (in methyl chloride).

EXAMPLE 87:

A mixture of 0.75 g of 3-(4-acetyloxy-benzyl)-7β-phenylacetyl-amino-ceph-3-em-4-carboxylic acid diphenylmethyl ester in 16 ml of trifluoroacetic acid and 4 ml of anisole is left to stand for 15 minutes at room temperature, then the resulting clear yellow solution is evaporated under reduced pressure while adding absolute toluene. The residue is taken up in 50 ml of diethyl ether and 50 ml of a 0.5 molar aqueous dipotassium hydrogen phosphate solution. The aqueous phase is isolated and washed with 2 × 22 ml of diethyl ether. The organic solutions are washed with a small amount of an aqueous dipotassium hydrogen phosphate solution and discarded. The combined aqueous phases are covered with 100 ml of ethyl acetate and acidified with 20% aqueous phosphoric acid; the aqueous phase is extracted with ethyl acetate. The organic solutions are combined, washed with a saturated aqueous sodium chloride solution, dried over sodium sulphate and evaporated under reduced pressure. The residue is chromatographed on 30 g of silica gel (washed with concentrated hydrochloric acid). Elution is carried out with a 9:1-mixture of methylene chloride and methyl acetate, fractions of 50 ml being taken. Fractions 5–11 contain the 3-(4-acetyloxybenzyl)-7β-phenylacetyl-amino-ceph-3-em-4-carboxylic acid, which according to thin-layer chromatography is a uniform substance and which after recrystallisation from a mixture of acetone, methyl acetate and cyclohexane, melts in the form of long, colourless needles at 207°–207.5°; $[\alpha]_D^{20} = -70° \pm 1°$ (c = 1.000 in dioxane); thin-layer chromatogram (silica gel): Rf = 0.72 (system: n-butanol/acetic acid/water 75:7.5:21), Rf = 0.39 (system: n-butanol/ethanol/water 40:10:50), Rf = 0.70 system: npbutanol-/acetic acid/water 40:10:40) and Rf = 0.60 (system: ethyl acetate/pyridine/acetic acid/water 62:21:6:11); ultraviolet absorption spectrum (in 95% ethanol): $\lambda_{max} = 260$ mμ ($\epsilon = 9250$) and $\lambda_{min} = 238$ mμ ($\epsilon = 7600$); infrared absorption spectrum (in mineral oil): characteristic bands at 2,99μ, 3,12μ, 5,57μ, 5,68μ, 5,84μ, 5,99μ, 6,14μ, 6,49μ, 6,63μ, 7,46μ, 8,10μ, 8,24μ, 8,44μ, 8,49μ, 9,96μ, 10,85μ, 11,72μ and 13,75μ.

EXAMPLE 88:

A solution of 0.715 g of 3-(4-hydroxy-3-methoxybenzyl)-7β-phenylacetylamino-ceph-3-em-4-carboxylic acid diphenylmethyl ester in 35 ml of pure formic acid is kept for 7 hours at 0°–4°. The formic acid is removed in a rotary evaporator under reduced pressure. The oily, partly foamy crude product is dried for 16 hours in a vacuum exsiccator over potassium hydroxide pills, then dissolved in methylene chloride and charged onto a column of 39 g of silica gel (purified with concentrated hydrochloric acid). The 3-(4-hydroxy-3-methoxy-benzyl)-7β-phenylacetylamino-ceph-3-em-4-carboxylic acid is eluted with 9:1- and 4:1-mixtures of methylene chloride and methyl acetate. The fractions, which are uniform according to thin-layer chromatography, are crystallised from a mixture of methylene chloride and diethyl ether. The colourless crystals melt at 174.5°–176° (with decomposition) after drying 15 hours under a high vacuum at 35°; thin-layer chromatogram (silica gel; plates with fluorescence indicator; detection with ultraviolet light λ = 254 mμ and iodine vapour): Rf = 0.71 (system: n-butanol/acetic acid/water 75:7.5:21), Rf = 0.41 (system: n-butanol/ethanol/water 40:10:50), Rf = 0.63 (system: n-butanol/acetic acid/water 44:12:44), Rf = 0.62 (system: ethyl acetate/pyridine/acetic acid/water 62:21:6:11), and Rf = 0.59 (system: ethyl acetate/n-butanol/pyridine/acetic acid/water 42:21:6:10); ultraviolet absorption spectrum (in 95% aqueous ethanol): $\lambda_{max} = 269$ mμ ($\epsilon = 9700$), $\lambda_{min} = 245$ mμ ($\epsilon = 7800$) and $\lambda_{shoulder} = 228$ mμ ($\epsilon = 12700$); infrared absorption spectrum (in mineral oil): characteristic bands at 2,80μ, 3,03μ, 5,58μ, 5,85μ, 6,01μ, 6,15μ, 6,54μ, 6,59μ and 7.38μ.

EXAMPLE 89:

A solution of 0.377 g of 3-(4-methoxy-benzyl)-7β-[N-2,2,2-trichloroethoxycarbonyl-D-(α)-phenylglycyl]-amino-ceph-3-em-4-carboxylic acid in 18 ml of dimethylformamide (degassed under a high vacuum) is diluted with 12 ml of 90% aqueous acetic acid and treated with 0.600 g of zinc powder. The mixture is stirred for 2 hours at room temperature; unreacted zinc dust is filtered off and the filter residue is rinsed with dimethylformamide. The filtrate is stirred for approximately 10 minutes with 50 ml of an anionexchange preparation (sulpho groups, hydrogen ion form). The exchanger is filtered off and washed with water. The filtrate is evaporated to dryness in a rotary evaporator under a high vacuum and at a bath temperature of less than 30°. The residue is dissolved in 9 ml of a 1:1:1-mixture of acetonitrile, methanol and water and adjusted to pH 4.3 with a 1:1-mixture of concentrated aqueous ammonia and water, in the process of which the solution becomes slightly turbid. After cooling the solution for 16 hours at approximately 4°C the precipitated crystals are filtered off, rinsed with diethyl ether and dried under a high vacuum at room temperature. The resulting white crystalline 3-(4-methoxybenzyl)-7β-[D-(α)-phenylglycyl]-amino-ceph-3-em-4-carboxylic acid melts at 163°–164°; thin-layer chromatogram (silica gel): Rf = 0.58 (system: n-butanol/acetic acid/water 75:7.5:21), Rf = 0.31 (system: n-butanol/ethanol/water 40:10:50) and Rf = 0.51 (system: n-butanol/acetic acid/water 40:10:40); ultraviolet absorption spectrum (in 0.01-N hydrochloric acid): $\lambda_{max} = 267$ mμ ($\epsilon = 7880$), $\lambda_{max} = 222$ mμ ($\epsilon = 11650$) and $\lambda_{min} = 242$ mμ ($\epsilon = 6220$); infrared absorption spectrum (potassium bromide): characteristic bands at 2,91μ, 3,40μ, 5,62μ, 5,88μ, 6,18μ, 6,59μ , 7,17μ, 7,32μ, 7,38μ, 8,02μ, 8,46μ, 9,01μ, 9,68μ, 12,20μ, 13,22μ and 14,31μ.

EXAMPLE 90:

A solution of 3.1 g of crude 3-(2-thenyl)-7β-[N-2,2,2-trichloroethoxycarbonyl-D-(α)-phenylglycyl]-amino-ceph-3-em-4-carboxylic acid in 120 ml of 90% aqueous acetic acid is treated with 6.0 g of zinc dust and stirred vigorously with a magnetic stirrer for 3 hours at room temperature. Unreacted zinc dust is filtered off and washed in several portions with a total of 50 ml of methanol. The filtrate is stirred for 15 minutes with 100 ml of an anion exchange preparation (sulpho groups; hydrogen ion form). The exchanger resin is filtered off and rinsed with several amounts of water. The aqueous solution is concentrated under a high vacuum at room temperature to a volume of approximately 100 ml. The resulting white precipitate passes largely into solution again when the concentrate is subsequently acidified with concentrated hydrochloric acid to pH 2 while cooling with ice. After filtration, the acid filtrate is extracted with ethyl acetate in order to remove a non-polar byproduct, filtered once more and brought to a pH-value of 4.2 by dropwise addition of a 1:1-mixture of concentrated aqueous ammonia and water, whereupon the batch becomes strongly turbin. After the mixture has been allowed to stand for 3 hours at 4°, the resulting crystalline product is filtered off, washed with water and dried in an exsiccator, then subsequently under a high vacuum. The resulting 3-(2-thenyl)-7β-[D-(α)-phenylglycol]-amino-ceph-3-em-4-carboxylic acid melts at 177°–180°; thin-layer chromatogram (silica gel): Rf = 0.48 (system: n-butanol/acetic acid/water 75:7.5:21) Rf = 0.39 (system: n-butanol/ethanol/water 40:10:50) and Rf = 0.33 (system: chloroform/methanol 1:1); ultraviolet absorption spectrum (in 0.01-N hydrochloric acid): $\lambda_{max} = 233–241$ m$\mu$ ($\epsilon = 11750$) and $\lambda_{max} = 259–265$ m$\mu$ ($\epsilon = 9900$); infrared absorption spectrum (in mineral oil): characteristic bands at 2,96$\mu$, 5,60$\mu$, 5,87$\mu$ and 6,26$\mu$.

EXAMPLE 91:

A suspension of 0.456 g of 3-(5-methoxycarbonylfurfuryl)-7β-phenylacetylamino-ceph-3-em-4-carboxylic acid in 30 ml of absolute methylene chloride is stirred for 30 minutes at 30° with 0.89 ml of absolute pyridine and 1.5 ml of trimethylchlorosilane. The resulting clear yellow solution is treated with 1.08 ml of pyridine and cooled to below −20°, then 8.9 ml of an 8% phosphorous pentachloride solution in methylene chloride is added dropwise and the solution is stirred for 40 minutes at a temperature of −12°. The brown solution is cooled again to below −20° and treated with 12.1 ml of absolute methanol. The mixture is allowed to react for 30 minutes at room temperature, whereupon the solution largely loses its colour. Upon addition of 2.5 ml of 25% aqueous formic acid, the pH of the solution is adjusted to 2.0 with 2.6 ml of triethylamine. The resulting suspension is further stirred for 30 minutes at room temperature. The pH is raised to 3.5 by the further addition of 9.6 ml of triethylamine. The suspension is left to stand for 1 hour at 0°; the fine, rather stimy precipitate is filtered off, washed with methanol, methylene chloride and diethyl ether and dried under a high vacuum. The 7β-amino-3-(5-methoxycarbonyl-furfuryl)-ceph-3-em-4-carboxylic acid is obtained in the form of a yellowish, microcrystalline powder. Additional, somewhat less pure material can be isolated by digesting the evaporated mother liquors and rinsing liquors with methylene chloride; ultraviolet absorption spectrum (in 0.1 N aqueous sodium hydrogen carbonate solution): $\lambda_{max} = 270$ m$\mu$ ($\epsilon = 21400$) and $\lambda_{min} = 234$ m$\mu$ ($\epsilon = 8200$); infrared absorption spectrum (in mineral oil): characteristic bands at 3,13$\mu$, 3,83$\mu$, 4,24$\mu$, 5,54$\mu$, 5,77$\mu$, 6,17$\mu$, 6,54$\mu$, 6,58$\mu$, (shoulder), 7.08$\mu$, 7,39$\mu$, 7,63$\mu$, 7,72$\mu$, 8,38$\mu$, 8,84$\mu$, 9,49$\mu$, 9,78$\mu$, 10,12$\mu$, 12,62$\mu$ and 13,21$\mu$.

EXAMPLE 92:

A 10% suspension of 0.100 g of 3-(5-methoxycarbonyl-furfuryl)-7-amino-ceph-3-em-4-carboxylic acid and 0.0644 g of tri-n-butylamine in absolute dimethylformamide is treated with a 5% solution of 0.0633 g of 2-chloroethylisocyanate. The reaction mixture is vibrated in an ultrasonics bath for 90 minutes at room temperature. The yellowish brown reaction solution is evaporated to dryness under a high vacuum and the residue is partitioned several times between 25 ml of a 0.5 molar aqueous dipotassium hydrogen phosphate solution and 10 ml of ethyl acetate. The aqueous extracts are covered with fresh ethyl acetate, acidified to pH 2 by dropwise addition of 5-molar aqueous phosphoric acid and extracted with three portions of ethyl acetate. The organic extracts are washed with water, dried over anhydrous magnesium sulphate and evaporated under reduced pressure. The residue is placed onto preparative thin-layer plates (silica gel, with fluorescence indicator). The plates are developed during approximately 5 hours in the system n-butanol/glacial acetic acid/water (44:12:44). After drying, the main band absorbing ultraviolet light ($\lambda = 254$ m$\mu$) is scraped from the plates and extracted several times with acetone. The extracts are filtered through a filter having a diatomaceous earth preparation as filter auxiliary and evaporated to dryness. The 7β-(2-chloroethylamino-carbonyl)-amino-3-(5-methoxycarbonyl-furfuryl)-ceph-3-em-4-carboxylic acid is obtained in the form of a glassy, colourless residue; ultraviolet absorption spectrum (95% aqueous ethanol): $\lambda_{max} = 269$ m$\mu$ ($\epsilon = 22100$).

EXAMPLE 93:

A solution of 0.0427 g of phenyloxyacetyl chloride in 3 ml of absolute methylene chloride is added at −15°C to an almost clear solution of 0.0677 g of 3-(5-methoxycarbonyl-furfuryl)-7-amino-ceph-3-em-4-carboxylic acid and 0.070 ml of absolute triethylamine in 5 ml of methylene chloride. The combined solutions are allowed to react for 1 hour at −15° and for a further hour at room temperature, and the reaction product is worked up analogously to the process of Example 92. The resulting amorphous residue is lyophilised from a small amount of acetic acid. The colourless 3-(5-methoxycarbonyl-furfuryl)-7β-phenyloxyacetylamino-ceph-3-em-4-carboxylic acid shows in infrared absorption spectrum (in methylene chloride) characteristic bands at: 2,91$\mu$, 3,85$\mu$, 5,59$\mu$, 5,77$\mu$, 5,88$\mu$, 6,10$\mu$, 6,24$\mu$, 6,60$\mu$ and 7,61$\mu$ ultraviolet absorption spectrum (in 95% ethanol): $\lambda_{max} = 270$ m$\mu$ ($\epsilon = 22400$).

EXAMPLE 94:

A solution of 0.0402 g of 2-thienyl-acetylchloride in 3 ml of absolute methylene chloride is treated with an almost clear solution of 0.068 g of 3-(5-methoxycarbonylfurfuryl)-7-amino-ceph-3-em-4-carboxylic acid and 0.070 ml of absolute triethylamine and the mixture worked up according to the process described in Example 92. The 3-(5-methoxycarbonyl-furfuryl)-7β-(2-thienylacetyl)-amino-ceph-3-em-4-carboxylic acid, which is lyophilised from acetic acid, is a uniform substance according to thin-layer chromatography (silica gel plates: detection with ultraviolet light $\lambda = 254$ m$\mu$ or iodine vapour): Rf = 0.57 (system: ethyl acetate/pyridine/acetic acid/water 62:21:6:11), Rf = 0.45 (system: n-butanol/acetic acid/water 75:7.5:21), Rf = 0.60 (system: n-butanol/acetic acid/water 44:12:44) and Rf = 0.30 (system: n-butanol/ethanol/water 40:10:50).

EXAMPLE 95:

If in the process of Example 94 bromoacetic acid chloride is used as acylating reagent and diisopropylethylamine as base, 7β-bromoacetylamino-3-(5-methoxycarbonyl-furfuryl)-ceph-3-em-4-carboxylic acid is obtained according to the process of Example 92, which in thin-layer chromatgram has an Rf value of 0.40 (silica gel plates; systems: n-butanol/acetic acid/water 75:7.5:21); ultraviolet absorption spectrum (in 95% ethanol): $\lambda_{max} = 268$m$\mu$ ($\epsilon = 22000$).

EXAMPLE 96:

A solution of 0.5 mmole of the 7β-bromoacetylamino-3-(5-methoxycarbonyl-furfuryl)-ceph-3-em-4-carboxylic acid obtainable according to the process of Example 95, 0.066 g of 4-mercaptopyridine and 0.057 g of diisopropylethyl amine in 10 ml of absolute dimethylformamide is allowed to react for 5 hours at room temperature. The reaction mixture is evaporated to dryness under a high vacuum and the residue is digested in a 1:1-mixture of diethyl ether and acetone. After stirring for 20 minutes with a magnetic stirrer, the pulverulent, faintly yellow precipitate is filtered off and washed. The resulting 3-(5-methoxycarbonyl-furfuryl)-7β-(4-pyridylthioacetyl)-amino-ceph-3-em-4-carboxylic acid is homogeneous according to thin-layer chromatography, Rf = 0.38 (silica gel plates; system: n-butanol/water/pyridine/acetic acid 42:30:24:4 detection with ultraviolet light λ=254 mμ or iodine vapour); infrared absorption spectrum (in mineral oil): characteristic band at 5,59 mμ.

EXAMPLE 97:

If in the process of Example 77 the mixture of the α- and β-1-oxides of 7β-[N-2-bromoethoxycarbonyl-D-(α)-phenylglycyl]-amino-3-(4-hydroxybenzyl)-ceph-3-em-4-carboxylic acid diphenylmethyl ester is used as the starting material, one obtains the 7β-[N-2-bromoethoxycarbonyl-D-(α)-phenylglycyl]-amino-3-(4-hydroxybenzyl)-ceph-3-em-4-carboxylic acid diphenylmethyl ester, in which the benzhydryl ester grouping is split upon treatment with trifluoroacetic acid in the presence of anisole and the 2-bromoethoxycarbonylamino grouping by treatment with zinc in the presence of 90% aqueous acetic acid; the resulting compound is the 3-(4-hydroxybenzyl)-7β-[D-(α)-phenylglycyl]-amino-ceph-3-em-4-carboxylic acid.

Upon treatment of 7β-[N-2-bromoethoxycarbonyl-D-(α)-phenylglycyl]-amino-3-(4-hydroxybenzyl)-ceph-3-em-4-carboxylic acid diphenylmethyl ester with acetic acid chloride according to the process of Example 86, the 3-(4-acetyloxybenzyl)-7β-[N-2-bromoethoxycarbonyl-D-(α)-phenylglycyl]-amino-ceph-3-em-4-carboxylic acid diphenylmethyl ester is obtained, in which the benzhydryl ester grouping is split upon treatment with trifluoroacetic acid in the presence of anisole and the 2-bromoethoxycarbonylamino grouping by treatment with zinc in the presence of 90% aqueous acetic acid; one obtains the 3-(4-acetyloxy-benzyl)-7β-[D-(α)-phenylglycyl]-amino-ceph-3-em-4-carboxylic acid.

If one oxidizes the 3-(5-methoxycarbonyl-furfuryl)-7β-[N-2-bromoethoxycarbonyl-D-(α)-phenylglycyl]-amino-ceph-2-em-4ξ-carboxylic acid diphenylmethyl ester with 3-chloroperbenzoic acid according to the process of Example 65 and reduces the resulting 3-(5-methoxycarbonyl-furfuryl)-7β-[N-2-bromoethoxycarbonyl-D-(α)-phenylglycyl]-amino-ceph-3-em-4-carboxylic acid diphenylmethyl ester 1-oxide with sodium dithionite according to the process of Example 77, the 3-(5-methoxycarbonyl-furfuryl)-7β-[N-2-bromoethoxycarbonyl-D-(α)-phenylglycyl]-amino-ceph-3-em-4-carboxylic acid diphenylmethyl ester is formed, in which the benzhydryl ester grouping is split upon treatment with trifluoroacetic acid in the presence of anisole and the 2-bromoethoxycarbonylamino grouping by treatment with zinc in the presence of 90% aqueous acetic acid; the resulting compound is the 3-(5-methoxycarbonyl-2-furfuryl)-7β-[D-(α)-phenylglycyl]-4-carboxylic acid.

EXAMPLE 98:

Lyophilized ampules or vials containing 0.5 g of the sodium salt of 3-(4-hydroxybenzyl)-7β-phenylacetylamino-ceph-3-em-4-carboxylic acid are prepared as follows:

Formula (for one ampule or vial):
sodium salt of 3-(4-hydroxybenzyl)-7β-phenylacetyl
amino-ceph-3-em-4-carboxylic acid      0.5 g
mannitol                                0.05 g A sterile aqueous solution of the sodium salt 3-(4-hydroxybenzyl)-7β-phenylacetylamino-ceph-3-em-4-carboxylic acid and of the mannitol is lyophilized under aseptic conditions in 5 ml ampules or 5 ml viales; the ampules and vials are closed and examined.

EXAMPLE 99:

Lyophilized ampules and vials containing 1.0 g of the sodium salt of 7β-phenylacetylamino-3-(2-thenyl)-ceph-3-em-4-carboxylic acid are prepared as follows:

Formula (for one ampule or vial):
sodium salt of 7β-phenylacetylamino-3-(2-thenyl)-
ceph-3-em-4-carboxylic acid             1.0 g
mannitol                                0.1 g A sterile aqueous solution of the sodium salt of 7β-phenylacetylamino-3-(2-thenyl)-ceph-3-em-4-carboxylic acid and of the mannitol is lyophilized under aseptic conditions in 5 ml ampules or 5 ml vials; the ampules and vials are closed and examined.

We claim:
1. Compounds having the formula

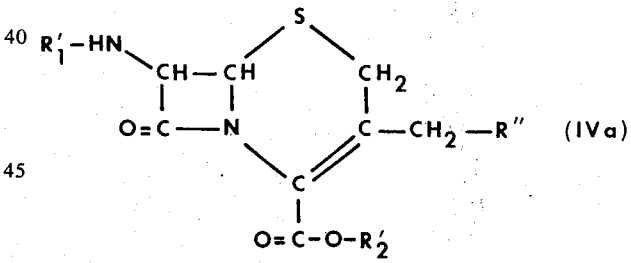

(IVa)

in which R" represents 2- or 4-hydroxy-phenyl, 2,5- or 3,4-dihydroxy-phenyl, 2- or 4-lower alkoxy-phenyl, 2,4-, 2,5- or 3,4-dimethoxy-phenyl, 2- or 4-lower alkanoyloxy-phenyl, 4-lower alkylthio-phenyl, 2-thienyl, 2-furyl, 5-carboxy-2-furyl or 5-lower alkoxycarbonyl-2-furyl, and in which $R_1'$ represents an acyl radical of the formula

(Ic)

in which Ar represents phenyl, 3- or 4-hydroxy-phenyl, 3-chloro-4-hydroxy-phenyl, 3,5-dichloro-4-hydroxy-phenyl or thienyl, and $R_3$ represents hydrogen, amino, t-lower alkoxycarbonylamino, 2-halogenolower alkoxycarbonylamino, guanylureido, sulphoamino, carboxyl or sulpho, and $R_2'$ represents hydrogen or tert.-lower alkyl, 2-halogenlower alkyl, phenacyl, benzhydryl, 4,4'-dimethoxy-diphenylmethyl or lower alkanoyloxymethyl, and pharmaceutically acceptable salts of such compounds having salt-forming groups.

2. A compound as claimed in claim 1 and being a member selected from the group consisting of 7β-phenylacetylamino-3-(2-thenyl)-ceph-3-em-4-carboxylic acid and pharmaceutically acceptable salts thereof.

3. A compound as claimed in claim 1 and being a member selected from the group consisting of 3-(5-methoxycarbonyl-furfuryl)-7β-phenylacetylamino-ceph-3-em-4-carboxylic acid and pharmaceutically acceptable salts thereof.

4. A compound as claimed in claim 1 and being a member selected from the group consisting of 3-(4-hydroxybenzyl)-7β-phenylacetyl-amino-ceph-3-em-4-carboxylic acid and pharmaceutically acceptable salts thereof.

5. A compound as claimed in claim 1 and being a member selected from the group consisting of 3-(4-acetyloxybenzyl)-7β-phenylacetyl-amino-ceph-3-em-4-carboxylic acid and pharmaceutically acceptable salts thereof.

6. A compound as claimed in claim 1 and being a member selected from the group consisting of 3-(2-thenyl)-7β-[D-(α)-phenylglycyl]-amino-ceph-3-em-4-carboxylic acid and pharmaceutically acceptable salts thereof.

7. A compound as claimed in claim 1 and being a member selected from the group consisting of 7β-amino-3-(5-methoxycarbonyl-furfuryl)-ceph-3-em-4-carboxylic acid, or pharmaceutically acceptable salts thereof.

8. A compound as claimed in claim 1 and being a member selected from the group consisting of 3-(4-hydroxybenzyl)-7β-[D-(α)-phenylglycyl]-amino-ceph-3-em-4-carboxylic acid and pharmaceutically acceptable salts thereof.

9. A compound as claimed in claim 1 and being a member selected from the group consisting of 3-(4-acetyloxybenzyl)-7β-[D-(α)-phenylglycyl]-amino-ceph-3-em-4-carboxylic acid and pharmaceutically acceptable salts thereof.

10. A compound as claimed in claim 1 and being a member selected from the group consisting of 3-(5-methoxycarbonyl-2-furfuryl)-7β-[D-(α)-phenylglycyl]-amino-ceph-3-em-4-carboxylic acid and pharmaceutically acceptable salts thereof.

* * * * *